United States Patent [19]

Hansen, Jr. et al.

[11] Patent Number: 4,847,241

[45] Date of Patent: Jul. 11, 1989

[54] FLUORENYL SUBSTITUTED TYROSYL DIPEPTIDE AMIDES WHICH ARE USEFUL IN TREATING PAIN

[75] Inventors: Donald W. Hansen, Jr., Chicago; Robert W. Hamilton, Wilmette; Barnett S. Pitzele; Michael Clare, both of Stokie, all of Ill.

[73] Assignee: G. D. Searle & Co., Chicago, Ill.

[21] Appl. No.: 145,954

[22] Filed: Jan. 20, 1988

Related U.S. Application Data

[60] Division of Ser. No. 882,794, Jul. 14, 1986, which is a continuation-in-part of Ser. No. 829,266, Jan. 14, 1986, abandoned, which is a continuation-in-part of Ser. No. 765,882, Aug. 14, 1985.

[51] Int. Cl.$^4$ .................. A61K 37/02; C07K 7/12
[52] U.S. Cl. .................... 514/19; 260/998.2
[58] Field of Search ............ 514/19; 260/998.2

[56]        References Cited
        U.S. PATENT DOCUMENTS 4,127,535  11/1978  Coy et al. .................. 514/19
4,599,325  7/1986   Hansen, Jr. et al. .......... 514/19

Primary Examiner—Richard A. Schwartz
Assistant Examiner—Zinna Nathington
Attorney, Agent, or Firm—Frank P. Grassler; Paul D. Matukaitis

[57]            ABSTRACT

The invention relates to novel substituted tyrosyl alanine dipeptide amides of the formula:

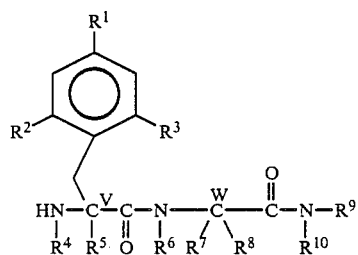

and the pharmaceutically acceptable acid addition salts thereof wherein $R^1$ is hydrogen, lower alkyl, hydroxy, —OCO$_2$ lower alkyl, lower alkoxy, —O(CH$_2$)$_n$—phenyl with the phenyl optionally substituted by halogen, —NO$_2$, —CN, —NH$_2$ or lower alkyl wherein n is 1 to 4; $R^2$ and $R^3$ represent lower alkyl, halogen, or lower alkoxy, or either one of $R^2$ or $R^3$ is hydrogen and the other is lower alkyl, lower alkoxy or halogen; $R^4$, $R^5$, $R^6$, $R^7$, $R^8$, and $R^9$ may be the same or different and represent hydrogen or lower alkyl; $R^{10}$ is selected from the group consisting of

—(ALK)X where ALK represents alkylene, thioalkylene, oxyalkylene, having 1 to 5 carbon atoms; alkenylene and alkynylene having 2 to 4 carbon atoms; and X represents pyridyl, pyrimidinyl, 9H-fluoren-9-yl, diphenylmethyl, thienyl, carboxy, lower alkoxy carbonyl, substituted phenyl wherein the phenyl substitutent is amino, hydroxy, halogen, nitro, methylenedioxy, lower alkyl, carboxy, lower alkoxycarbonyl, lower alkoxy, carboxamide, diloweralkylamino or X represents phenyl when ALK is not alkylene; or $R^{10}$ is

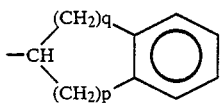

where p and q are independently 1 to 4; or $R^9$ and $R^{10}$ together with N is

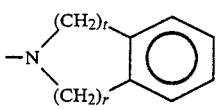

where r and t are independently 1 to 4; v represents an symmetric carbon that may be racemic or have the D or L configuration; w represents an asymmetric carbon when $R^7$ and $R^8$ are not the same that may be racemic or have the D or L configuration. These compounds are useful as analgesic and/or antihypertensive compounds.

5 Claims, No Drawings

FLUORENYL SUBSTITUTED TYROSYL DIPEPTIDE AMIDES WHICH ARE USEFUL IN TREATING PAIN

This application is a division of Ser. No. 06/882,794 filed July 14, 1986, now pending, which is a continuation-in-part of Ser. No. 829,266 filed Feb. 14, 1986 now abandoned which is a continuation-in-part of Ser. No. 765,882 filed Aug. 14, 1985, now pending.

FIELD OF THE INVENTION

The present invention relates to novel dipeptide amides. In particular, it provides novel dipeptide derivatives of Formula 1 which are useful as analgesic or antihypertensive agents.

BACKGROUND OF THE INVENTION

In 1975, a pentapeptide, methionine enkepthalin, was reported by Hughes et al., Nature, 258, 577 (1975). This peptide is found in many areas of the brain where it appears to act as a neurotransmitter or neuromodulator in a central pain-suppressant system. The natural peptide binds stereospecifically to partially purified brain opiate receptor sites, see for example, Bradberry et al., Nature, 260, 793 (1976). The natural peptide is also highly active in bioassays for opiate activity but exhibits only weak, fleeting analgesic activity when injected directly into the brain of the rat, see for example, Belluzi et al., Nature, 260, 625 (1976)

In order to overcome the lack of in vivo activity, a number of investigators have made numerous modifications in the methionine enkephalin structure, such as substituting the glycine in the 2-position with a D-amino acid, N-methylation of the L-tyrosine, substituting the 4-phenylalanine with, for example, methyl or halo, modifying the C-terminus, etc., to produce enkephalin derivatives of varying properties and potencies.

Kiso, et al., "Peptide Chemistry 1981,": 65–70, Protein Research Foundation, Osaka, Japan (1982), disclosed the synthesis and activity of short chain enkephalin-like peptides, among them tripeptide and dipeptide alkylamides such as N-methyl tyrosine (D) methionine sulfoxide glycine-methylphenethylamide (2) and tyrosine-(D) methionine sulfoxide phenylpropylamide (3).

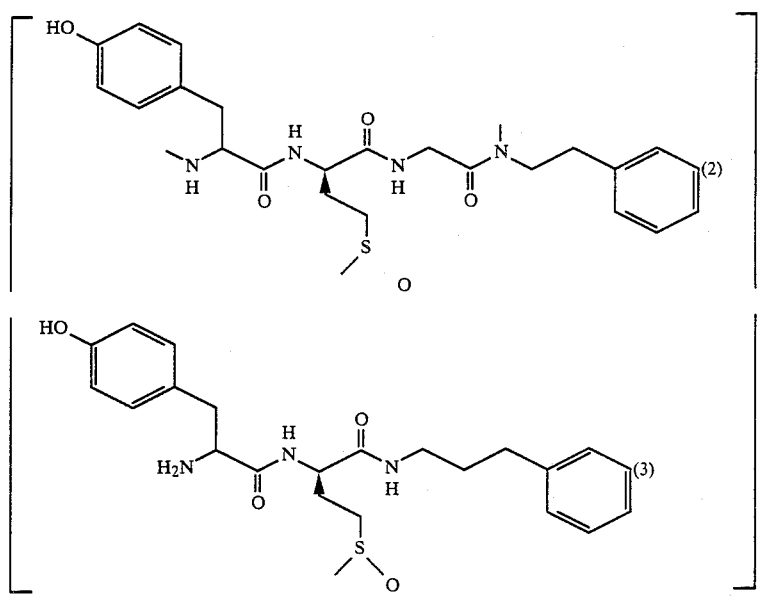

Vavrek, et al., Peptides 2, 303, 1981 disclosed analogs of enkephalin, among them the dipeptide tyrosine-D-alanine-phenylpropylamide (Tyr-(D)Ala-PPA) (4).

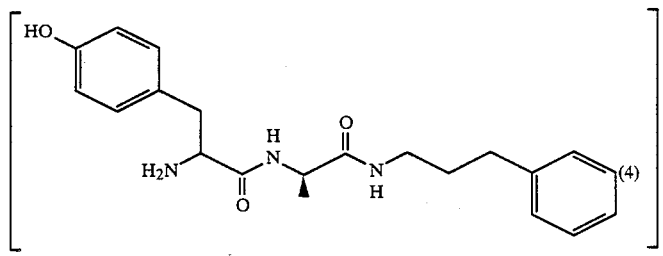

The compounds of this invention have unexpected and surprisingly superior properties when compared to the Vavrek compound. The present invention provides new dipeptide derivatives which show improved potency as analgesic agents by both oral and parenteral routes of administration. Additionally, U.S. Pat. No. 4,316,892 relates to certain derivatives of methionine enkephalin derivatives useful as analgesic agents.

SUMMARY OF THE INVENTION

This invention encompasses analgesic tyrosine derivatives of formula I:

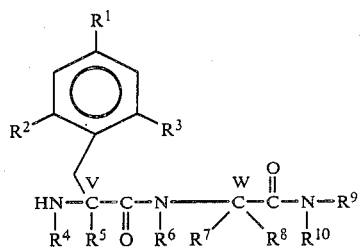

and the pharmaceutically acceptable acid addition salts thereof wherein $R^1$ is hydrogen, lower alkyl, hydroxy, $-O-CO_2$ lower alkyl, lower alkoxy, $O(CH_2)_n$ phenyl with the phenyl optionally substituted by halogen, $-NO_2$, $-CN$, $-NH_2$ or lower alkyl wherein n is 1 to 4; $R^2$ and $R^3$ represent lower alkyl, halogen, or lower alkoxy, or either one or $R^2$ or $R^3$ is hydrogen and the other is lower alkyl, lower alkoxy or halogen; $R^4$, $R^5$, $R^6$, $R^7$, $R^8$, and $R^9$ may be the same or different and represent hydrogen, or lower alkyl; $R^{10}$ is selected fom the group consisting of

—(ALK)X where ALK represents alkylene, thioalkylene, or oxyalkylene, having 1 to 5 carbon atoms; or alkenylene and alkynylene having 2 to 4 carbon atoms; and X represents pyridyl, pyrimidinyl, 9H-fluoren-9yl, di-phenylmethyl, thienyl, carboxy, loweralkoxycarbonyl, substituted phenyl wherein the phenyl substituent is amino, hydroxy, halogen, nitro, methylenedioxy, lower alkyl, carboxy, lower alkoxycarbonyl, lower alkoxy carboxamide, diloweralkylamino or X represents phenyl when ALK is not alkylene; or $R^{10}$ is

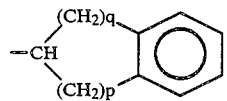

where p and q are independently 1 to 4; or $R^9$ and $R^{10}$ together with N is

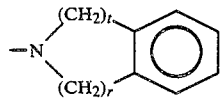

where r and t are independently 1 to 4; v represents an asymmetric carbon that may be racemic or have the D or L configuration; w represents an asymmetric carbon when $R^7$ and $R^8$ are not the same that may be racemic or have the D or L configuration.

In the context of this invention and the definition of $R^1$ through $R^{10}$ lower alkyl means straight or branched chain alkyls having 1 to 6 carbon atoms such as methyl, ethyl, propyl, isopropyl, butyl, iso-butyl, pentyl and isomers thereof, and hexyl and isomer thereof.

Lower alkoxy means alkoxy having 1 to 6 carbon atoms where the alkyl moiety are as described above for lower alkyl. Halo refers to chloro, fluoro, bromo and iodo.

DESCRIPTION OF THE SPECIFIC EMBODIMENTS

The compounds described in this invention are illustrated in Examples 1-182 are synthesized by either of two procedures shown in schemes 1 and 2 as Route A and Route B. Many of the compounds can be prepared by either route with the principal difference being the reaction sequence.

Route A in Scheme I and Route B in Scheme II illustrate two methods for making compounds of this invention. In Route A is blocked amino acid derivative X is reacted with a dialkylamino XI by mixed anhydride coupling and the blocking group is removed by catalytic hydrogenation to provide amide XII. A blocked tyrosine derivative XIII is reacted with amide XII by the mixed anhydride method to provide XIV which is separated into diastereomers, which are separately deblocked to provide compounds of formula I.

In Route B Scheme II the ester of the amino group derivative is coupled with XIII by mixed anhydride coupling to provide ester XVI. This ester XVI is separated into diastereomers. For example, if XV is a D amino acid derivative and XIII is a DL tyrosine derivative, the DD and LD diastereomers are provided. The appropriate dialkylamine is then coupled to the separated diastereomer of XVII, and the product is deblocked to provide the compounds of Formula I.

In Schemes I and II Boc refers to tertiary butoxy carbonyl and $R^1$ through $R^{10}$ are as previusly defined. Z is Boc or benzyloxy. Z can be Boc in non sulfur containing X and removed by hydrolysis in hydrochloric acid in diocan.

Diastereomers are separated by standard techniques such as crystalization or column chromatography.

SCHEME I
ROUTE A

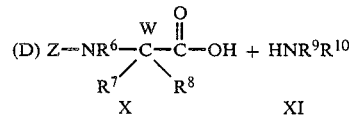

1. mixed anhydride coupling
2. $H_2/Pd(C)$

SCHEME I
ROUTE A
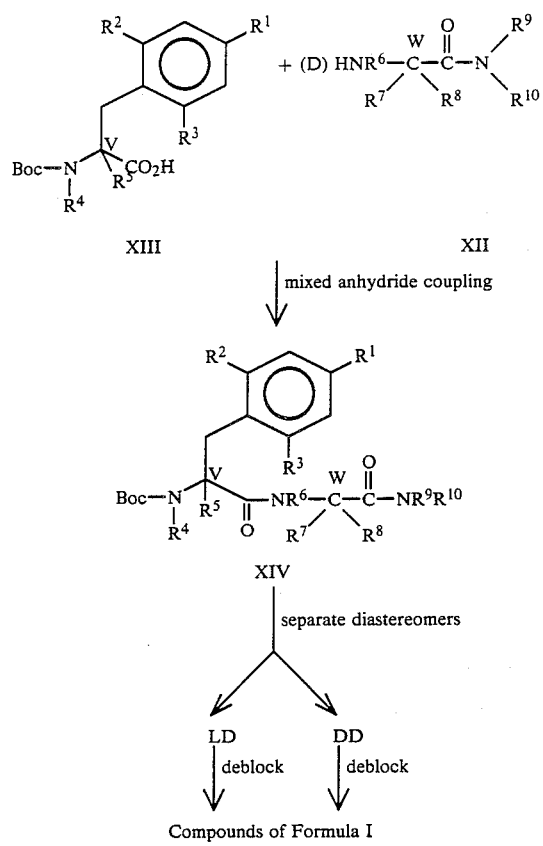
Compounds of Formula I
SCHEME II
ROUTE B
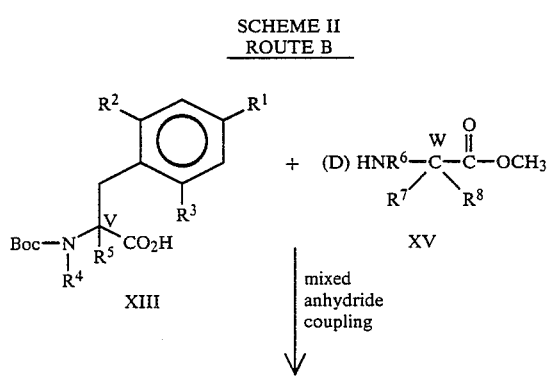
-continued
SCHEME II
ROUTE B
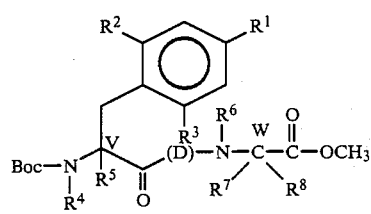
XVI
1. separate diastereomers
2. saponify
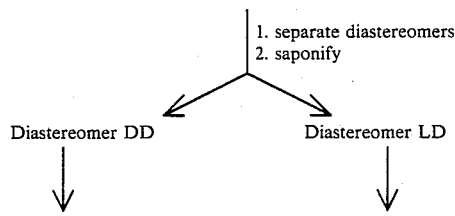
Diastereomer DD          Diastereomer LD -continued
SCHEME II
ROUTE B

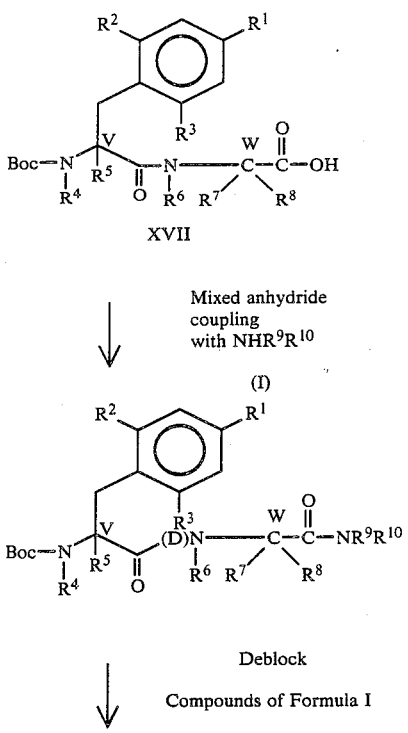

The analgesic activity for the compounds of the present invention is illustrated by their activity in the following tests. In some cases the analgesic activity of the representative compounds was compared with that of a disclosed analog of enkephalin, tyrosine-(D)-alanine-phenylpropylamide.

Writhing Assay

Male Charles River albino mice (CD-1/HAM/1LR) weighing between 20 and 30 grams were used. Thirty minutes after subcutaneous or intragastric administration of the test compound (0.1 mg/10 gram body weight), 0.025% (w/v) phenylbenzoquinone was injected intraperitoneally (0.1 ml/10 gram body weight). Five minutes later, each mouse was placed in a large glass beaker and the number of writhes that occurred in the subsequent ten minutes is counted. A writhe consisted of dorsoflexion of the back, extension of the hindlimbs, and strong contraction of the abdominal musculature. The test compound was considered to have produced analgesia in a mouse if the number of writhes elicited by phenylbenzoquinone was equal to or less than one-half the median number of writhes recorded for the saline-treated group that day. The results were expressed as the number of mice (out of a possible ten) in which the test compound produced analgesia. The test compound was rated active if the number of writhes in the drug treatment group was significantly less than the number of writhes in the saline treatment group as determined by a one-way analysis of variance. If the initial test dose of 10 mg/kg inhibited writhing in greater than 6 of 10 mice, the effect of additional doses was evaluated and $ED_{50}$ value was calculated using a maximum likelihood function.

Opiate Binding Assay

The test compounds were evaluated for their ability to displace the binding of $^3$H-Naloxone to opiate receptors isolated from rat brain. Male rats [Crl: CD(SD)BR] obtained from Charles River Laboratories (Portage, MI) were sacrificed by cervical dislocation. A purified homogenate of receptor membranes were prepared from the brains according to the method described by Chang and Cuatrecasas. (K.-J. Chang and P. Cuatrecasas. Multiple Opiate Receptors: Enkephalins And Morphine Bind To Receptors Of Different Specifity. *J. Biol. Chem.* 254, 2610–2618 (1979).) The brains were homogenized in 10 volumes of 0.32M sucrose and centrifuged twice at 6,000×g for 15 minutes. Following centrifugation of the supernatants at 40,000×g for 30 minutes, the pellets were resuspended in 5 mM tris HCl, and centrifuged at 6,000. The supernatant was centrifuged at 40,000×g. The resuspension in 5 mM tris and centrifugation was repeated twice. The final pellet was resuspended in 2 volumes of 50 mM tris HCl (pH 7.4). The homogenate was assayed for protein content according to the method of Itzhaki and Gill (R. F. Itzhaki and D. M. Gill. A Micro-Biuret Method for Estimating Proteins. *Anal. Biochem.* 9, 401–410 (1964).)

The binding of the test compounds to the receptor membrane preparation was measured using a modification of the method of Pert and Snyder (C. B. Pert and S. H. Snyder. Properties of Opiate-Receptor Binding in Rat Brain. *Proc. Natl. Acad. Sci.* 70, 2243–2247 (1973).) The receptor assay was run using a final concentration of 1 nM $^3$H-Naloxone and 0.5 mg/ml of homogenate protein. Levorphanol ($1 \times 10^{-5}$M) was used as the displacer for non-specific binding. The final concentration of the test compounds was $10^{-5}$M. The assay was run in 0.05M tris HCl (pH 7.4). Total assay volume was 1.0 ml.

Samples were incubated at 25° C. for 60 min., filtered over Whatman GF/C glass fiber filters and rinsed twice with with 2.4 ml washes of ice-cold buffer. The filters were air dried at 50° C. for 30 min. After drying, 10 ml. of PCS was added to the vial and radioactivity determined using a Tracor Analytic Mark III liquid scintillation counter with a counting efficiency of 48%.

The $IC_{50}$ values, the concentration of the test compounds which inhibited $^3$H-Naloxone specific binding to the opiate receptor by 50%, were obtained from log-logit plots of concentration-response curves.

The compounds can be administered in such oral dosage forms as tablets, capsules, pills, powders, granules, suspensions, or solutions. They may also be administered rectally or vaginally, in such forms as suppositories or bougies. They may also be introduced in the form of eyedrops, intraperitoneally, subcutaneously or intramuscularly, using forms known to the pharmaceutical art. In general the preferred form of administration is oral.

An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration of the particular compound employed. An ordinary skilled physician or verterinarian will readily determine and prescribe the effective amount based on the route of administration of the analgesic agent to prevent or arrest the progress of the condition. In so proceeding, the physician or veterinarian could employ relatively low dosages at first, subsequently increasing the dose until a maximum response is obtained.

The compounds of Formula 1 can also be administered as pharmaceutically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention may be prepared by any number of methods known to those skilled in the art. For example, the particular sequence of reactions by which the individual amino acids are joined to form the compounds of Formula I is generally not of critical importance, being chosen principally for convenience or for maximum yields. Moreover, the choice of activating reagents and conditions for joining amino acids or small peptides is not limited to those specifically described herein. Peptide intermediates and products of this invention are typically purified by crystallization, where possible, or by column chromatography. Furthermore, where racemic amino acid starting materials are employed, intermediates and products may be separated during column chromatography into diastereomers. The accompanying examples illustrate two of the possible methods used to prepare the compounds of this invention.

ROUTE A

EXAMPLE 1 methyl 6-[[2R-[[(1,1-dimethylethoxy)carbonyl]amino]-1-oxopropyl]amino]hexanoate

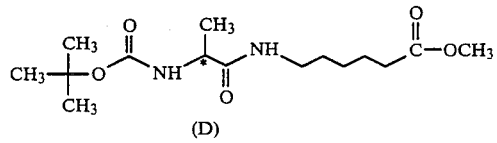

(Boc = t-butoxycarbonyl)

Boc—(D)Ala—NH(CH₂)₅CO₂Me

Boc-(D)-alanine (5.1 g, 26.9 mmol) in 100 ml of methylene chloride (CH₂Cl₂) was cooled to 0° C. and 5.9 ml (53.8 mmol) of N-methylmorpholine (NMM) were added. After cooling this vigorously stirred solution to −78° C., 3.5 ml (26.9 mmol) of isobutylchloroformate (IBCF) were added to this reaction which was run entirely under an Ar atmosphere. The mixture was allowed to warm slowly to 20° before it was again cooled to −78° C. and 4.9 g (26.9 mmol) of 6-aminohexanoic acid methylester hydrochloride were added to a single portion. Following warming this mixture to room temperature, it was allowed to stir 25 hour (h). Precipitated N-methylmorpholine hydrochloride was filtered off and the filtrate, after diluting with CH₂Cl₂ (200 ml), was washed 3×100 ml of 0.5N potassium bisulfate (KHSO₄). The combined aqueous washes were extracted with a 100 ml portion of CH₂Cl₂ and the combined organics were washed 1×75 ml of brine, dried over Na₂SO₄ (anhy.), and stripped of all solvent under reduced pressure. By thin layer chromatography (10% ethanol (EtOH)/chloroform (CHCl₃)) the yellow liquid title product was essentially one spot and used in subsequent reactions without further purification.

Optical rotation $[\alpha]_D$ +21.5° and +93.7° (365 nm) CHCl₃.

NMR shift of the (D)Ala methyl=1.34 δ (CDCl₃).

Analysis Calcd. for $C_{15}H_{28}N_2O_5 \cdot \frac{1}{2}H_2O$ (MW=325.410): C, 55.36; H, 8.98; N, 8.61. Found: C, 55.82; H, 8.50; N, 8.12.

EXAMPLE 2 methyl 6-[(2R-amino-1-oxopropyl)amino]hexanoate, monohydrochloride

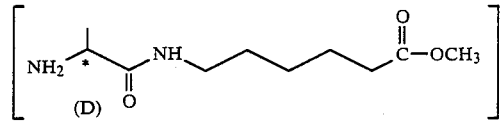

(D)Ala—NH(CH₂)₅CO₂Me.HCl

The product of Example 1 (8.0 g, 25 mmol) was dissolved in 100 ml of acetic acid (HOAc). To this solution was added 40 ml (250 mmol) of 6.2N HCl/dioxane. This solution was then gently stirred under a nitrogen (N₂) atmosphere and at room temperature for 1 h before all solvent was removed under reduced pressure. The resulting colorless oil residue was washed liberally with diethylether (Et₂O) before being dried under vacuum to yield 7.1 g of the title product. This material was used in subsequent experiments without further purification.

Optical rotation $[\alpha]_D$ −1.8°, −14.2° (365) MeOH.

NMR shift of the (D)Ala methyl=1.49δ (CD₃OD).

Analysis Calcd. for $C_{10}H_{21}N_2O_3Cl \cdot \frac{3}{4}H_2O$ (MW=266.26): C, 45.11; H, 8.52; N, 10.52. Found: C, 45.04; H, 8.56; N, 10.00.

EXAMPLE 3

N-[(1,1-dimethylethoxy)carbonyl]-2,6-dimethyl-O-[(2-methylpropoxy)carbonyl]-DL-tyrosyl-N-(6-methoxy-6-oxohexyl)-D-alaninamide

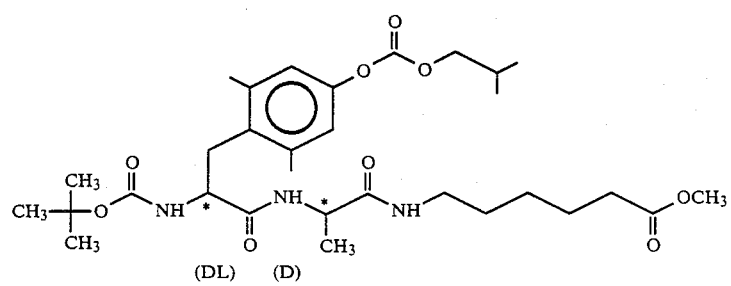

(CO₂iBu = IBC)

-continued (Boc—(DL)2,6-Me$_2$Tyr(IBC)—(D)Ala—NH(CH$_2$)$_5$CO$_2$Me)

Racemic t-butoxycarbonyl-2,6-dimethyltyrosine (4.0 g, 12.9 mmol) in 60 ml of CH$_2$Cl$_2$ was cooled to 0° C. before NMM (4.3 ml, 38.8 mmol) was added in one portion. After cooling the vigorously stirred mixture, maintained under an Ar atmosphere, to −78° C., 3.4 ml (25.8 mmol) of IBCF was added. The reaction was warmed slowly to room temperature and then recooled to −78° C. To this mixture was added 3.7 g (12.9 mmol) of the title material of Example 2. The heterogeneous reaction was again allowed to warm slowly to room temperature and stir at this temperature for 18 h. After the reaction mixture was worked up as described in Example 1, the resulting 8 g of product solid was chromatographed on a Waters Prep 500 using a 50×300 mm Porasil column eluting with 2% EtOH/CH$_2$Cl$_2$. By this procedure the two diastereomers of the title material were isolated. The diastereomer which possesses a NMR chemical shift for its (D)Ala methyl doublet upfield from its companion diastereomer was labeled UF- (up-field, smaller number). The other diastereomer having the down-field NMR chemical shift for its (D)Ala methyl was labeled DF (down-field, larger number). This nomenclature is used throughout the examples.

Diastereomer UF (2.46 g) [α]$_D$ +29.7°; +35.1° (365) CDHCl$_3$.

NMR shift of the (D)Ala methyl=1.08δ (CD$_2$Cl$_2$).

Analysis Calcd. for C$_{31}$H$_{49}$N$_3$O$_9$ (MW=607.62): C, 61.27; H, 8.13; N, 6.91. Found: C, 61.52; H, 8.25; N, 6.93.

Diastereomer DF (2.22 g) [α]$_D$ 0.0°; +8.3° (365) CHCl$_3$.

NMR shift of the (D)Ala methyl=1.31δ (CD$_2$Cl$_2$).

Analysis Calcd. for C$_{31}$H$_{49}$N$_3$O$_9$ (MW=607.62): C, 61.27 H, 8.13; N, 6.91. Found: C, 61.50; H, 8.16; N, 6.87.

EXAMPLE 4

N-[(1,1-dimethylethoxy)carbonyl]-2,6-dimethyltyrosyl)-N-(6-methoxy-6-oxohexyl)-D-alaninamide UF isomer

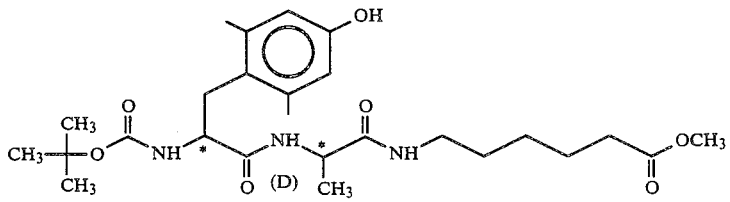

(Boc—2,6-Me$_2$Tyr—(D)Ala—NH(CH$_2$)$_5$CO$_2$Me)

The UF diastereomer (δ=1.08, NMR chemical shift of the (D) alanine methyl) of Example 3 (2.37 g, 3.9 mmol) was dissolved in 40 ml of methanol (MeOH). To this solution was added 590 mg (4.3 mmol) of potassium carbonate (K$_2$CO$_3$). The reaction vessel containing this mixture was flushed with Ar, stoppered, and stirred for 1 h before TLC (5% EtOH/CHCl$_3$) indicated that the reaction was complete. After diluting this mixture with 300 ml of CH$_2$Cl$_2$ and adding 100 ml of 0.5N KHSO$_4$ the mixture was stirred for 14 h. The organic layer was separated and washed 2×100 ml of 0.5N KHSO$_4$. The combined aqueous layers were then extracted 1×75 ml of CH$_2$Cl$_2$ before the combined organics were washed 1×100 ml of brine, dried (Na$_2$SO$_4$), and stripped of all solvent under reduced pressure. The resulting white glass was washed extensively with hexanes (SKB) and Et$_2$O combinations and dried under vacuum to give the analytically pure title product (2.0 g).

Optical rotation [α]$_D$=+47.2°; +186.0° (365) CHCl$_3$.

NMR shift of the (D)Ala methyl=1.08δ (CD$_2$Cl$_2$).

Analysis Calcd. for C$_{26}$H$_{41}$N$_3$O$_7$·½H$_2$O (MW=516.15): C, 60.44; H, 8.19; N, 8.13. Found: C, 60.76; H, 8.13; N, 7.93.

EXAMPLE 5

2,6-dimethyltyrosyl-N-(6-methoxy-6-oxohexyl)-D-alaninamide, monohydrochloride

DF isomer

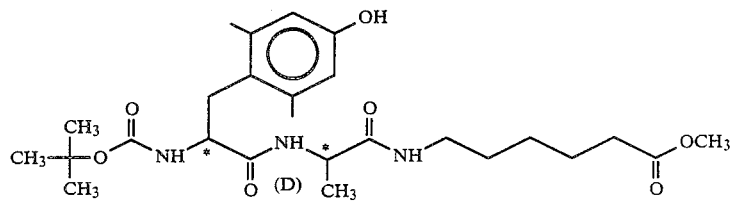

(Boc—2,6-Me$_2$Tyr—(D)Ala—NH(CH$_2$)$_5$CO$_2$Me)

Using the method of Example 4, 2.05 g (3.37 mmol) of the S-diastereomer of Example 3 was converted to the 1.73 g of the title product.

Optical rotation [α]$_D$−12.0°; −21.2° (365) CHCl$_3$.

NMR shift of the (D)Ala methyl=1.27δ (CD$_2$Cl$_2$).

Analysis Calcd. for C$_{26}$H$_{41}$N$_3$O$_7$·½H$_2$O (MW=516.65): C, 60.44; H, 8.19; N, 8.13. Found: C, 60.72; H, 8.06; N, 8.00.

EXAMPLE 6

2,6-dimethyltyrosyl-N-(6-methoxy-6-oxohexyl)-D-alaninamide, monohydrochloride

UF isomer

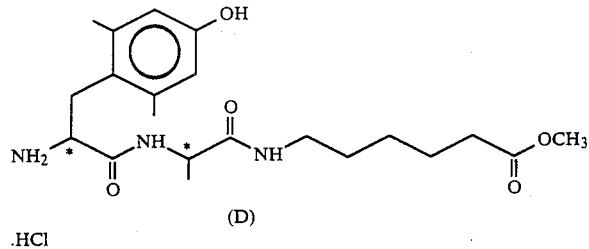

(2,6Me₂Tyr—(D)Ala—NH(CH₂)₅CO₂Me.HCl)

The product of Example 4 (1.80 g, 3.48 mmol) was dissolved in 25 ml of acetic acid (HOAc). To this solution stirred gently at room temperature under a nitrogen (N₂) atmosphere was added 6 ml of 6N HCl/dioxane. After one hour all the solvent was removed under reduced pressure and the resulting pale yellow oil was shaken with Et₂O to produce the white solid product salt. This material was suctioned filtered, washed with Et₂O and dried under vacuum to yield 1.6 g of the title compound.

Optical rotation $[\alpha]_D +106.3°$; +420.5° (365) MeOH.
NMR shift of the (D)Ala methyl = 1.03δ (CD₃OD).
Analysis calcd. for C₂₁H₃₄N₃O₅Cl.½H₂O (MW=452.98); C, 55.68; H, 7.79; N, 9.28. Found: C, 55.76; H, 7.69; N, 9.26.

EXAMPLE 7

2,6-dimethyltyrosyl-N-(6-methoxy-6-oxohexyl)-D-alaninamide, monohydrochloride

DF isomer

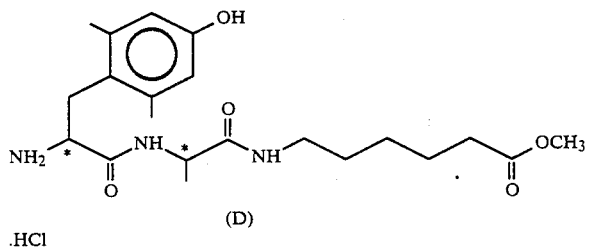

(2,6-Me₂Tyr—(D)Ala—NH(CH₂)₅CO₂Me.HCl)

The title material of Example 5 was deblocked by the method of Example 6.

Optical rotation $[\alpha]_D -67.0°$; -238.3° (365) MeOH.
NMR shift of the (D)Ala methyl = 1.28δ (CD₃OD).
Analysis Calcd. for C₂₁H₃₄N₃O₅Cl.½H₂O (MW=452.98): C, 55.68; H, 7.79; N, 9.28. Found: C, 55.33; H, 7.51; N, 9.26.

EXAMPLE 8 phenylmethyl[1R-methyl-2-oxo-2-[(tricyclo[3.3.1.1³,⁷]-dec-2-yl)amino]ethyl]carbamate

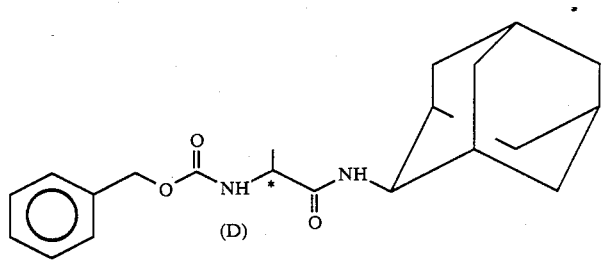

(Z—(D)Ala—NH2Ad)

The title compound was prepared by the methods of Example 1 where Z-(D)Alanine (10.0 g, 44.8 mmol) was used in place of Boc-(D)Alanine and H₂N2Ad.HCl (8.4$_S$, 44.8 mmol) was used in place of NH₂(CH₂)₅CO₂Me.HCl. After workup, 17.3 g of the yellow viscous oil product was obtained and used in subsequent examples without further purification.

Optical rotation $[\alpha]_D +18.9°$; +68.7° (589) CHCl₃.
NMR shift of the (D)Ala methyl = 1.33δ (CD₂Cl₂).
Analysis Calcd. for C₂₁H₂₈N₂O₃.½H₂O (MW=365.48): C, 69.01; H, 8.00; N, 7.66. Found: C, 68.57; H, 7.93; N, 7.06.

EXAMPLE 9

2R-amino-N-(tricyclo[3.3.1.1³,⁷]dec-2-yl)propanamide

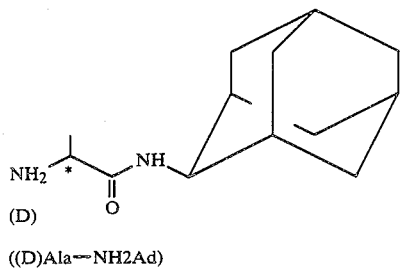

((D)Ala—NH2Ad)

The product of Example 8 above (15.8 g, 43.2 mmol) was hydrogenated in 125 ml of methanol (MeOH) over Pd black catalyst. The hydrogenation was carried out in a Parr Apparatus at room temperature under $H_2$ at 60 psi. There was a theoretical uptake of $H_2$ over a 6 hour period. The catalyst was filtered from the solution and all solvent was removed under reduced pressure to provide 7.32 g of the white solid product after washing with $Et_2O$ and drying under vacuum.

Optical rotation $[\alpha]_D$ −0.8°; 1.6° (365) $CHCl_3$.
NMR shift of the (D)Ala methyl=1.34δ ($CDCl_3$).
Analysis calcd. for $C_{13}H_{22}N_2O \cdot \frac{1}{4}H_2O$ (MW=226.84): C, 68.80; H, 10.00; N, 12.35. Found: C, 68.50; H, 9.86; N, 12.55.

EXAMPLE 10

Mix of Diastereomers

N-[(1,1-dimethylethoxy)carbonyl]-2,6-dimethyl-O-[(2-methylpropoxy)carbonyl]-DL-tyrosyl-N-(tricyclo[3.3.1.1³,⁷]dec-2-yl)-D-alaninamide

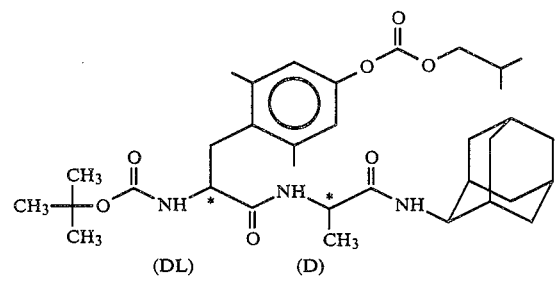

(Boc—(DL)2,6Me₂Tyr(IBC)—(D)Ala—NH2Ad)

The title mixture of diastereomers (iso-UF & DF) was prepared as described in Example 3 using the title material of Example 9 (1.5 g, 6.5 mmol) in place of that from Example 2. Both title diastereomers were separated by pressure liquid chromatography (PLC) on Merck silica eluting with 10% ethyl acetate (EtOAc)/$CH_2Cl_2$.

Diastereomer UF (1.54 g) $[\alpha]_D$ +35.2°; +145.7° (365) $CHCl_3$.
NMR shift of the (D)Ala methyl=1.08δ ($CD_2Cl_2$).
Analysis Calcd. for $C_{34}H_{51}N_3O_7$ (MW=613.81): C, 66.53; H, 8.37; N, 6.85. Found: C, 66.22; H, 8.44; N, 6.91.

Diastereomer DF (1.28 g) $[\alpha]_D$ +16.5°, +68.4° (365) $CHCl_3$.
NMR shift of the (D)Ala methyl=1.33δ ($CD_2Cl_2$).
Analysis Calcd. for $C_{34}H_{51}N_3O_7$ (MW=613.81): C, 66.53; H, 8.37; N, 6.85. Found: C, 66.56; H, 8.36; N, 6.63.

EXAMPLE 11

N-[(1,1-dimethylethoxy)carbonyl]-2,6-dimethyltyrosyl-N-(tricyclo[3.3.1.1³,⁷]dec-2-yl)-D-alaninamide UF isomer

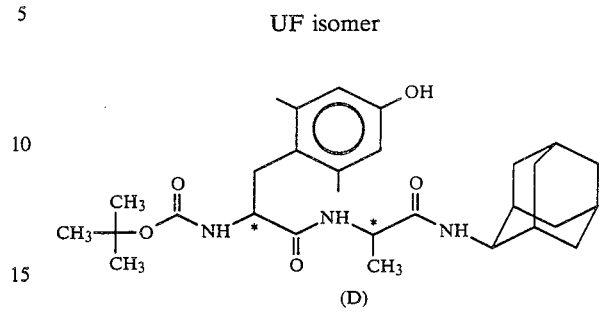

(Boc—2,6Me₂Tyr—(D)Ala—NH2Ad)

The title compound was prepared by the method of Example 4 using the UF diastereomer of Example 10 in place of the UF diastereomer of Example 3.

Optical rotation $[\alpha]_D$ +32.6°; +179.5° (365) $CHCl_3$.
NMR shift of the (D)Ala methyl=1.04δ ($CD_2Cl_2$).
Analysis Calcd. for $C_{29}H_{43}N_3O_5 \cdot \frac{1}{2}H_2O$ (MW=523.70): C, 66.63; H, 8.48; N, 8.04. Found: C, 66.63; H, 8.29; N, 7.85.

EXAMPLE 12

N-[(1,1-dimethylethoxy)carbonyl]-2,6-dimethyltyrosyl-N-(tricyclo[3.3.1.1³,⁷]dec-2-yl)-D-alaninamide DF isomer

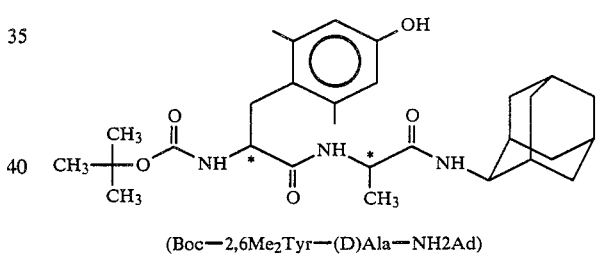

(Boc—2,6Me₂Tyr—(D)Ala—NH2Ad)

The title compound was prepared by the method of Example 4 using the DF diastereomer of Example 10 in place of the UF diastereomer of Example 3.

Optical rotation $[\alpha]_D$ +23.3°; +83.6° (365) $CHCl_3$.
NMR shift of the (D)Ala methyl=1.32δ ($CD_2Cl_2$).
Analysis Calcd. for $C_{29}H_{43}N_3O_5 \cdot H_2O$ (MW=531.71): C, 65.50; H, 8.53; N, 7.90. Found: C, 65.58; H, 8.13; N, 7.80.

EXAMPLE 13

2,6-dimethyltyrosyl-N-(tricyclo[3.3.1.1³,⁷]dec-2-yl)-D-alaninamide, monohydrochloride UF isomer

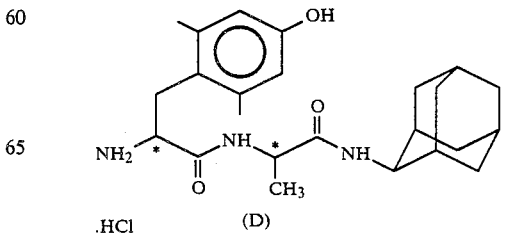

-continued (2,6Me2Tyr—(D)Ala—NH2Ad.HCl)

The title material of Example 11 was deblocked by the method of Example 6.

Optical rotation $[\alpha]_D+111.2°$; $+418.5°$ (365) MeOH.
NMR shift of the (D)Ala methyl=1.03δ (CD3OD).
Analysis Calcd. for $C_{24}H_{36}N_3O_3Cl\cdot\frac{1}{2}H_2O$ (MW=459.04): C, 62.80; H, 8.12; N, 9.15. Found: C, 62.99; H, 8.00; N, 8.94.

EXAMPLE 14

2,6-dimethyltyrosyl-N-(tricyclo[3.3.1.13,7]dec-2-yl)-D-alaninamide, monohydrochloride DF isomer

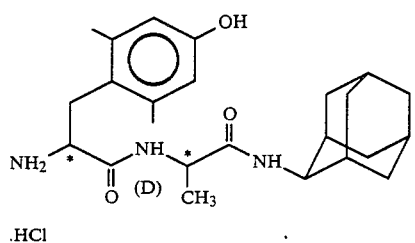

The title material of Example 12 was converted to the title HCl salt by the method of Example 6.

Optical rotation $[\alpha]_D-55.5°$; $-233.6°$ (365) MeOH.
NMR shift of the (D)Ala methyl=1.28δ (CD3OD).
Analysis Calcd. for $C_{24}H_{36}N_3O_3Cl\cdot\frac{1}{4}H_2O$ (MW=454.53): C, 63.42; H, 8.09; N, 9.25. Found: C, 63.48; H, 8.12; N, 9.12.

ROUTE B

EXAMPLE 15

N-[(1,1-dimethylethoxy)carbonyl]-2,6-dimethyl-DL-tyrosyl-D-alanine, methyl ester

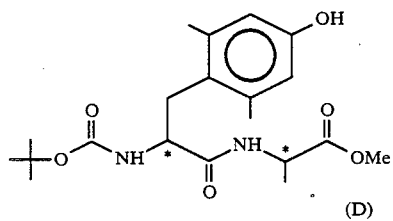

(Boc—(DL)2,6Me2Tyr—(D)Ala—OMe)

Racemic t-butoxycarbonyl 2,6-dimethyltyrosine (3.9 g, 10 mmol) was dissolved in 30 ml of CH2Cl2 by adding 1.12 ml (10 mmol) of NMM. After bringing this mixture to reflux it was cooled to −30° C. and 1.32 ml (10 mmol) of IBCF were added to this stirred solution. The temperature was allowed to rise to −15° C. and then lowered to −50° C. (D)alanine methyl ester hydrochloride (1.54 g, 11 mmol) was added to the solution followed by 1.3 ml (11 mmol) of NMM. The mixture was allowed to warm to room temperature and stand for 16 h. The majority of the CH2Cl2 was removed under reduced pressure. Ethyl acetate (EtOAc, 200 ml) was added and this solution was washed twice with 100 ml portions of 0.5 molar KHSO4, once with 100 ml of H2O and dried over MgSO4. Removal of all solvent gave 3.9 g of the mixture of diastereomers. Recrystallization of this material from Skelly B(hexanes)/CH2Cl2 produced 1.6 g (4.2 mmol) of diastereomer F. Removal of the solvent from the filtrate gave 1.3 g (3.3 mmol) of diastereomer S contaminated by less than 10% of diastereomer DF. The mixture of diastereomers or either of the separated diastereomers were used in subsequent examples without further purification.

Diastereomer DF:
NMR shift of the (D)Ala methyl=1.33δ (CD2Cl2).
Diastereomer UF: NMR shift of the (D)Ala methyl=1.16δ (CD2Cl2).

EXAMPLE 16

N-[(1,1-dimethylethoxy)carbonyl]-2,6-dimethyl-tyrosyl-D-alanine (UF isomer)

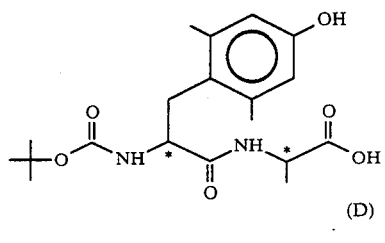

(Boc—2,6Me2Tyr—(D)Ala)

A 13.0 g (33 mmol) sample of the title compound of Example 15 or its UF diastereomer was dissolved in 50 ml of MeOH. To this was added 50 ml of 1N NaOH. The mixture was stirred for 16 hours, acidified with 0.5N KHSO4 to pH2 and extracted with EtOAc. The organic layer was washed with brine, dried over MgSO4, and concentrated to produce 12 g (95%) of the product as a foam.

Diastereomer UF $[\alpha]_D+16.5°$ (CHCl3).
NMR shift of the (D)Ala methyl=1.26δ (CD2Cl2).
Analysis Calcd. for $C_{19}H_{28}N_2O_6$ (MW=380.44): C, 59.99; H, 7.42; N, 7.36. Found: C, 59.19; H, 7.44; N, 7.17.

EXAMPLE 17

N-[(1,1-dimethylethoxy)carbonyl]-2,6-dimethyl-tyrosyl-D-alanine (DF isomer)

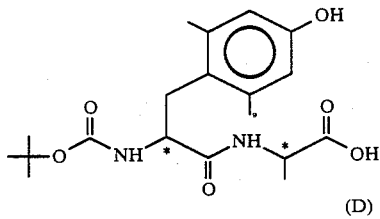

(Boc—2,6Me2Tyr—(D)Ala)

The title compound was prepared by the methods of Example 16 using diastereomer DF of the title compound of Example 15.

Diastereomer DF $[\alpha]_D-21.7°$ (CHCl3).
NMR shift of the (D)Ala methyl=1.26δ (CD2Cl2).

EXAMPLE 18

N-[(1,1-dimethylethoxy)carbonyl]-2,6-dimethyl-DL-tyrosyl-N-(2,3-dihydro-1H-inden-1-yl)-D-alaninamide

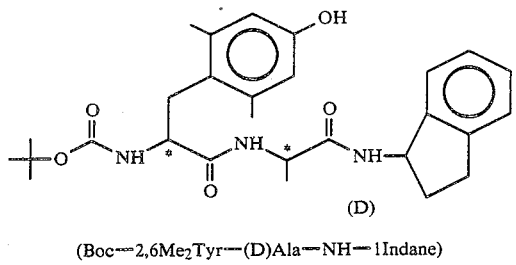

(Boc—2,6Me₂Tyr—(D)Ala—NH—1Indane)

The title material from Example 16 (1.5 g, 3.9 mmol) was dissolved in 20 ml of CH₂Cl₂. To this solution, gently stirred under an Ar atmosphere and cooled to −20° C., was added 0.40 g (3.9 mmol) of NMM followed by 0.54 g (3.9 mmol) of IBCF. After allowing the temperature of this mixture to come to 0° C., it was recooled to −10° and 0.53 g (3.9 mmol) of 1-amino indane were added. The reaction was warmed to room temperature and worked up as described in Example 1. The crude product was chromatographed (PLC) on silica gel eluting with 2%–5% MeOH/CHCl₃ to obtain the white solid title compound (1.3 g) as a mixture of diastereomers.

Analysis Calcd. for $C_{28}H_{37}N_3O_6$ (MW=511.62): C, 65.73; H, 7.24; N, 8.21. Found: C, 65.36; H, 7.19; N, 8.01.

EXAMPLE 19

2,6-dimethyl-DL-tyrosyl-N-(2,3-dihydro-1H-inden-1-yl)-D-alaninamide, monohydrochloride

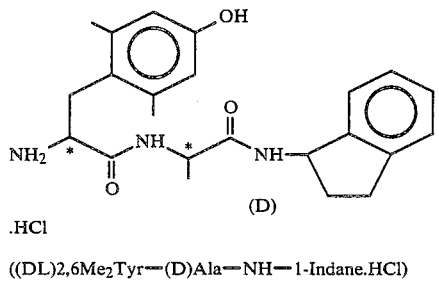

((DL)2,6Me₂Tyr—(D)Ala—NH—1-Indane.HCl)

The title compound of Example 18 was deblocked and converted to its HCl salt by the method of Example 6.

Analysis Calcd. for $C_{23}H_{30}N_3O_3Cl.\frac{1}{2}H_2O$ (MW=440.97): Calc.: C, 62.64; H, 7.10; N, 9.53; Cl, 8.04. Found: C, 62.61; H, 7.09; N, 9.09; Cl, 7.70.

ROUTE A

EXAMPLE 20 phenylmethyl [2-[(2,3-dihydro-1H-inden-2-yl)amino]-1R-methyl-2-oxoethyl]carbamate

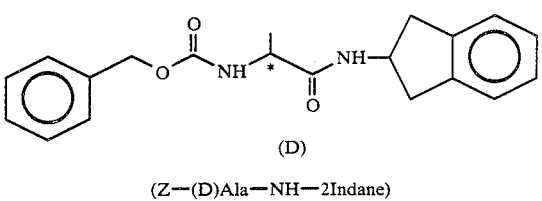

(Z—(D)Ala—NH—2Indane)

The title compound was prepared from Z-(D)Alanine (10 g, 44.8 mmol) and 2-amino indane hydrochloride (7.6 g, 44.8 mmol) by the method of Example 8. After workup, the crude solid was washed liberally with Et₂O to give 12.35 g of the white solid title material.

Optical rotation [α]$_D$ +3.0°; +0.5° (365) CHCl₃.

NMR shift of (D)Ala methyl = 1.28δ (CD₂Cl₂).

Analysis Calcd. for $C_{20}H_{22}N_2O_5$ (MW=338.41): C, 70.99; H, 6.55; N, 8.28. Found: C, 71.10; H, 6.50; N, 8.27.

EXAMPLE 21

2R-amino-N-(2,3-dihydro-1H-inden-2-yl)propanamide

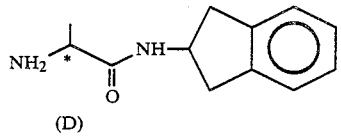

((D)Ala—NH—2Indane)

The title material was prepared from the title material of Example 20 by the method of Example 9.

Optical rotation [α]$_D$ +21.6°; +68.6° (365) CHCl₃.

NMR shift of the (D)Ala methyl = 1.23δ (CD₂Cl₂).

Analysis Calcd. for $C_{12}H_{16}N_2O$ (MW=204.16): C, 70.56; H, 7.89; N, 13.71. Found: C, 70.40; H, 7.94; N, 13.67.

EXAMPLE 22

N-[(1,1-dimethylethoxy)carbonyl]-2,6-dimethyl-O-[(2-methylpropoxy)carbonyl]-DL-tyrosyl-N-(2,3-dihydro-1H-inden-2-yl)-D-alaninamide

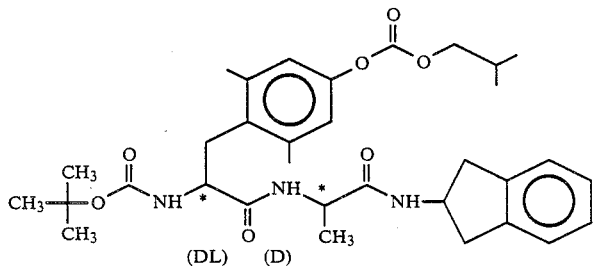

(Boc—(DL)2, 6Me₂Tyr(IBC)—(D)Ala—NH—2Indane)

The title mixture of diastereomers was prepared as described in Example 3 using the title material of Example 21 in place of that from Example 2. Only the DF-diastereomer was isolated pure by PLC on Woelm® silica eluting with 2% EtOH/CHCl₃.

Diastereomer S $[\alpha]_D$ +6.6°; +13.3° (365) CHCl₃.
NMR shift of the (D)Ala methyl=1.29δ (CD₂Cl₂).
Analysis Calcd for C₃₃H₄₄N₃O₇ (MW=594.74): C, 66.64; H, 7.46; N, 7.07. Found: C, 66.48; H, 7.43; N, 6.93.

EXAMPLE 23

N-[(1,1-dimethylethoxy)carbonyl]-2,6-dimethyltyrosyl-N-(2,3-dihydro-1H-inden-2-yl)-D-alaninamide DF isomer

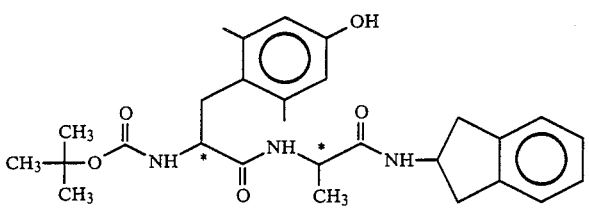

(Boc—2, 6Me₂Tyr—(D)Ala—NH—2Indane)

The title compound was prepared by the method of Example 4 using the title compound of Example 22 in place of the UF diastereomer of Example 3.

Optical rotation $[\alpha]_D$ +7.5°; +40.4° (365) CHCl₃.
NMR shift of the (D)Ala methyl=1.28δ (CD₂Cl₂).
Analysis Calcd. for C₂₈H₃₇N₃O₅ (MW=495.62): C, 67.85; H, 7.52; H, 8.48. Found: C, 67.56; H, 7.49; N, 8.19.

EXAMPLE 24

2,6-dimethyltyrosyl-N-(2,3-dihydro-1H-inden-2-yl)-D-alaninamide, monohydrochloride DF isomer

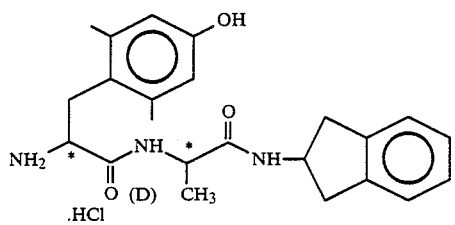

(2, 6Me₂Tyr—(D)Ala—NH—2Indane.HCl)

The title material was prepared by deblocking the title compound of Example 23 using the methods of Example 6.

Optical rotation $[\alpha]_D$ −82.6°; −300.0° (365) MeOH.
NMR shift of the (D)Ala methyl=1.27δ (CD₃OD).
Analysis Calcd. for C₂₃H₃₀N₃O₃Cl.¾H₂O (MW=445.48): C, 62.01; H, 7.13; N, 9.43; Cl, 7.87. Found: C, 62.05; H, 6.91; N, 9.28; Cl, 8.21.

EXAMPLE 25 phenylmethyl [1R-methyl-2-oxo-2-(1,2,3,4-tetrahydro-1-quinolinyl)ethyl]carbamate

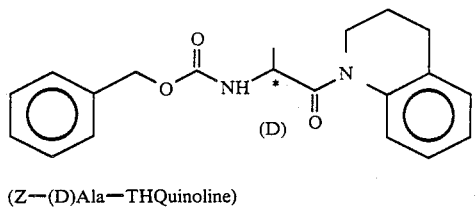

(Z—(D)Ala—THQuinoline)

The title compound was prepared from Z-(D)Alanine and 1,2,3,4-tetrahydroquinoline by the method of Example 8. After workup, the crude pale yellow oil product was used in subsequent reactions without further purification.

NMR shift of the (D)Ala methyl=1.16δ (CD₂Cl₂).

EXAMPLE 26

1-(2R-amino-1-oxopropyl)-1,2,3,4-tetrahydro-quinoline, monohydrochloride

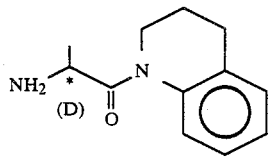

((D)Ala—THQuinoline.HCl)

The free base of the title material was prepared from the title material of Example 25 (11.4 g, 34.0 mmol) by the method of Example 9. This material was then dissolved in 300 ml of Et₂O and treated with 12 ml of 6.2N HCl/dioxane. The precipitated white solid title salt was suction filtered, washed with Et₂O, and vacuum dried (7.47 g).

Optical rotation $[\alpha]_D$ −87.7°; −519.6° (365) MeOH.
NMR shift of the (D)Ala methyl=1.30δ (CD₃OD).
Analysis Calcd. for C₁₂H₁₇N₂OCl (MW=240.73): C, 59.87; H, 7.12; N, 11.64. Found: C, 59.84; H, 7.13; N, 11.60.

EXAMPLE 27

4-[2-[[(1,1-dimethylethoxy)carbonyl]amino]-3-[[1R-methyl-2-oxo-2-(1,2,3,4-tetrahydro-1-quinolinyl)ethyl]amino]-3-oxopropyl]-3,5-dimethylphenyl 2-methylpropane carbonate

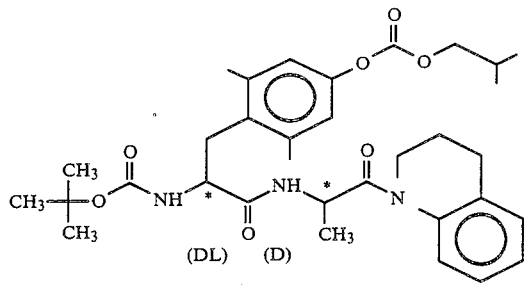

(Boc—(DL)2, 6Me₂Tyr(IBC)—(D)Ala—THQuinoline)

The title mixture of diastereomers was prepared as described in Example 3 using the title material of Example 26 in place of Example 2 material. The unseparated diastereomers were isolated by LPC and used within further purification.

EXAMPLE 28

α-[[(1,1-dimethylethoxy)carbonyl]amino]-4-hydroxy-2,6-dimethyl-N-[1R-methyl-2-oxo-2-(1,2,3,4-tetrahydro-1-quinolinyl)ethyl]benzenepropanamide

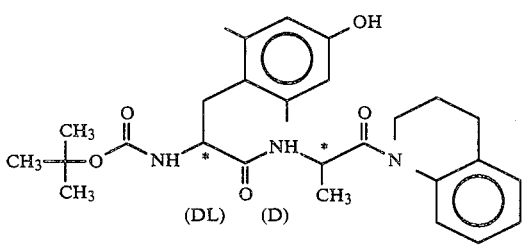

(Boc—(DL)2, 6Me₂Tyr—(D)Ala—THQuinoline)

The title mixture of diastereomers was prepared by the method of Example 4 using the title mixture of Example 27 in place of the F diastereomer of Example 3. Both diastereomers were separated on a Waters Prep 500 with a $C_{18}$ reverse phase cartridge eluting with 30% acetonitrile/water.

Diastereomer DF: [α] −67.3°; −354.0° (365) CHCl₃.
Analysis Calcd. for $C_{28}H_{37}N_3O_5 \cdot \frac{1}{2}H_2O$ (MW=504.64): C, 66.64; H, 7.59; N, 8.33. Found: C, 66.40; H, 7.41; N, 7.94.

Diastereomer UF [α]$_D$ −44.8°; −242.4° (365) MeOH.
Analysis Calcd. for $C_{28}H_{37}N_3O_5 \cdot \frac{1}{4}H_2O$ (MW=500.14): C, 67.24; H, 7.56; N, 8.40. Found: C, 67.52; H, 7.55; N, 7.95.

EXAMPLE 29

αS-R*-amino-4-hydroxy-2,6-dimethyl-N-[1S*-methyl-2-oxo-2-(1,2,3,4-tetrahydro-1-quinolinyl)ethyl]benzenepropanamide, monohydrochloride DF isomer

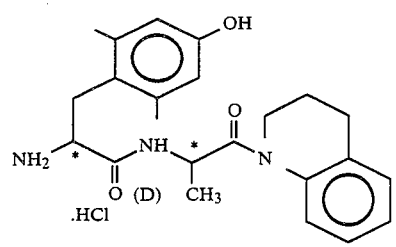

(2, 6Me₂Tyr—(D)Ala—THQuinoline.HCl)

The title material was prepared from the F diastereomer (rev. phase) of Example 28 by the method of Example 6.

Optical rotation [α$_D$ −97.4°; −418.8° (365) MeOH.
NMR Shift of the (D)Ala methyl=1.20δ (CD₃OD).
Analysis Calcd. for $C_{23}H_{30}N_3O_3Cl \cdot \frac{3}{4}H_2O$ (MW=445.48): C, 62.01; H, 7.12; N, 9.43. Found: C, 62.08; H, 7.33; N, 8.51.

EXAMPLE 30

α-amino-4-hydroxy-2,6-dimethyl-N-[1R-methyl-2-oxo-2-(1,2,3,4-tetrahydro-1-quinolinyl)ethyl]benezenepropanamide, monohydrochloride UF isomer

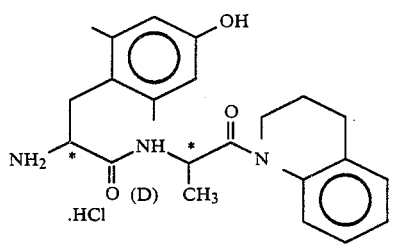

(2, 6-Me₂Tyr—(D)Ala—THQuinoline.HCl)

The title compound was prepared from the S diastereomer (rev phase) of Example 28 using the methods of Example 6.

Optical rotation [α]$_D$ +24.7°; +36.6° (365) MeOH.
NMR shift of the (D)Ala methyl=0.91δ (CD₃OD).
Analysis Calcd. for $C_{23}H_{30}N_3O_3Cl \cdot 1\frac{1}{2}H_2O$ (MW=458.99): C, 60.19; H, 7.25; N, 9.16. Found: C, 60.46; H, 7.18; N, 8.72.

EXAMPLE 31 phenylmethyl [1R-methyl-2-oxo-2-(1,2,3,4-tetrahydro-2-isoquinolinyl)ethyl]carbamate

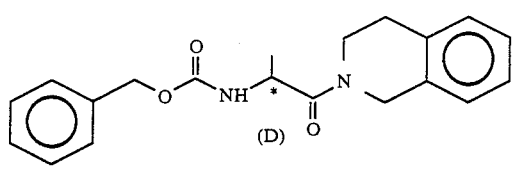

(Z—(D)Ala—THIsoquinoline)

The title material was synthesized from Z-(D)Alanine and 1,2,3,4-tetrahydroisoquinoline by the method of Example 8. Following workup, the crude product oil was purified by chromatographed on a Waters Prep 500 using a Porasil cartridge and eluting with 3–5% EtOAc/CH$_2$Cl$_2$.

Optical rotation $[\alpha]_D$ −4.3°; −20.9° (365) CHCl$_3$.
NMR shift of the (D)Ala methyl = 1.33δ (CD$_2$Cl$_2$).
Analysis Calcd. for C$_{20}$H$_{22}$N$_2$O$_3$ (MW = 338.41): C, 70.98; H, 6.55; N, 8.28. Found: C, 70.55; H, 6.61; N, 8.21.

EXAMPLE 32

2-(2R-amino-1-oxopropyl)-1,2,3,4-tetrahydroisoquinoline, monohydrochloride

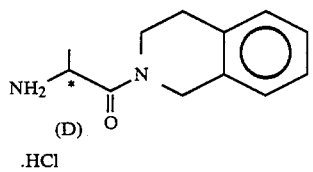

((D)Ala—THIsoquinoline.HCl)

The title compound was prepared by the method of Example 26 using the title material of Example 31 in place of that from Example 25.

Optical rotation $[\alpha]_D$ +30.3°; +88.1° (365) MeOH.
NMR shift of the (D)Ala = 1.50δ (CD$_3$OD).
Analysis Calcd. for C$_{12}$H$_{17}$N$_2$OCl.¼H$_2$O (MW = 245.24): C, 58.77; H, 7.19; N, 11.42. Found: C, 59.06; H, 6.99; N, 11.59.

EXAMPLE 33

4-[2-[[(1,1-dimethylethoxy)carbonyl]amino]-3-[[1R-methyl-2-oxo-2-(1,2,3,4-tetrahydro-2-isoquinolinyl)ethyl]amino-3-oxopropyl]-3,5-dimethylphenyl 2-methylpropane carbonate

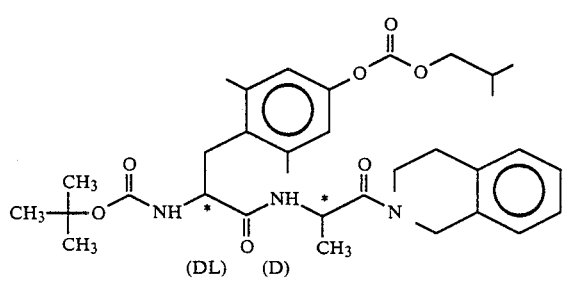

(Boc—(DL)2, 6Me$_2$Tyr(IBC)—(D)Ala—THIsoquinoline)

The title mixture of diastereomers was synthesized as described in Example 3 using the title material of Example 32 in place of that from Example 2. Both diastereomers were separated by PLC on Merck ® silica eluting with 5–7% EtOAc/CH$_2$Cl$_2$.

Diastereomer UF $[\alpha]_D$ +10.0°; +31.8° (365) CHCl$_3$.
NMR shift of the (D)Ala methyl = 1.04δ (CD$_2$Cl$_2$).
Analysis Calcd. for C$_{33}$H$_{45}$N$_3$O$_7$ (MW = 595.74): C, 66.53; H, 7.61; N, 7.05. Found: C, 66.87; H, 7.58; N, 6.73.
Diastereomer DF $[\alpha]_D$ −15.3°; −58.7° (365) CHCl$_3$.
NMR shift of the (D)Ala methyl = 1.28δ (CD$_2$Cl$_2$).
Analysis Calcd. for C$_{33}$H$_{45}$N$_3$O$_7$ (MW = 595.74): C, 66.53; H, 7.61; N, 7.05. Found: C, 66.82; H, 7.58; N, 6.76.

EXAMPLE 34

UF isomer 1,1-dimethylethyl [1-[(4-hydroxy-2,5-dimethylphenyl)methyl]-2-[[1R-methyl-2-oxo-2-(1,2,3,4-tetrahydro-2-isoquinolinyl)ethyl]amino]-2-oxoethyl]carbamate, isomer UF

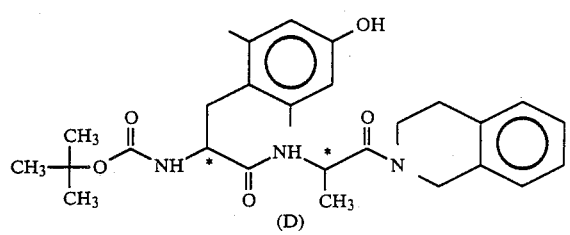

(Boc—2, 6Me$_2$Tyr—(D)Ala—THIsoquinoline)

The title compound was prepared by the method of Example 4 using the F diastereomer of Example 33 in place of the UF diastereomer of Example 3.

Optical rotation $[\alpha]$ +18.8°; +87.9° (365) CHCl$_3$.
NMR shift of the (D)Ala methyl = 1.07δ (CD$_2$Cl$_2$).
Analysis Calcd. for C$_{28}$H$_{37}$N$_3$O$_5$ (MW = 495.63): C, 67.85; H, 7.52; N, 8.48. Found: C, 67.56; H, 7.31; N, 8.44.

EXAMPLE 35

α-amino-4-hydroxy-2,6-dimethyl-N-[1R-methyl-2-oxo-2-(1,2,3,4-tetrahydro-2-isoquinolinyl)ethyl]benzenepropanamide, monohydrochloride, isomer S UF isomer

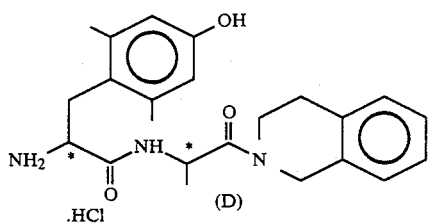

(2, 6Me$_2$Tyr—(D)Ala—THIsoquinoline.HCl)

The title compound was synthesized from the title material of Example 34 by the method of Example 6.

Optical roration $[\alpha]_D$ +125.2°; +467.0° (365) CH$_3$OH.
NMR shift of the (D)Ala methyl = 1.08δ (CD$_3$OD).

Analysis Calcd. for $C_{23}H_{30}N_3O_3Cl.\frac{1}{2}H_2O$ (MW=440.98): C, 62.64; H, 7.09; N, 9.53; Cl, 8.04. Found: C, 62.66; H, 7.42; N, 8.85; Cl, 7.82.

EXAMPLE 36

DF isomer 1,1-dimethylethyl [1-[(4-hydroxy-2,5-dimethylphenyl)methyl]-2-[[1R-methyl-2-oxo-2-(1,2,3,4-tetrahydro-2-isoquinolinyl)ethyl]amino]-2-oxoethyl]carbamate, isomer DF

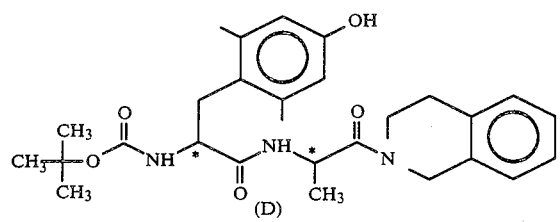

(Boc—2,6Me₂Tyr—(D)Ala—THIsoquinoline)

The title compound was prepared by the method of Example 4 using the S diastereomer of Example 33 in place of the F diastereomer of Example 3.

Optical rotation $[\alpha]_D -5.7°$; $-23.0°$ (365) CHCl₃.
NMR of the (D)Ala methyl=1.24δ (CD₂Cl₂).
Analysis Calcd. for $C_{28}H_{37}N_3O_5$ (MW=495.63): C, 67.85; H, 7.52; N, 8.48. Found: C, 67.79; H, 7.41; N, 8.40.

EXAMPLE 37

α-amino-4-hydroxy-2,6-dimethyl-N-[1R-methyl-2-oxo-2-(1,2,3,4-tetrahydro-2-isoquinolinyl)ethyl]benzenepropanamide, monohydrochloride DF isomer

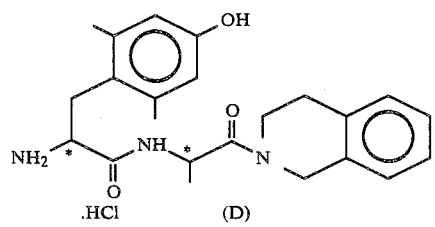

(2,6Me₂Tyr—(D)Ala—THIsoquinoline.HCl)

The title compound was synthesized from the title material of Example 36 by the method of Example 6.

Optical rotation $[\alpha]_D -72.7°$; $-281.8°$ (365) MeOH.
NMR shift of the (D)Ala methyl=1.28δ (CD₃OD).
Analylsis Calcd. for $C_{23}H_{30}N_3O_3Cl.\frac{1}{2}$ H₂O (MW=440.98): C, 62.64; H, 7.09; N, 9.53; Cl, 8.04. Found: C, 62.73; H, 7.09; N, 9.24; Cl, 8.13.

ROUTE B

EXAMPLE 38

N-[(1,1-dimethylethoxy)carbonyl]-2,6-dimethyl-L-tyrosyl-N-[2-(2-thienyl)ethyl]-D-alaninamide UF isomer

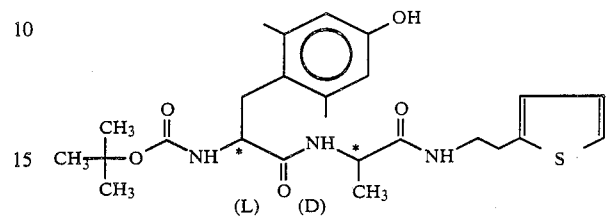

(Boc—2,6Me₂Tyr—(D)Ala—NH(CH₂)₂—2-thiophene)

The title compound was prepared by the method of Example 18 using 2-thienylethylamine in place of 1-aminoindane and purified by PLC on Merck ® silica eluting with 1–2% EtOH/CHCl₃.

Optical rotation $[\alpha]_D +38.3°$; $+157.4°$ (365) CHCl₃.
NMR shift of the (D)Ala methyl=1.04δ (CDCl₃).
Analysis Calcd. for $C_{25}H_{35}N_3O_5S$ (489.65): C, 61.33; H, 7.20; N, 8.58; S, 6.55. Found: C, 60.97; H, 7.10; N, 8.46; S, 6.38.

EXAMPLE 39

2,6-dimethyl-L-tyrosyl-N-[2-(2-thienyl)ethyl]-D-alainamide, monohydrochloride

UF isomer

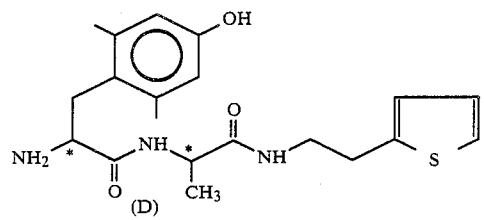

(2,6-Me₂Tyr—(D)Ala—NH(CH₂)₂—thiophene.HCl)

The title compound of Example 38 was deblocked and converted to its HCl salt, the title material, by the method of Example 6.

Optical rotation $[\alpha]_D +101.0°$; $+364.0°$ (365) MeOH.
NMR shift of the (D)Ala methyl=0.99δ (CD₃OD).
Analysis Calcd. for $C_{20}H_{28}N_3O_3SCl$ (MW=425.99): C, 55.22; H, 6.72; N, 9.66. Found: C, 55.50; H, 7.15; N, 9.45.

ROUTE A

EXAMPLE 40

2-thiopheneethanol, 4-methylbenzenesulfonate

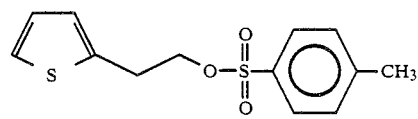

2-thienylethonol (15.0 g, 0.12 mol) dissolved in 75 ml of pyridine was cooled to 0° C. before 22.3 g (0.12 mol) of p-toluenesulfonylchloride were added to the stirred solution under N₂. After stirring this reaction for 2 h at 0° C., it was poured onto ice (~200 g) and this mixture was stirred until all the ice had melted. This two phase mixture was extracted 3×200 ml of Et₂O and these ether extracts were washed 2×125 ml of H₂O, 3×125 ml of 0.5N KHSO₄ and 1×200 ml of H₂O, dried over Na₂SO₄, and stripped of all solvent under reduced pressure. The resulting pale red liquid product (33.0 g) was used without further purification.

EXAMPLE 41

2-thiophenepropanenitrile

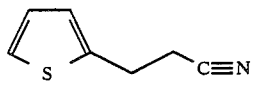

The product of Example 40 (31.1 g, 0.11 mol) was dissolved in a mixture of 540 ml of acetone and 60 ml of water. To this solution was added 19.0 g (0.3 mol) of potassium cyanide. After refluxing this mixture for 48 h under N₂, it was cooled to room temperature and all solvent was removed under reduced pressure. The residue was diluted with 600 ml of H₂O and extracted 3×200 ml of Et₂O. The combined Et₂O extracts were washed with 150 ml of 0.5N KHSO₄ and 150 ml of brine before drying over Na₂SO₄. After the solvent was removed under reduced pressure the crude product was purified on a Waters Prep 500 chromotograph with a Porasil cartridge eluting with 100% toluene (yield=11.8 g).

Analysis Calcd. for C₇H₇NS (MW=137.20): C, 6.28; H, 5.14; N, 10.20; S, 23.37. Found: C, 61.60; H, 5.08, N, 10.03; S, 22.13.

EXAMPLE 42

2-thiophenepropanamine

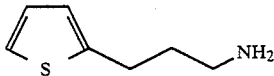

The product of Example 41 (8.3 g, 10.5 mmol) dissolved in 25 ml of Et₂O was added dropwise (15 min.) to a stirred slurry of lithium aluminium hydride(LAH) in 125 ml of dry Et₂O under an Ar atmosphere at room temperature. After the addition was complete the reaction was stirred at room temperature an additional 18 h. With great care, 8.0 ml of water were added dropwise to the vigorously stirred reaction mixture. Following this, 8.0 ml of 4N NaOH were then carefully added. Finally 22 ml of H₂O were added and the aluminum salts were filtered from the Et₂O solution. The filtrate was concentrated to give 8.24 g of the title products which was used without further purification.

EXAMPLE 43

1,1-dimethylethyl [1R-methyl-2-oxo-2-[[3-(2-thienyl)propyl]amino]ethyl]-carbamate

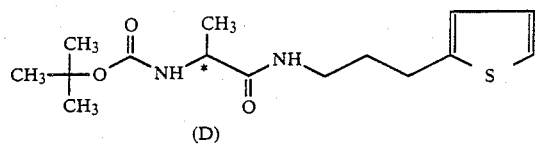

(Boc-(D)Ala-NH(CH₂)₃-2-thiophene)

The title compound was prepared by the method of Example 1 using the title material of Example 42 in place of 6-aminohexanoic acid methyl ester hydrochloride and one equivalent less of NMM.

Optical rotation [α]_D+8.0°; +33.6° (365) CHCl₃.
NMR shift of the (D)Ala methyl=1.28δ (CD₂Cl₂).
Analysis Calcd. for C₁₅H₂₄N₂O₃S.¼ H₂O (MW=316.95): C, 56.84; H, 7.79; N, 8.84; S, 10.12 Found: C, 56.44; H, 7.54; N, 8.66; S, 9.76.

EXAMPLE 44

2R-amino-N-[3-(2-thienyl)propyl]propanamide

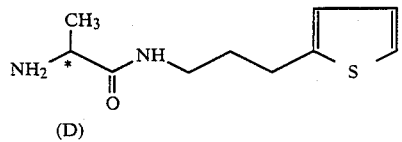

((D)Ala-NH(CH₂)₃-2-thiophene)

The title material of Example 43 (7.9 g, 25.2 mmol) was deblocked by the method of Example 2 to produce the HCl salt. To this material was added 75 ml of 10% potassium bicarbonate (KHCO₃) and 100 ml of CH₂Cl₂. The organic layer was separated, washed with brine (50 ml), dried over Na₂SO₄, and stripped of all solvent to give 4.49 g of the title product as a pale yellow viscous liquid.

Optical rotation [α]_D−9.4°; +9.4° (365) CHCl₃.
NMR of the (D)Ala methyl=1.25δ (CD₂Cl₂).
Analysis Calcd. for C₁₀H₁₆N₂OS (MW=212.32): C, 56.57; H, 7.60; N, 13.19. Found: C, 56.33; H, 7.63; N, 12.92.

EXAMPLE 45

N-[(1,1-dimethylethoxy)carbonyl]-2,6-dimethyl-DL-tyrosyl-N-[3-(2-thienyl)propyl]-D-alaninamide

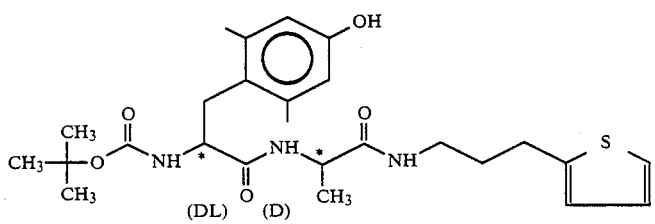

(Boc-2,6Me₂Tyr-(D)Ala-NH(CH₂)₃-2-thiophene)

Racemic t-butoxycarbonyl-2,6-dimethyltyrosine (3.5 g, 11.3 mmol) in 40 ml of $CH_2Cl_2$ was stirred with molecular sieve 5A under Ar for 30 min before being cooled to 0° C. NMM (1.24 ml, 11.3 mmol) was added to this mixture before it was cooled further to −78° C. IBCF (1.5 ml, 11.3 mmol) was then added and the mixture was allowed to warm to room temperature. After 30 min at room temperature, the reaction was cooled to −78° C. and charged with 2.4 g (11.3 mmol) of the title compound of Example 44. This mixture was allowed to warm to room temperature and stir an additional 18 h. The crude product mixture of diastereomers, obtained on workup as described in Example 1, was separated by PLC on Woelm® silica eluting with 1.5% MeOH/CHCl₃.

Diastereomer DF $[\alpha]_D + 4.3°$; +19.6° (365) CHCl₃. NMR shift of the (D)Ala methyl = 1.23δ (CD₂Cl₂).

Analysis Calcd. for $C_{26}H_{37}N_3O_5S$ (MW=503.67): C, 62.00; H, 7.40; N, 8.34; S, 6.37. Found: C, 62.42; H, 7.41; N, 8.07; S, 6.24.

Diastereomer UF $[\alpha]_D + 41.0°$; +166.7° (365) CHCl₃. NMR shift of the (D)Ala methyl = 1.04δ (CD₂Cl₂).

Analysis Calcd. for $C_{26}H_{37}N_3O_5S$ (MW=503.67): C, 62.00; 1 H, 7.40; N, 8.34; S, 6.37. Found: C, 61.73; H, 7.25; N, 8.14; S, 6.19.

EXAMPLE 46

2,6-dimethyltyrosyl-N-[3-(2-thienyl)propyl]-D-alaninamide, monohydrochloride DF isomer (2,6 Me₂Tyr-(D)Ala-NH(CH₂)₃-2-Thiophene.HCl)

The title product was obtained from the DF diastereomer of Example 45 by the method of Example 6.

Optical rotation $[\alpha]_D - 60.5°$; −236.3° (365) MeOH. NMR shift of the (D)Ala methyl = 1.28δ (CD₃OD).

Analysis Calcd. for $C_{21}H_{30}N_3O_3S$ Cl (MW=440.01): C, 57.33; H, 6.87; N, 9.55; S, 7.29; Cl, 8.06. Found: C, 57.17; H, 6.76; N, 9.30; S, 7.28; Cl, 7.87.

EXAMPLE 47

2,6-dimethyltyrosyl-N-[3-(2-thienyl)propyl]-D-alaninamide, monohydrochloride

UF isomer

The title material was obtained from the UF diastereomer of Example 45 by the method of Example 6.

Optical rotation $[\alpha]_D + 126.5°$; +433.5° (365) MeOH. NMR of the (D)Ala methyl = 1.03δ (CD₃OD).

Analysis Calcd. for $C_{21}H_{30}N_3O_3SCl$ (MW=440.01): C, 57.33; H, 6.87; N, 9.55; S, 7.29; Cl, 8.06. Found: C, 57.04; H, 6.77; N, 9.29; S, 7.24; Cl, 7.90.

Corresponding 3-thiophene diastereomers were made using the similar procedures of examples 43, 44, 45 & 46 beginning with the 3-thiophenepropanamine.

2,6-dimethyltyrosyl-N-[3-(3-thienyl)propyl]-D-alaninamide, monohydrochloride

DF isomer

Optical rotation $[\alpha]_D - 59.6°$; −223.0° (365) MeOH. NMR shift of the (D)Ala methyl = 1.27δ (CD₃OD).

Analysis Calcd. for $C_{21}H_{30}N_3O_3SCl$ (MW=440.01) C, 57.33; H, 6.87; N, 9.55; S, 7.29; Cl, 8.06 Found: C, 57.29; H, 7.08; N, 9.78; S, 7.47; Cl, 7.82.

2,6-dimethyltyrosyl-N-[3-(3-thienyl)propyl]-D-alaninamide, monohydrochloride UF isomer Optical rotation $[\alpha]_D + 27.5°$; +393.3° (365) MeOH. NMR of the (D)Ala methyl = 1.04δ (CD₃OD).

Analysis Calcd. for $C_{21}H_{30}N_3O_3SCl$ (MW=440.01) C, 57.33; H, 6.87; N, 9.55; S, 7.29; Cl, 8.06. Found: C, 56.98; H, 7.00; N, 9.62; S, 7.41; Cl, 7.26.

EXAMPLE 48

To a solution of 2-[3-(2-thienyl)-2E-propenyl]-1H-isoindole-1,3 (2H)-dione (9.8 g, 36.4 mmol) dissolved in 300 ml EtOH was added 7.1 ml (145.5 mmol) of hydrazine hydrate (NH₂NH₂.H₂O). The stirred mixture under N₂ was refluxed for 2 hours before cooling to room temperature and standing overnight. The precipitated 2,3-dihydro-1,4-phthalazinedione biproduct was filtered off and the filtrate concentrated precipitating additional solid. After again filtering off the solid birproduct the filtrate was concentrated, filtered, dried over Na₂SO₄ and stripped of all solvent under reduced pressure to give 4.48 g of the title product. This material was used in subsequent reactions without further purification.

EXAMPLE 49

1,1-dimethylethyl [1R-methyl-2-oxo-2-[[3-(2-thienyl)-2E-propenyl]amino]ethyl]carbamate

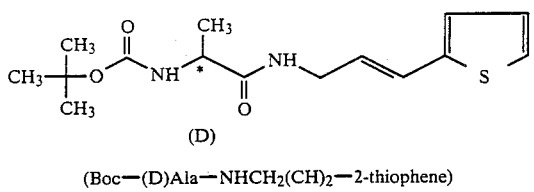

(Boc—(D)Ala—NHCH₂(CH)₂—2-thiophene)

The title compound was prepared by the method of Example 1 using the title material from Example 48 in place of 6-aminohexanoic acid methylester hydrochloride and one equivalent less of NMM.

Optical rotation $[\alpha]_D +18.6°$; $+43.7°$ (365) CHCl₂.
NMR shift of the (D)Ala methyl=1.33δ (CD₂Cl₂).
Analysis Calcd. for C₁₅H₂₂N₂O₃S (MW=310.42): C, 58.04; H, 7.14; N, 9.02; S, 10.33. Found: C, 57.96; H, 7.18; N, 9.02; S, 10.70.

EXAMPLE 50

2R-amino-N-[3-(2-thienyl)-2E-propenyl]propanamide, monohydrochloride

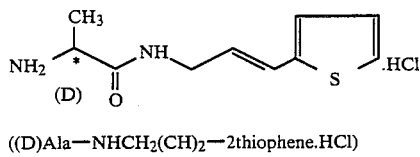

((D)Ala—NHCH₂(CH)₂—2thiophene.HCl)

The title compound was prepared by the method of Example 2 from the title material of Example 49.

Optical rotation $[\alpha]_D -7.8°$ (MeOH).
NMR shift of the (D)Ala methyl=1.48δ (CD₃OD).
Analysis Calcd. for C₁₀H₁₅N₂SO Cl.¼ H₂O (MW=251.27): C, 47.80; H, 6.22; N, 11.15; Cl, 14.10; S, 12.76. Found: C, 48.08; H, 5.97; N, 10.85; Cl, 13.68; S, 12.47.

EXAMPLE 51

N-[(1,1-dimethylethoxy)carbonyl]-2,6-dimethyl-DL-tyrosyl-N-[3-(2-thienyl)-2E-propenyl]-D-alaninamide

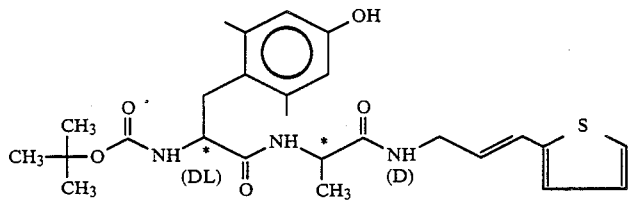

(Box-(DL)2,6 Me₂Tyr-(D)Ala-NHCH₂(CH)₂-2-thiophene)

The title mixture of diastereomers were prepared and separated by the method of Example 45 using the title material from Example 50 in place of the title amide of Example 44.

Diastereomer DF $[\alpha] -17.3°$; $-33.5°$ (365) CHCl₃.
NMR of the (D)Ala methyl=1.31δ (CD₂Cl₂).

Analysis Calcd. for C₂₆H₃₅N₃O₅S.¼H₂ (MW=506.15): C, 61.47; H, 6.99; N, 7.94; S, 6.86. Found: C, 61.59; H, 7.08; N, 7.99; S, 6.38.

Diastereomer UF $[\alpha]_D +11.1°$; $+73.4°$ (365) CHCl₃.
NMR of the (D)Ala methyl=1.03δ (CD₂Cl₂).
Analysis Calcd. for C₂₆H₃₅N₃O₅S.¼ H₂O (MW=506.15): C, 61.47; H, 6.99; N, 7.94; S, 6.86. Found: C, 61.69; H, 7.07; N, 8.30; S, 6.32.

EXAMPLE 52

2,6-dimethyltyrosyl-N-[3-(2-thienyl)-2E-propenyl]-D-alaninamide, monohydrochloride UF isomer

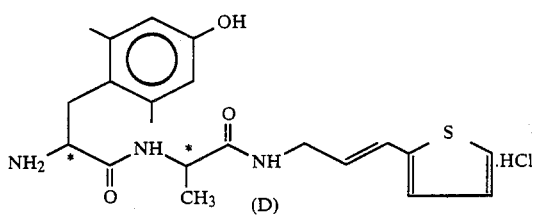

(2,6Me₂Tyr—(D)Ala—NHCH₂(CH)₂—2-thiophene.HCl)

The title compound was synthesized from the UF diastereomer of Example 51 by the method of Example 6.

Optical rotation $[\alpha]_D +62.3°$; $+226.0°$ (365) CH₃OH.
NMR shift of the (D)Ala methyl=1.40δ (CD₃OD).
Analysis Calcd. for C₂₁H₂₈N₃O₃SCl.2 H₂O (MW=474.02): C, 53.21; H, 6.80; N, 8.86; S, 6.76; Cl, 7.48. Found: C, 52.92; H, 6.06; N, 8.29; S, 6.42; Cl, 7.50.

EXAMPLE 53

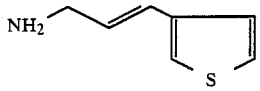

The title compound was prepared from its phthalamide precursor, 2-[3-thienyl)-=2E-propenyl]-1H-isoindole-1,3(2H)-dione by the method of Example 48. The crude reaction product was used in subsequent reactions without further purification.

EXAMPLE 54

1,1-dimethylethyl
[1R-methyl-2-oxo-2-[[3-(3-thienyl)-2E-propenyl-]amino]ethyl]carbamate

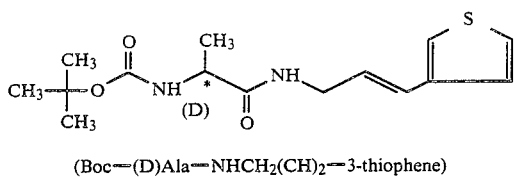

(Boc—(D)Ala—NHCH₂(CH)₂—3-thiophene)

The title material was prepared by the method of Example 1 using the title compound from Example 53 in place of 6-aminohexanoic acid methylester hydrochloride and one equivalent less of NMM.

Optical rotation $[\alpha]_D = +10.7°$; +35.6° (365) CHCl₃.
NMR shift of the (D)Ala methyl = 1.32δ (CD₂Cl₂).
Analysis Calcd. for C₁₅H₂₂N₂O₃S (MW = 310.42): C, 58.04; H, 7.14; N, 9.02; S, 10.33. Found: C, 57.98; H, 7.16; N, 8.97; S, 10.73.

EXAMPLE 55

2R-amino-N-[3-(3-thienyl)-2E-propenyl]propanamide, monohydrochloride

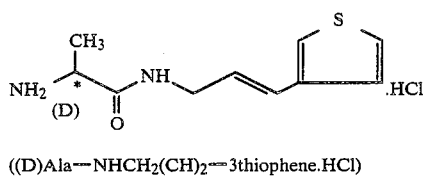

((D)Ala—NHCH₂(CH)₂—3thiophene.HCl)

The title material was prepared by the method of Example 2 from the title compound of Example 54.

Optical rotation $[\alpha]_D$ −13.7° MeOH.
NMR shift of the (D)Ala methyl = 1.52δ (CD₃OD).
Analysis Calcd. for C₁₀H₁₅N₂OSCl.¼H₂O (251.27): C, 47.80; H, 6.22; N, 11.15; S, 12.76; Cl, 14.10. Found: C, 48.16; H, 5.90; N, 11.17; S, 12.65; Cl, 13.72.

EXAMPLE 56

N-[(1,1-dimethylethoxy)carbonyl]-2,6-dimethyl-DL-tyrosyl-N-[3-(3-thienyl)-2E-propenyl]-D-alaninamide

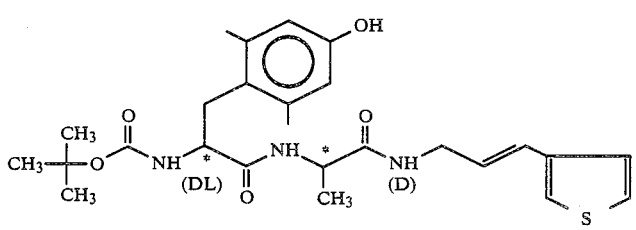

(Boc—(DL)2,6Me₂Tyr—(D)Ala—NHCH₂(CH)₂—3thiophene)

The title mixture of diastereomers were prepared and separated by the method of Example 45 using the title material from Example 55 in place of the title amide of Example 44.

Diastereomer DF $[\alpha]_D$ −9.2°; −39.2° (365) CHCl₃.
NMR shift of the (D)Ala methyl = 1.32δ (CD₂Cl₂).

Analysis Calcd. for C₂₆H₃₅N₃O₅S.¼H₂O (MW = 506.15): C, 61.70; H, 7.07; N, 8.30; S, 6.33. Found: C, 61.71; H, 6.96; N, 8.11; S, 6.35.

Diastereomer UF $[\alpha]_D$ +26.3°; +129.8° (365) CHCl₃.
NMR shift of the (D)Ala methyl = 1.07δ (CD₂Cl₂).
Analysis Calcd. for C₂₆H₃₅N₃O₅S (MW = 501.66): C, 62.25; H, 7.03; N, 8.39; S, 6.39. Found: C, 62.35; H, 7.09; N, 7.97; S, 6.39.

EXAMPLE 57

2,6-dimethyltyrosyl-N-[3-(3-thienyl)-2E-propenyl]-D-alaninamide, monohydrochloride DF isomer

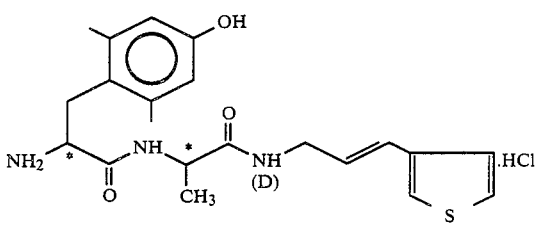

((D)2,6Me₂Tyr—(D)Ala—NHCH₂(CH)₂—3-thiophene.HCl)

The title compound was synthesized from the DF diastereomer of Example 56 by the method of Example 6.

Optical rotation $[\alpha]_D$ −75.1°; −283.9° (365) CH₃OH.
NMR shift of the (D)Ala methyl = 1.30δ (CD₃OD).
Analysis Calcd. for C₂₁H₂₈N₃O₃SCl.H₂O (456.01): C, 55.31; H, 6.63; N, 9.21; S, 7.03; Cl, 7.77. Found: C, 55.06; H, 6.34; N, 8.83; S, 6.67; Cl, 8.18.

EXAMPLE 58

2,6-dimethyltyrosyl-N-[3-(3-thienyl)-2E-propenyl]-D-alaninamide, monohydrochloride UF isomer

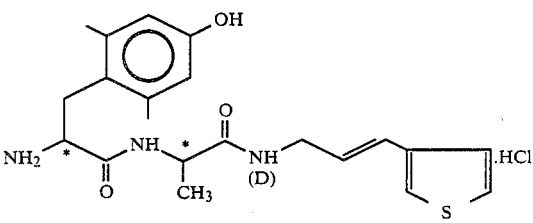

(2,6Me₂Tyr—(D)Ala—NHCH₂(CH)₂—3-thiophene.HCl)

The title compound was prepared from the UF diastereomer of Example 57 by the method of Example 6.

Optical rotation $[\alpha]_D$ +86.8°; +335.6° (365) MeOH.

NMR shift of the (D)Ala methyl=1.06δ (CD₃OD).
Analysis Calcd. for $C_{21}H_{28}N_3O_3SCl.\frac{1}{2}H_2O$ (437.00): C, 56.42; H, 6.54; N, 9.40; S, 7.17; Cl, 7.93. Found: C, 56.65; H, 6.54; N, 9.09; S, 6.93; Cl, 7.88.

EXAMPLE 59 phenylmethyl [2-[[3-(4-methoxyphenyl)propyl]amino]-1R-methyl-2-oxoethyl]carbamate

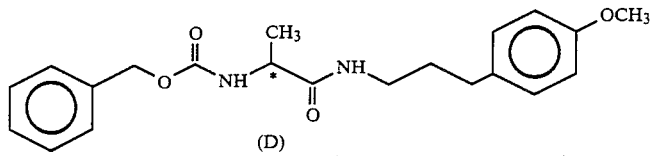

(Z—(D)Ala—NH(CH₂)₃—Ph(4-OMe))

The title compound was prepared by the method of Example 8 using NH₂(CH₂)₃Ph(4-MeO) in place of NH2Ad.HCl and one equivalent less of NMM.
Optical rotation $[\alpha]_D$ +21.8°; +83.7° (365) CHCl₃.
NMR shift of the (D)Ala methyl=1.31δ (CD₂Cl₂).
Analysis Calcd. for $C_{21}H_{26}N_2O_4$ (MW=370.46): C, 68.09; H, 7.07; N, 7.56. Found: C, 68.02; H, 6.90; N, 7.45.

EXAMPLE 60

αR-amino-N-[3-(4-methoxyphenyl)propyl]propanamide

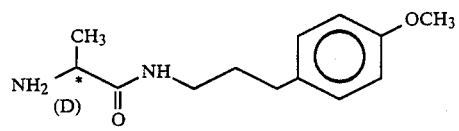

((D)Ala—NH(CH₂)₃Ph(4-OMe))

The title compound was prepared from the title material of Example 59 by the method of Example 9.
Optical rotation $[\alpha]_D$ −11.2°; +5.6° (355) CHCl₃.
NMR shift of the (D)Ala methyl=1.27δ (CD₂Cl₂).
Analysis Calcd. for $C_{13}H_{20}N_2O_2.\frac{1}{4}H_2O$ (MW=240.83): C, 64.84; H, 8.58; N, 11.63. Found: C, 64.81; H, 8.62; N, 10.91.

EXAMPLE 61

N-[(1,1-dimethylethoxy)carbonyl]-2,6-dimethyl-DL-tyrosyl-N-[3-(4-methoxyphenyl)propyl]-D-alaninamide

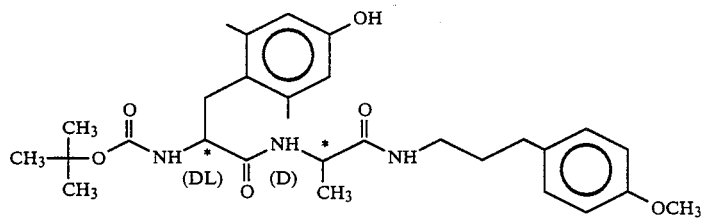

(Boc—(DL)2,6Me₂Tyr—(D)Ala—NH(CH₂)₃Ph(4-OMe))

The title mixture of diastereomers was prepared and separated by the method of Example 45 using the title material from Example 59 in place of the title amide of Example 44.

Diastereomer DF $[\alpha]_D$ +9.1°; +18.3° (365) CHCl₃.
NMR shift of the (D)Ala methyl=1.30δ (CD₂Cl₂).
Analysis Calcd. for $C_{29}H_{41}N_3O_6$ (MW=527.67): C, 66.01; H, 7.83; N, 7.96. Found: C, 66.08; H, 7.75; N, 7.95.
Diastereomer UF $[\alpha]_D$ +41.7°; +176.7° (365) CHCl₃.
NMR shift of the (D)Ala methyl=1.05δ (CD₂Cl₂).
Analysis Calcd. for $C_{29}H_{41}N_3O_6$ (MW=527.67): C, 66.01; H, 7.83; N, 7.96. Found: C, 65.64; H, 7.80; N, 7.75.

EXAMPLE 62

2,6-dimethyltyrosyl-N-[3-(4-methoxyphenyl)propyl]-D-alaninamide, monohydrochloride DF isomer

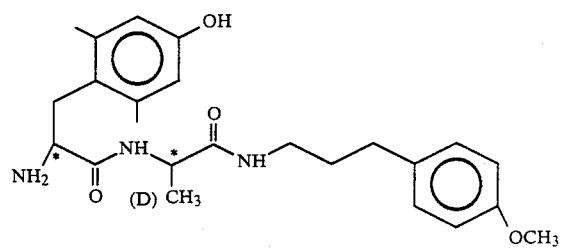

((D)2,6Me₂Tyr—(D)Ala—NH(CH₂)₃Ph(4-OMe).HCl)

The title compound was synthesized from the DF diastereomer of Example 61 by the method of Example 6.
Optical rotation $[\alpha]_D$ −67.3°; −230.9° (365) MeOH.
NMR shift of the (D)Ala methyl=1.27δ (CD₃OD).
Analysis Calcd. for $C_{24}H_{34}N_3O_4Cl.\frac{1}{4}H_2O$ (MW=464.02): C, 61.52; H, 7.42; N, 8.97; Cl, 7.57. Found: C, 61.62; H, 7.23; N, 8.92; Cl, 7.10.

EXAMPLE 63

2,6-dimethyltyrosyl-N-[3-(4-methoxyphenyl)propyl]-D-alaninamide, hydrochloride

UF isomer

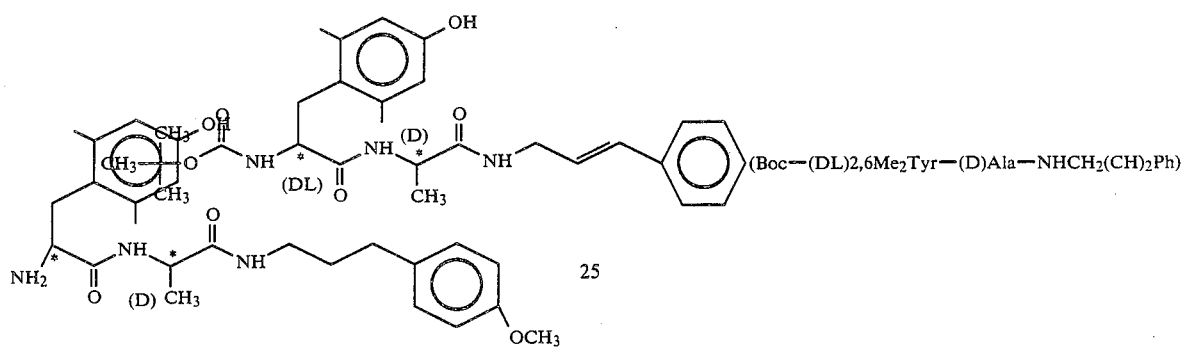

(2,6Me₂Tyr—(D)Ala—NH(CH₂)₃Ph(4-OMe).HCl)

The title material was prepared from the UF diastereomer of Example 61 by the method of Example 6.

Optical rotation $[\alpha]_D$ +99.0°; +362.0° (365) MeOH.
NMR shift of the (D)Ala methyl=1.04δ (CD₃OD).
Analysis Calcd. for $C_{24}H_{33}N_3O_4 \cdot 1\frac{1}{8}HCl \cdot \frac{3}{4}H_2O$ (MW=481.78): C, 59.83; H, 7.39; N, 8.72; Cl, 8.28.
Found: C, 59.77; H, 7.02; N, 8.61, Cl, 8.29.

EXAMPLE 64

1,1-dimethylethyl [1R-methyl-2-oxo-2-[(3-phenyl-2E-propenyl)amino]ethyl]carbamate

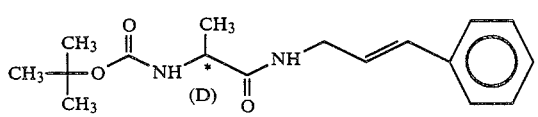

(Boc—(D)Ala—NHCH₂(CH)₂Ph)

The title compound was prepared by the method of Example 1 using phenylallylamine in place of 6-aminohexanoic acid methyl ester and one equivalent less of NMM.

NMR shift of the (D)Ala methyl=1.36δ (CDCl₃).
Analysis Calcd. for $C_{17}H_{24}N_2O_3 \cdot \frac{1}{2}H_2O$ (MW=313.40): C, 65.15; H, 8.04; N, 8.94. Found: C, 65.39; H, 7.81; N, 9.18.

EXAMPLE 65

αR-amino-N-(3-phenyl-2E-propenyl)propanamide

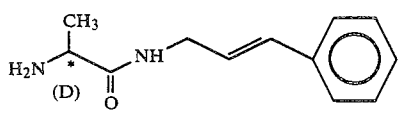

((D)Ala—NHCH₂(CH)₂Ph)

The title compound of Example 64 was prepared by the method of Example 2 from the title product of Example 64 to produce the HCl salt. The free base was formed and isolated by the method of Example 44.

NMR shift of the (D) Ala methyl=1.35δ (CDCl₃).

EXAMPLE 66

N-[(1,1-dimethylethoxy)carbonyl]-2,6-dimethyl-DL-tyrosyl-N-(3-phenyl-2E-propenyl)-D-alaninamide The title compound was prepared by the method of Example 45 using the product of Example 65 instead of the product of Example 44. The diastereomers were separated by LPC on Porasil eluting with 1.4% MeOH/CHCl₃.

Diastereomer DF: NMR shift of the (D Ala methyl=1.24δ (DMSOd₆).
Diastereomer UF: NMR shift of the (D)Ala methyl=1.08δ (CDCl₃).

EXAMPLE 67

2,6-dimethyltyrosyl-N-(3-phenyl-2E-propenyl)-D-alaninamide, monohydrochloride

DF isomer ((D)2,6Me₂Tyr—(D)Ala—NHCH₂(CH)₂Ph.HCl)

The title product was obtained from the DF-diastereomer of Example 66 by the method of Example 6.

Optical rotation $[\alpha]_D$ −78.8°; −293.5° (365) MeOH.
NMR shift of the (D) Ala methyl=1.20δ (DMSOd₆).
Analysis Calcd. for $C_{23}H_{29}N_3O_3 \cdot HCl \cdot \frac{1}{2}C_2H_4O_2$ (MW=461.99): C, 62.37; H, 6.98; N, 9.09; Cl, 7.67. Found: C, 62.27; H, 6.93; N, 8.89; Cl, 7.86.

EXAMPLE 68

2,6-dimethyltyrosyl-N-(3-phenyl-2E-propenyl)-D-alaninamide, monohydrochloride

UF isomer

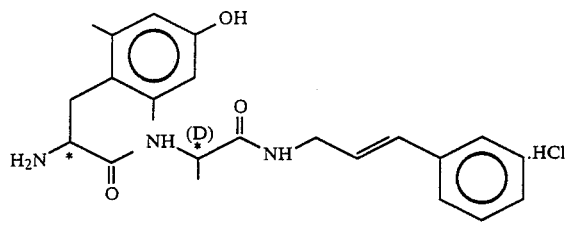

(2,6Me₂Tyr—(D)Ala—NHCH₂CH)₂Ph.HCl)

The title product was obtained from the UF-diastereomer from Example 66 by the method of Example 6. Optical rotation $[\alpha]_D$ +69.2°; +257.2° (365) CH₃OH.
NMR shift of the (D)Ala methyl=0.99δ (DMSOd₆).
Analysis Calcd. for C₂₃H₂₉N₃O₃.HCl.½H₂O (MW=440.97): C, 62.65; H, 7.09; N, 9.53; Cl 8.04.

Found: C, 62.93; H, 6.93; H, 9.18; Cl, 7.93.

EXAMPLE 69 phenylmethyl [2-[(3,3-diphenylpropyl)amino]-1R-methyl-2-oxoethyl]-carbamate

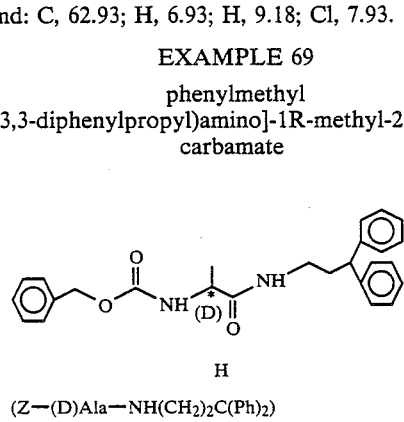

(Z—(D)Ala—NH(CH₂)₂C(Ph)₂)

The title compound was made by the method of Example 8 where 3,3-diphenylpropyl amine was substituted for the NH2Ad.HCl using one less equivalent of NMM.
NMR shift of the (D)Ala methyl=1.27δ (CDCl₃).

EXAMPLE 70

αR-amino-N-(3,3-diphenylpropyl)propanamide

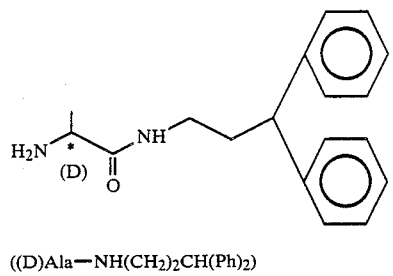

((D)Ala—NH(CH₂)₂CH(Ph)₂)

The title compound was prepared by the method of Example 9 substituting the product of Example 69 for the product of Example 8.
NMR shift of the (D)Ala methyl=1.27δ (CDCl₃).

EXAMPLE 71

N-[(1,1-dimethylethoxy)carbonyl]-2,6-dimethyl-DL-tyrosyl-N-(3,3-diphenylpropyl)-D-alaninamide

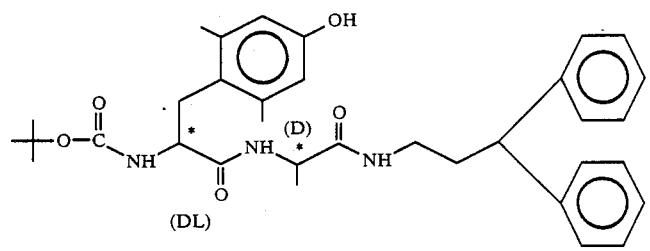

(Boc—(DL)2,6-Me₂Tyr—(D)Ala—NH(CH₂)₂CH(Ph)₂)

The title product was prepared by the method of Example 45 using the product of Example 71 instead of the product of Example 44. The diastereomers were separated by LPC on Porasil eluting with 1%–5% isopropylalcohol/trichloro-trifluoroethane.

Diastereomer DF: NMR shift of the (D)Ala Methyl=1.19δ (DMSOd₆).
Diastereomer UF: NMR shift of the (D)Ala methyl=0.98δ (DMSOd₆).

EXAMPLE 72

2,6-dimethyltyrosyl-N-(3,3-diphenylpropyl)-D-alaninamide, monohydrochloride

DF isomer

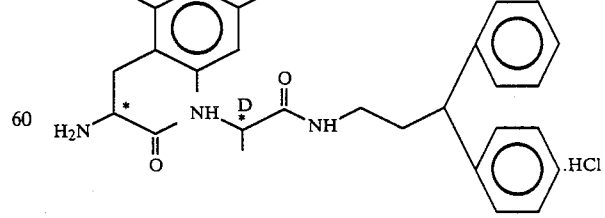

((D)2,6Me₂Tyr—(D)Ala—NH(CH₂)₂CH(Ph)₂.HCl)

The title product was obtained from DF diastereomer of Example 71 by the method of Example 6.

Optical rotation [α]$_D$ −58.6°; −198.1° (365) CH$_3$OH.
NMR shift of the (D)Ala methyl=1.27δ (CD$_3$OD).
Analysis Calcd. for C$_{29}$H$_{35}$N$_3$O$_3$.HCl.½H$_2$O (MW=510.08): C, 67.10; H, 7.18; N, 8.10; Cl, 6.83. Found: C, 67.12; H, 6.98; N, 8.09; Cl, 6.86.

EXAMPLE 73

2,6-dimethyltyrosyl-N-(3,3-diphenylpropyl)-D-alaninamide, monohydrochloride

UF isomer

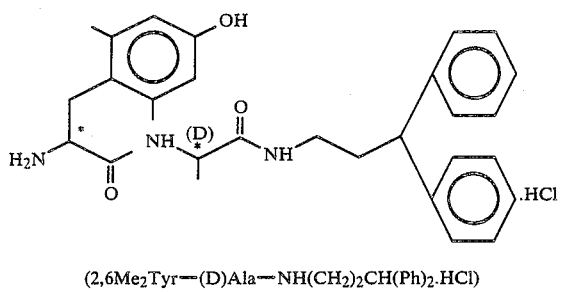

(2,6Me$_2$Tyr—(D)Ala—NH(CH$_2$)$_2$CH(Ph)$_2$.HCl)

The title product was obtained from the UF-Diastereomer of Example 71 by the method of Example 6.

Optical rotation [α]$_D$ +97.8°; +360.0° (365) CH$_3$OH.
NMR shift the (D)Ala methyl=1.02δ (CD$_3$OD).

Analaysis Calcd. for C$_{29}$H$_{35}$N$_3$O$_3$.HCl.½H$_2$O (MW=510.08): C, 67.10; H, 7.18; N, 8.10; Cl, 6.83. Found: C, 66.70; H, 6.94; N, 8.05; Cl, 6.85.

EXAMPLE 74

N-[(1,1-dimethylethoxy)carbonyl]-2,6-dimethyl-DL-tyrosyl-N-[3-(3-pyridinyl)-2E-propenyl]-D-alaninamide (Boc(DL)2,6—Me$_2$Tyr—(D)Ala—NHCH$_2$(CH)—3Pyr)

The title product was prepared by the method of Example 18 using the DL mixture of diastereomers from the product of Example 16 and 3-(3-pyridinyl)-2E-propen-1-amine. The reaction product was purified by PLC on Porasil eluting with 10/45/45 isopropylalcohol/trichloro-trifluoro-ethane/CH$_2$Cl$_2$ to give the product mixture of diastereomers.

EXAMPLE 75

2,6-dimethyl-DL-tyrosyl-N-[3-(3-pyridinyl)-2E-propenyl]-D-alaninamide, dihydrochloride ((DL)2,6Me$_2$Tyr—(D)Ala—NHCH$_2$(CH)$_2$—3Pyr.2HCl)

The title product was prepared from the diastereomeric mixture of Example 74 by the method of Example 6.

NMR shift for (D)Ala methyls=1.09 and 1.34δ (CD$_3$OD).

Analysis Calcd. for C$_{22}$H$_{28}$N$_4$O$_3$.2HCl.CH$_3$CO$_2$H.¾H$_2$O (MW 542.98): C, 53.09; H, 6.59; N, 10.32; Cl, 13.06. Found: C, 53.34; H, 6.22; N, 10.11; Cl, 12.74.

EXAMPLE 76

N-[(1,1-dimethylethoxy)carbonyl]-2,6-dimethyl-DL-tyrosyl-N-3-(3-pyridinyl)propyl]-D-alaninamide (Boc—(DL)2,6Me$_2$Tyr—(D)Ala—NH(CH$_2$)$_3$—3Pyr)

The title product was prepared by the Method of Example 18 using the product diastereomeric mixture from Example 16 and 3-pyridinepropanamine. The diastereomers were separated by PLC on Porasil using 2% to 2.3% MeOH/CH$_2$Cl$_2$.

Diastereomer DF: nmr shift of the (D)Ala methyl=1.30δ (CDCl$_3$).

Diastereomer UF: nmr shift of the (D)Ala methyl=1.06δ (CDCl$_3$).

EXAMPLE 68

2,6-dimethyltyrosyl-N-(3-phenyl-2E-propenyl)-D-alaninamide, monohydrochloride

UF isomer

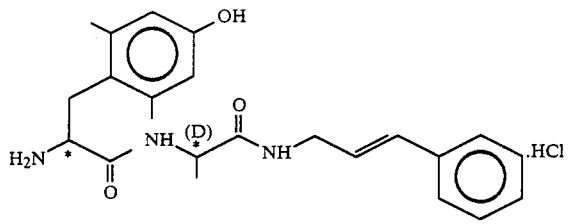

(2,6Me2Tyr—(D)Ala—NHCH2CH)2Ph.HCl)

The title product was obtained from the UF-diastereomer from Example 66 by the method of Example 6.

Optical rotation $[\alpha]_D$ +69.2°; +257.2° (365) CH3OH.
NMR shift of the (D)Ala methyl=0.99δ (DMSOd6).
Analysis Calcd. for $C_{23}H_{29}N_3O_3 \cdot HCl \cdot \frac{1}{2}H_2O$ (MW=440.97): C, 62.65; H, 7.09; N, 9.53; Cl 8.04.
Found: C, 62.93; H, 6.93; H, 9.18; Cl, 7.93.

EXAMPLE 69 phenylmethyl [2-[(3,3-diphenylpropyl)amino]-1R-methyl-2-oxoethyl]-carbamate

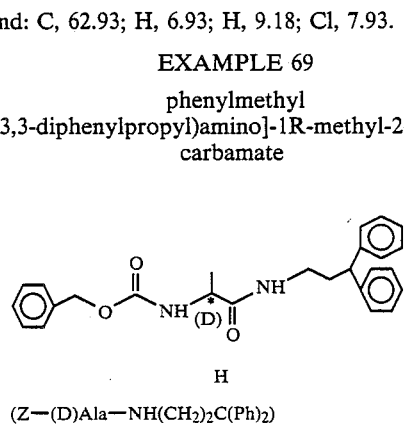

(Z—(D)Ala—NH(CH2)2C(Ph)2)

The title compound was made by the method of Example 8 where 3,3-diphenylpropyl amine was substituted for the NH2Ad.HCl using one less equivalent of NMM.

NMR shift of the (D)Ala methyl=1.27δ (CDCl3).

EXAMPLE 70

αR-amino-N-(3,3-diphenylpropyl)propanamide

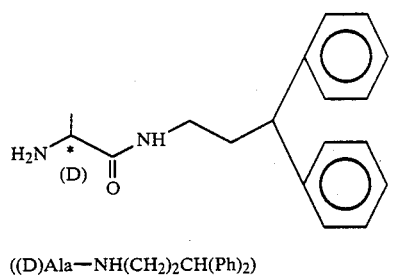

((D)Ala—NH(CH2)2CH(Ph)2)

The title compound was prepared by the method of Example 9 substituting the product of Example 69 for the product of Example 8.

NMR shift of the (D)Ala methyl=1.27δ (CDCl3).

EXAMPLE 71

N-[(1,1-dimethylethoxy)carbonyl]-2,6-dimethyl-DL-tyrosyl-N-(3,3-diphenylpropyl)-D-alaninamide

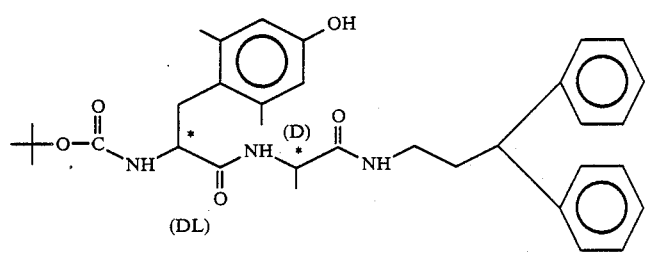

(Boc—(DL)2,6-Me2Tyr—(D)Ala—NH(CH2)2CH(Ph)2)

The title product was prepared by the method of Example 45 using the product of Example 71 instead of the product of Example 44. The diastereomers were separated by LPC on Porasil eluting with 1%–5% isopropylalcohol/trichloro-trifluoroethane.

Diastereomer DF: NMR shift of the (D)Ala Methyl=1.19δ (DMSOd6).

Diastereomer UF: NMR shift of the (D)Ala methyl=0.98δ (DMSOd6).

EXAMPLE 72

2,6-dimethyltyrosyl-N-(3,3-diphenylpropyl)-D-alaninamide, monohydrochloride

DF isomer

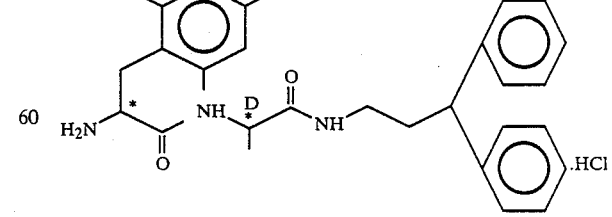

((D)2,6Me2Tyr—(D)Ala—NH(CH2)2CH(Ph)2.HCl)

The title product was obtained from DF diastereomer of Example 71 by the method of Example 6.

Optical rotation [α]$_D$ −58.6°; −198.1° (365) CH$_3$OH.
NMR shift of the (D)Ala methyl=1.27δ (CD$_3$OD).
Analysis Calcd. for C$_{29}$H$_{35}$N$_3$O$_3$.HCl.½H$_2$O (MW=510.08): C, 67.10; H, 7.18; N, 8.10; Cl, 6.83.
Found: C, 67.12; H, 6.98; N, 8.09; Cl, 6.86.

EXAMPLE 73

2,6-dimethyltyrosyl-N-(3,3-diphenylpropyl)-D-alaninamide, monohydrochloride

UF isomer

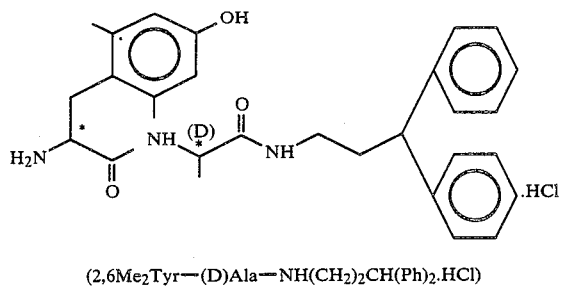

(2,6Me$_2$Tyr—(D)Ala—NH(CH$_2$)$_2$CH(Ph)$_2$.HCl)

The title product was obtained from the UF-Diastereomer of Example 71 by the method of Example 6.
Optical rotation [α]$_D$ +97.8°; +360.0° (365) CH$_3$OH.
NMR shift the (D)Ala methyl=1.02δ (CD$_3$OD).

Analaysis Calcd. for C$_{29}$H$_{35}$N$_3$O$_3$.HCl.½H$_2$O (MW=510.08): C, 67.10; H, 7.18; N, 8.10; Cl, 6.83.
Found: C, 66.70; H, 6.94; N, 8.05; Cl, 6.85.

EXAMPLE 74

N-[(1,1-dimethylethoxy)carbonyl]-2,6-dimethyl-DL-tyrosyl-N-[3-(3-pyridinyl)-2E-propenyl]-D-alaninamide

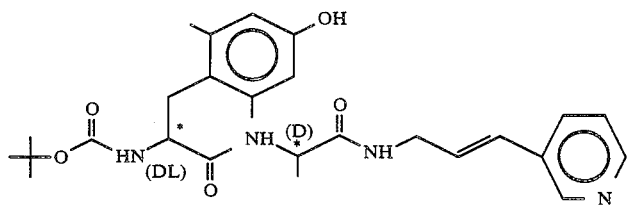

(Boc(DL)2,6—Me$_2$Tyr—(D)Ala—NHCH$_2$(CH)—3Pyr)

The title product was prepared by the method of Example 18 using the DL mixture of diastereomers from the product of Example 16 and 3-(3-pyridinyl)-2E-propen-1-amine. The reaction product was purified by PLC on Porasil eluting with 10/45/45 isopropylalcohol/trichloro-trifluoro-ethane/CH$_2$Cl$_2$ to give the product mixture of diastereomers.

EXAMPLE 75

2,6-dimethyl-DL-tyrosyl-N-[3-(3-pyridinyl)-2E-propenyl]-D-alaninamide, dihydrochloride

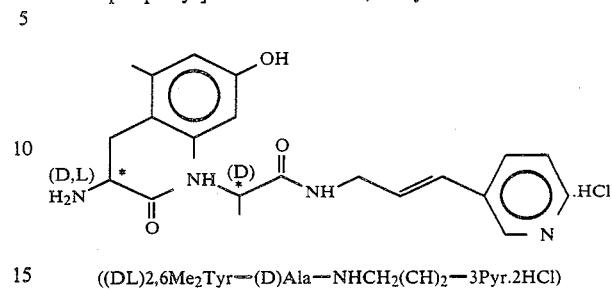

((DL)2,6Me$_2$Tyr—(D)Ala—NHCH$_2$(CH)$_2$—3Pyr.2HCl)

The title product was prepared from the diastereomeric mixture of Example 74 by the method of Example 6.
NMR shift for (D)Ala methyls=1.09 and 1.34δ (CD$_3$OD).
Analysis Calcd. for C$_{22}$H$_{28}$N$_4$O$_3$.2HCl.CH$_3$CO$_2$H.¾H$_2$O (MW 542.98): C, 53.09; H, 6.59; N, 10.32; Cl, 13.06.
Found: C, 53.34; H, 6.22; N, 10.11; Cl, 12.74.

EXAMPLE 76

N-[(1,1-dimethylethoxy)carbonyl]-2,6-dimethyl-DL-tyrosyl-N-3-(3-pyridinyl)propyl]-D-alaninamide

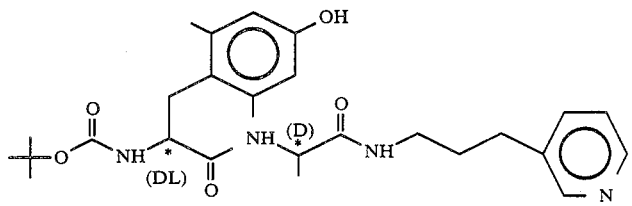

(Boc—(DL)2,6Me$_2$Tyr—(D)Ala—NH(CH$_2$)$_3$—3Pyr)

The title product was prepared by the Method of Example 18 using the product diastereomeric mixture from Example 16 and 3-pyridinepropanamine. The diastereomers were separated by PLC on Porasil using 2% to 2.3% MeOH/CH$_2$Cl$_2$.
Diastereomer DF: nmr shift of the (D)Ala methyl=1.30δ (CDCl$_3$).
Diastereomer UF: nmr shift of the (D)Ala methyl=1.06δ (CDCl$_3$).

The title mixture of diastereomers were prepared by the method of Example 45 using the free base of the product of Example 86 produced by the method of Example 44 instead of the product of Example 44.

The diastereomers were separated by PLC on porasil eluting with 3% MeOH/CH₂Cl₂.
Diastereomer DF:
NMR shift of the (D)Ala methyl=1.26δ (DMSOd₆)
Diastereomer UF:
NMR shift of the (D)Ala methyl=1.12δ (CDCl₃).

EXAMPLE 88

2,6-dimethyltyrosyl-N-[3-(4-cyanophenyl)-2E-propenyl]-D-alaninamide, monohydrochloride DF isomer

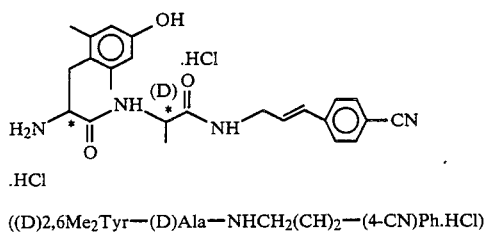

((D)2,6Me₂Tyr—(D)Ala—NHCH₂(CH)₂—(4-CN)Ph.HCl)

The title product was prepared by the method of Example 6 using the DF diastereomer of Example 87.
Optical rotation $[\alpha]_D$ −82.9°; −345.7° (365) MeOH.
NMR shift for the (D)Ala methyl=1.32δ (CH₃OD).
Analysis Calcd. for C₂₄H₂₈N₄O₃.HCl.CH₃CO₂H (MW=517.07): C, 60.40; H, 6.43; N, 10.84; Cl, 6.86. Found: C, 60.11; H, 6.39; N, 11.01; Cl, 7.24.

EXAMPLE 89

2,6-dimethyltyrosyl-N-[3-(4-cyanophenyl)-2E-propenyl]-D-alaninamide, monohydrochloride UF isomer

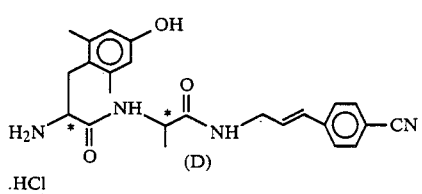

(2,6Me₂Tyr—(D)Ala—NHCH₂(CH)₂—(4-CN)Ph.HCl)

The title product was prepared by the method of Example 6 using the UF diastereomer of Example 87.

Optical rotation $[\alpha]_D$+62.6°; +238.3° (365) MeOH.
NMR shift for the (D)Ala methyl=1.08δ (CD₃OD).
Analysis Calcd. for C₂₄H₂₈N₄O₃.HCl.CH₃CO₂H (MW=517.07): C, 60.40; H, 6.43; N, 10.84; Cl, 6.86. Found: C, 60.65; H, 6.55; N, 11.15; Cl, 7.24.

EXAMPLE 90

N-[(1,1-dimethylethoxy)carbonyl]-2,6-dimethyl-D-tyrosyl-N-[3-(4-cyanophenyl)propyl]-D-alaninamide

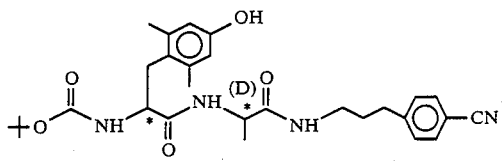

(Boc—(D)2,6Me₂Tyr—(D)Ala—NH(CH₂)₃(4-CN)Ph)

The title product was obtained by hydrogenation of the DF diastereomer from Example 87 in THF at ambient temperature and pressure using 5% Pd/C as catalyst. The catalyst was removed by filtration and the solvent was removed by distillation. The resultant product was used without further purification.

EXAMPLE 91

2,6-dimethyltyrosyl-N-(4-cyanophenyl)propyl]-D-alaninamide monohydrochloride

DF isomer

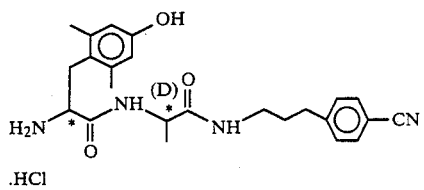

((D)2,6Me₂Tyr—(D)Ala—NH(CH₂)₃(4-CN)Ph.HCl)

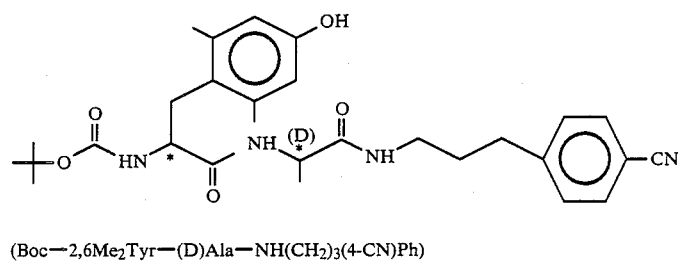

(Boc—2,6Me₂Tyr—(D)Ala—NH(CH₂)₃(4-CN)Ph)

The title compound was prepared from the title compound of Example 90 using the procedure of Example 6.
Optical rotation $[\alpha]_D$ −67.9°; −246.5° (365) MeOH.
NMR shift of the (D)Ala methyl=1.26δ (CD₃OD).
Analysis Calcd. for C₂₄H₃₀N₄O₃.HCl.¼C₄H₈O₂ (MW 499.03): C, 60.17; H, 7.07; N, 11.23; Cl, 7.10. Found: C, 60.01; H, 6.67; N, 11.07; Cl, 7.18.

EXAMPLE 92

N-[(1,1-dimethylethoxy)carbonyl]-2,6-dimethyltyrosyl-N-[3-(4-cyanophenyl)propyl]-D-alaninamide, isomer UF

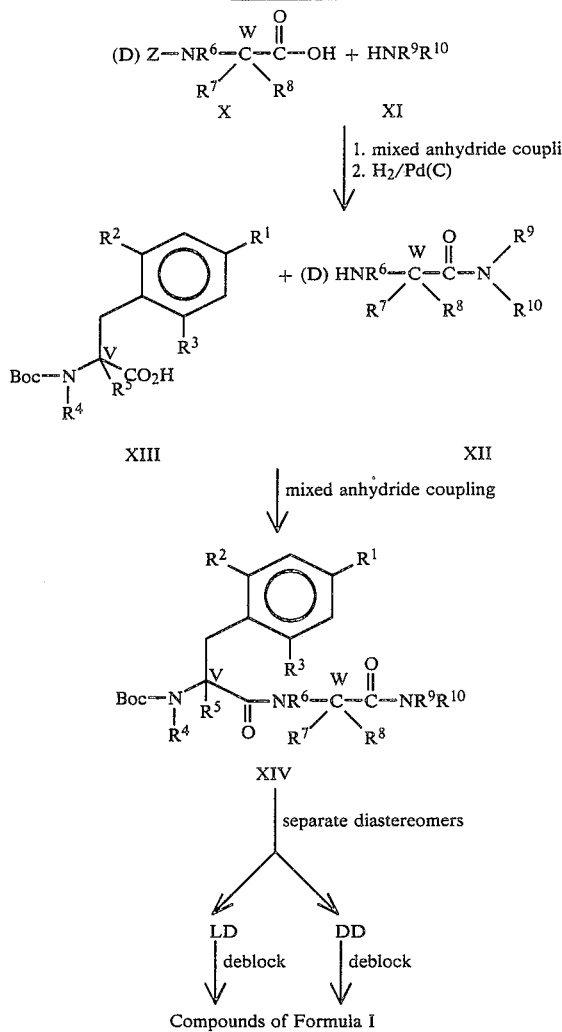

The title product was prepared from the UF diastereomer from Example 87 using the method of Example 90.

EXAMPLE 93

2,6-dimethyltyrosyl-N-[3-(4-cyanophenyl)propyl]-D-alaninamide, monohydrochloride UF isomer

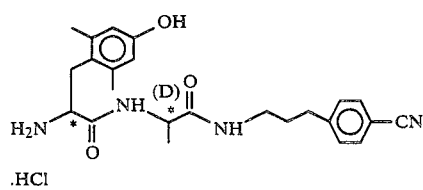

(2,6Me₂Tyr—(D)Ala—NH(CH₂)₃(4-CN)Ph.HCl)

The title compound was prepared from the title product of Example 92 using the method of Example 6.

Optical rotation $[\alpha]_D + 92.7°$; $+349.3°$ (365) MeOH.

NMR shift for the (D)Ala methyl = 1.04δ(CD₃OD).

Analysis Calcd. for $C_{24}H_{30}N_4O_3 \cdot HCl \cdot \frac{1}{4}C_4H_8O_2 \cdot \frac{3}{4}$ H₂O (MW = 494.53): C, 60.71; H, 7.03; N, 11.33; Cl, 7.17. Found: C, 60.71; H, 6.85; N, 10.99; Cl, 7.11.

EXAMPLE 94 phenylmethyl [2-[[3-(1,3-benzodioxol-5-yl)-2E-propenyl]amino]-1R-methyl-2-oxoethyl]carbamate

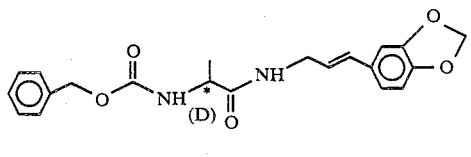

(Z—(D)Ala—NH—CH₂—(CH)₂—(3,4-CH₂O₂)Ph)

The title compound was prepared by the method of Example 8 where 3-(1,3-benzodioxol-5-yl)-2E-propen-1-amine is substituted for NH₂2Ad.HCl using one less

EXAMPLE 95

R-amino-N-[3-(1,3-benzodioxol-5-yl)propyl]propanamide

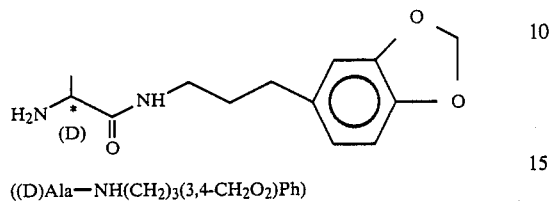

((D)Ala—NH(CH₂)₃(3,4-CH₂O₂)Ph)

The title product was obtained by hydrogenating the product of Example 94 in THF at 60 psi and ambient temperature using 5% Pd/C as a catalyst. The resultant residual oil after filtering off the catalyst and removing the solvent under reduced pressure was used without further purification.

NMR shift for the (D)Ala methyl=1.30δ (CDCl₃).

EXAMPLE 96

N-[(1,1-dimethylethoxy)carbonyl]-2,6-dimethyl-DL-tyrosyl-N-[3-(1,3-benzodioxol-5-yl)propyl]-D-alaninamide

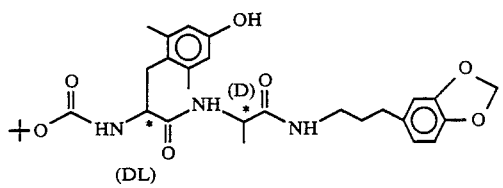

(Boc—(DL)2,6Me₂Tyr—(D)Ala—NH(CH₂)₃(3,4CH₂O₂)Ph)

The title mixture of diastereomers were prepared by the method of Example 45 using the product of Example 95 instead of the product of Example 44. The diastereomers were separated by gradient PLC on Woelm® Silica eluting with 1.5 to 3.5% MeOH/CHCl₃.

Diastereomer DF: NMR shift of the (D) Ala methyl=1.31δ (CD₃OD).

Diastereomer UF: NMR shift of the (D) Ala methyl=1.04δ (CD₃OD).

EXAMPLE 97

2,6-dimethyltyrosyl-N-[3-(1,3-benzodioxol-5-yl)propyl]-D-alaninamide, monohydrochloride DF isomer

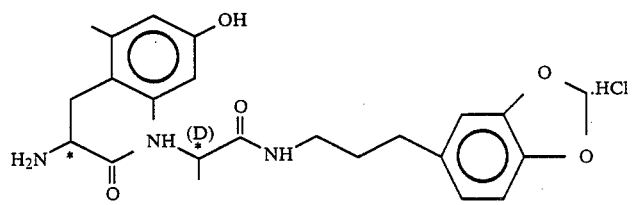

((D)2,6Me₂Tyr—(D)Ala—NH(CH₂)₃(3,4CH₂O₂)Ph.HCl)

The title compound was prepared from the DF diastereomer of the title product of Example 96 using the method of Example 6.

Optical rotation [α]−57.1°; −214.3° (365) MeOH.
NMR shift of the (D)Ala methyl=1.25δ (CD₃OD).
Analysis Calcd. for C₂₄H₃₁N₃O₅.HCl.⅛C₄H₈O₂.7/16-H₂O (MW=496.89): C, 59.22; H, 6.87; N, 8.46; Cl, 7.14. Found: C, 59.12; H, 6.82; N, 8.06; Cl, 7.54.

EXAMPLE 98

2,6-dimethyltyrosyl-N-[3-(1,3-benzodioxol-5-yl)propyl]D-alaninamide, monohydrochloride UF isomer

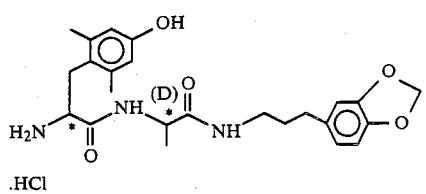

(2,6Me₂Tyr—(D)Ala—NH(CH₂)₃(3,4CH₂O₂)Ph.HCl)

The title compound was prepared from the UF diastereomer of the title product of Example 96 using the method of Example 6.

Optical rotation [α]_D+94.7°; +340.1° (365) CH₃OH.
NMR Shift of the (D)Ala methyl=1.02δ (CD₃OD).
Analysis Calcd. for C₂₄H₃₁N₅O₅.⅛C₄H₈O₂.¼H₂O (MW=493.51): C, 59.63; H, 6.84; N, 8.51; Cl, 7.18. Found: C, 59.51; H, 6.93; N, 8.27; Cl, 7.50.

EXAMPLE 99 phenylmethyl [1R-methyl-2-[(1-methyl-3-phenylpropyl)amino]-2-oxoethyl]carbamate

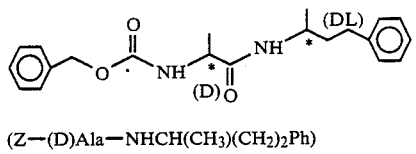

(Z—(D)Ala—NHCH(CH₃)(CH₂)₂Ph)

The title product was prepared by the method of Example 8 when α-methylbenzenepropanamine was substituted for the N2H₂Ad.HCl using one less equivalent of NMM.

NMR shifts for the methyls of (D)Ala and α methyl PPA=two pairs of doublets: 1.12δ and 1.14δ plus 1.35δ and 1.33δ (CDCl₃).

EXAMPLE 100

αR-amino-N-(1-methyl-3-phenylpropyl)propanamide

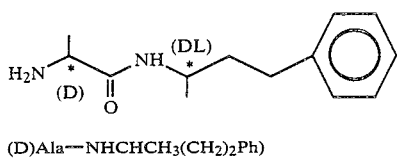

(D)Ala—NHCHCH₃(CH₂)₂Ph)

The title compound was prepared by the method of Example 9 substituting the product of Example 99 for the product of Example 8. The two diastereomers were separted by LPC on Porasil eluting with 1.5/98.4/0.1 MeOH/CHCl₃/NH₄OH.

Diastereomer DF: $[\alpha]_D -37.2°$; $-152.4°$ (365) CHCl₃.

NMR shift for the (D)Ala methyl and PPA α methyl = 1.29δ, J=0.9 Hz and 1.18δ, J=0.9 Hz (CDCl₃) respectively.

Diastereomer UF: $[\alpha]_D +41.2°$; $+186.1°$ (365) CHCl₃.

NMR shift of the (D)Ala methyl and PPA α methyl = 1.30δ, J=0.9 Hz and 1.19δ, J=0.9 Hz (CDCl₃).

EXANPLE 101

N-[(1,1-dimethylethoxy)carbonyl]-2,6-dimethyl-DL-tyrosyl-N-(1-methyl-3-phenylpropyl)-D-alaninamide, isomer UF

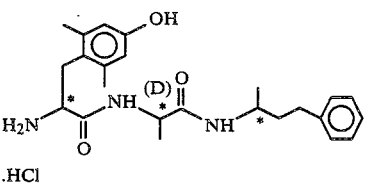

(Boc(DL)2,6Me₂Tyr—(D)Ala—NHCHCH₃(CH₂)₂Ph)

The title compounds were prepared from the UF diastereomer of Example 100 instead of the product of Example 44 using the method of Example 45. The UF-diastereomers were separated by LPC on porasil eluting with 1 to 2% MeOH/CH₂Cl₂.

These diastereomers were not purified further.

EXAMPLE 102

2,6-dimethyltyrosyl-N-(1S-methyl-3-phenylpropyl)-D-alaninamide, hydrochloride

UF isomer

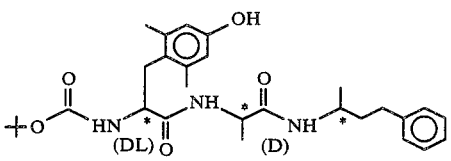

((D)2,6Me₂Tyr—(D)Ala—NHCHCH₃(CH₂)₂Ph.HCl)

The title product was prepared from the diastereomer of Example 101 with the greater TLC Rf using the method of Example 6.

Optical rotation $[\alpha]_D -41.4°$; $-184.2°$ (365) MeOH.
NMR shift for the (D)Ala methyl = 1.32δ (CD₃OD), NMR shift for the PPA α methyl = 1.16δ (CD₃OD).
Analysis Calcd. for $C_{24}H_{33}N_3O_3 \cdot 1\frac{1}{8}HCl \cdot \frac{1}{8}C_4H_8O_2 \cdot H_2O$ (MW=481.59): C, 61.10; H, 7.77; N, 8.73; Cl, 8.28.
Found: C, 60.91; H, 7.45; N, 8.84; Cl, 8.00.

EXAMPLE 103

2,6-dimethyltyrosyl-N-(1S-methyl-3-phenylpropyl)-D-alaninamide, hydrochloride

UF isomer

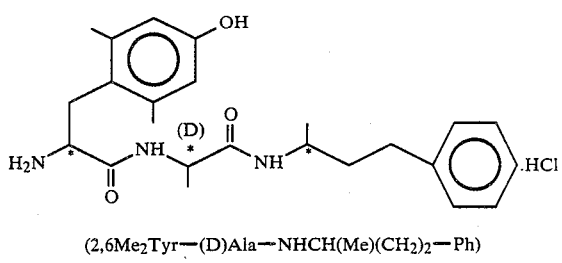

(2,6Me₂Tyr—(D)Ala—NHCH(Me)(CH₂)₂—Ph)

The title product was prepared from the diastereomer of Example 101 with the lesser TLC Rf using the method of Example 6.

Optical rotation $[\alpha]_D +111.7°$; $+421.9°$ (365) (MeOH).

NMR shift for the (D)Ala methyl = 1.06δ CD₃OD.
NMR shift for the PPA α methyl = 1.12δ CD₃OD.
Analysis Calcd. for $C_{24}H_{33}N_3O_3 \cdot 1\frac{1}{8}HCl \cdot \frac{1}{8}HCl \cdot \frac{1}{8}C_4H_8O_2 \cdot H_2O$ (MW=481.59): C, 61.10; H, 7.77; N, 8.83, Cl, 8.28. Found: C, 60.93; H, 7.28; N, 8.74; Cl, 8.00.

EXAMPLE 104

2-[2-(phenylthio)ethyl]-1H-isoindole-1,3(2H)-dione

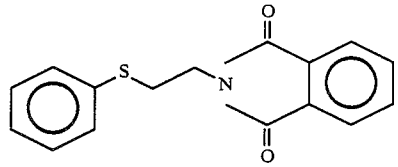

Potassium phthalimide (5.43 g, 25 mmol) was added to a DMF (50 ml) solution of [(2-bromoethyl)thio]benzene (5,43 g, 25 mmol) and this stirred mixture under N₂ was heated at 90° C. for 2 h. After cooling to room temperature, the reaction was filtered. The solvent was stripped from the filtrate under reduced pressure. The residue, dissolved in CH₂Cl₂ (100 ml), was filtered, concentrated, and flash chromotographed on a 4 inch column eluting with 1 to 6% EtOAc/toluene to produce 4.9 g of the title product.

Analysis Calcd. for $C_{16}H_{13}NO_2S$ (MW=283.34): C, 67.82; H, 4.62; N, 4.94; S, 11.31. Found: C, 67.92; H, 4.50; N, 5.00; S, 11.59.

EXAMPLE 105

2-(phenylthio)ethanamine

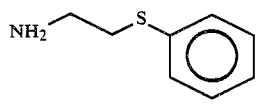

The title material was prepared from the title product of Example 103 by the method of Example 48.

Analysis Calcd. for $C_8H_{11}NS \cdot H_2O$ (MW=171.26): C, 56.10; H, 7.65; N, 8.18; S, 18.72. Found: C, 55.87; H, 7.30; N, 7.84; S, 18.20.

EXAMPLE 106

1,1-dimethylethyl [1R-methyl-2-oxo-2-[[2-(phenylthio)ethyl]amino]ethyl]-carbamate

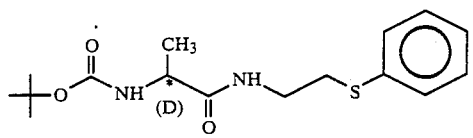

The title compound was prepared by the method of Example 1 using the title material from Example 105 in place of the amine hydrochloride of Example 1. One equivalent less of NMM was also used since the material of Example 105 was the free base. The product was used without further purification.

EXAMPLE 107

αR-amino-N-[2-(phenylthio)ethyl]propanamide, monohydrochloride

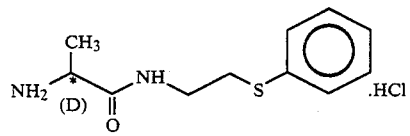

((D)Ala—NH(CH₂)₂SPh.HCl)

The title compound was prepared by the method of Example 2 from the title material of Example 106.

Optical rotation $[\alpha]_D +54.9°$ (MeOH).

NMR shift of the (D)Ala methyl=1.47δ (CD₃OD).

EXAMPLE 108

N-[(1,1-dimethylethoxy)carbonyl]-2,6-dimethyl-DL-tyrosyl-N-[2-(phenylthio)ethyl]-D-alaninamide

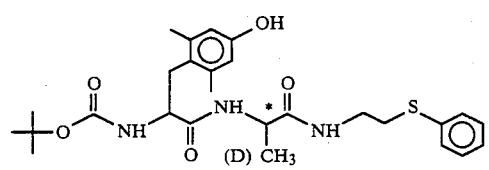

(Boc—(DL)2,6Me₂Tyr—(D)Ala—NH(CH₂)₂SPh)

The title mixture of diastereomers were prepared and separated by the method of Example 45 using the title material of Example 107 in place of the title amide of Example 44.

EXAMPLE 109

2,6-dimethyltyrosyl-N-[2-(phenylthio)ethyl]-D-alaninamide, monohydrochloride

DF Isomer

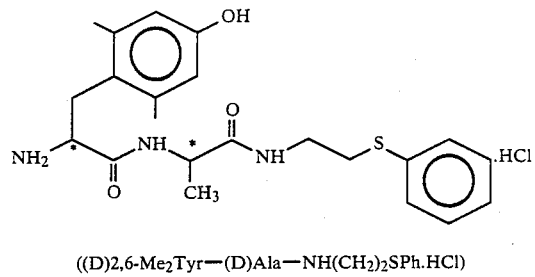

((D)2,6-Me₂Tyr—(D)Ala—NH(CH₂)₂SPh.HCl)

The title compound was synthesized from the DF diastereomer of Example 108 by the method of Example 6.

Optical rotation $[\alpha]_D -64.5°$ (MeOH).

NMR shift of the (D)Ala methyl=1.13δ (CD₃OD).

Analysis Calcd. for $C_{22}H_{29}N_3SO_3 \cdot HCl \cdot 1\frac{1}{2}H_2O$ (MW=479.05): C, 55.16; H, 6.94; N, 8.77; Cl, 7.40; S, 6.69. Found: C, 54.94; H, 6.49; N, 7.93; Cl, 7.43; S, 6.34.

EXAMPLE 110

2,6-dimethyltyrosyl-N-[2-(phenylthio)ethyl]-D-alaninamide, monohydrochloride

UF isomer

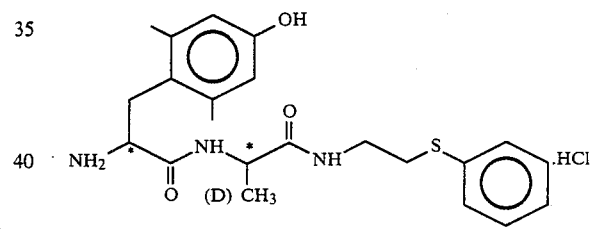

(2,6-Me₂Tyr—(D)Ala—NH(CH₂)₂SPh.HCl)

The title compound was prepared from the UF diastereomers of Example 108 by the method of Example 6.

Optical rotation $[\alpha]_D +109.5°$ (MeOH).

NMR shift of the (D)Ala methyl=0.88δ (CD₃OD).

Analysis Calcd. for $C_{22}H_{29}N_3SO_3 \cdot HCl \cdot H_2O$ (MW=470.04): C, 56.22; H, 6.86; N, 8.94; Cl, 7.54; S, 6.82. Found: C, 55.68; H, 6.49; N, 8.64; Cl, 7.94; S, 6.44.

EXAMPLE 111

2-(2-phenoxyethyl)-1H-isoindole-1,3(2H)-dione

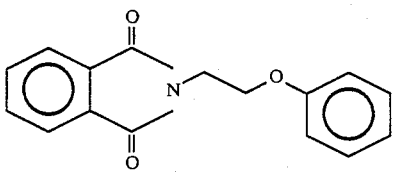

The title compound was prepared by the method of Example 104 using phenyl-O-CH₂CH₂Cl in place of phenyl-S-CH₂CH₂Br.

Analysis Calcd. for C$_{16}$H$_{13}$NO$_3$ (MW=267.30): C, 71.90; H, 4.90; N, 5.24. Found: C, 71.81; H, 4.69; N, 4.94.

EXAMPLE 112

2-phenoxyethanamine

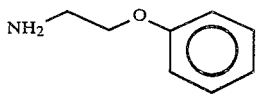

The title product was prepared from the title material of Example 111 by the method of Example 48 and used in subsequent reactions without further purification.

EXAMPLE 113

1,1-dimethylethyl ]1R-methyl-2-oxo-2-[(2-phenoxyethyl)amino]ethyl]carbamate

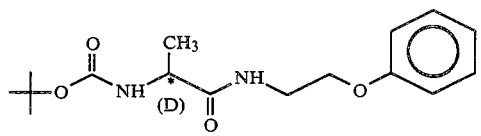

(Boc—(D)Ala—NH(CH$_2$)$_2$OPh)

The title compound was prepared by the method of Example 1 using the title material from Example 112 in place of the amine hydrochloride of Example 1. One equivalent less of NMM was also used since the material of Example 112 was the free base. The product was used without further purification.

EXAMPLE 114

αR-amino-N-(2-phenoxyethyl)propanamide, monohydrochloride

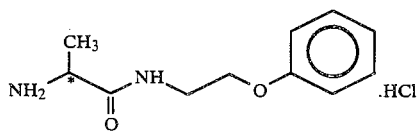

((D)Ala—NH(CH$_2$)$_2$OPh.HCl)

The title compound was prepared by the method of Example 2 from the title material of Example 113.
Optical rotation [α]$_D$−2.0° (MeOH).
NMR shift of the (D)Ala methyl=1.47δ (CD$_3$OD).
Analysis Calcd. for C$_{11}$H$_{17}$N$_2$O$_2$Cl (MW=244.72): C, 53.99; H, 7.00; N, 11.45; Cl, 14.49. Found: C, 53.61; H, 6.99; N, 11.17; Cl, 14.43.

EXAMPLE 115

N-[(1,1-dimethylethoxy)carbonyl]02,6-dimethyl-DL-tyrosyl-N-(2-phenoxyethyl)-D-alaninamide

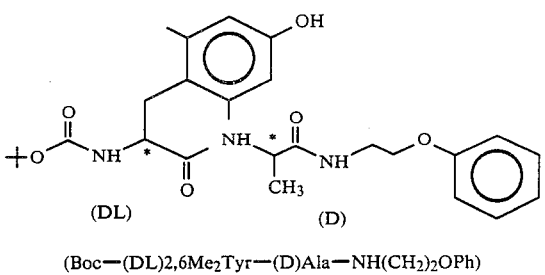

(Boc—(DL)2,6Me$_2$Tyr—(D)Ala—NH(CH$_2$)$_2$OPh)

The title mixture of diastereomers were prepared and separated by the method of Example 45. using the title material of Example 114 in place of the title amide of Example 44.

EXAMPLE 116

2,6-dimethyltyrosyl-N-(2-phenyoxyethyl)-D-alaninamide, hydrochloride

DF isomer

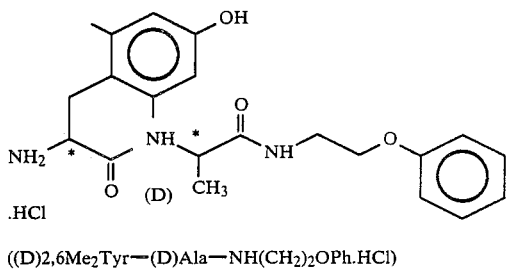

((D)2,6Me$_2$Tyr—(D)Ala—NH(CH$_2$)$_2$OPh.HCl)

The title compound was synthesized from the DF diastereomer of Example 115 by the method of Example 6.
Optical rotation [α]$_D$−52.5° (CH$_3$OH).
NMR shift of the (D)Ala methyl=1.26δ (CD$_3$OD).
Analysis Calcd. for C$_{22}$H$_{29}$N$_3$O$_4$.1⅛HCl.1¼H$_2$O (MW=463.03): C, 57.07; H, 7.10; N, 9.08; Cl, 8.61. Found: C, 56.77; H, 6.73; N, 8.70; Cl, 8.34.

EXAMPLE 117

UF isomer 2,6-dimethyltyrosyl-N-(2-phenoxyethyl)-D-alaninamide, monohydrochloride, isomer UF

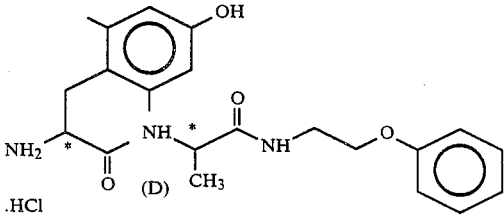

(2,6Me$_2$Tyr—(D)Ala—NH(CH$_2$)$_2$OPh.HCl)

The title compound is synthesized from the UF diastereomer of Example 115 by the method of Example 6.

EXAMPLE 118

2-[3-[4-(dimethylamino)phenyl]propyl]-1H-isoindole-1,3(2H)-dione

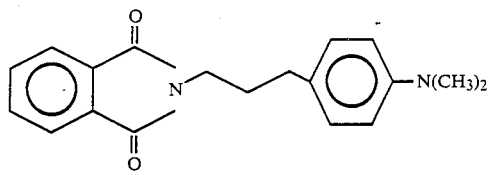

The title compound was prepared by hydrogenation of 2-[3-[4-(dimethylamino)phenyl]-2E-propenyl]-qH-isoindole-1,3(2H)-dione in THF at 5 psi and ambient temperature using 5% Pd/C as catalyst. After the reaction mixture was filtered and concentrated, the title compound was used without further purification.

EXAMPLE 119

4-(dimethylamino)benzenepropanamine

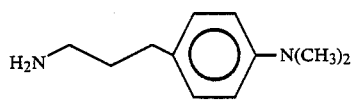

The title compound was prepared from the product of Example 118 using the method of Example 48.

EXAMPLE 120 phenylmethyl [2-[[3-[4-(dimethylamino)phenyl]propyl]amino]-1R-methyl-2-oxoethyl]carbamate

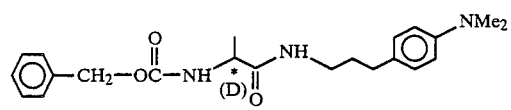

(Z—(D)Ala—NH(CH₂)₃—(4-Me₂N)Ph)

The title compound was prepared by the method of Example 8 where the product of Example 119 was substituted for the 6-amino hexanoic acid methyl ester. The title compound was purified by PLC on Woelm® silical gel eluting with 2/98/0.2EtOH/CH₂Cl₂/N-H₄OH.

NMR shift of the (D)ala methyl=1.32δ (CDCl₃).

Example 121

αR-amino-N-[3-[4-(dimethylamino)phenyl]propyl]-propanamide

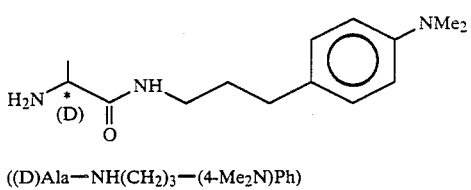

((D)Ala—NH(CH₂)₃—(4-Me₂N)Ph)

The title compound was prepared by hydrogenation of the product from Example 120 in THF at ambient temperature and 60 psi using 5% Pd/C as catalyst. The reaction mixture was filtered and concentrated. The resultant title product oil was used without further purification.

NMR shift of the (D)Ala methyl=1.28δ (CDCl₃).

EXAMPLE 122

N-[(1,1-dimethylethoxy)carbonyl]-2,6-dimethyl-DL-tyrosyl-N-[3-[4-(dimethylamino)phenyl]propyl]-D-alaninamide

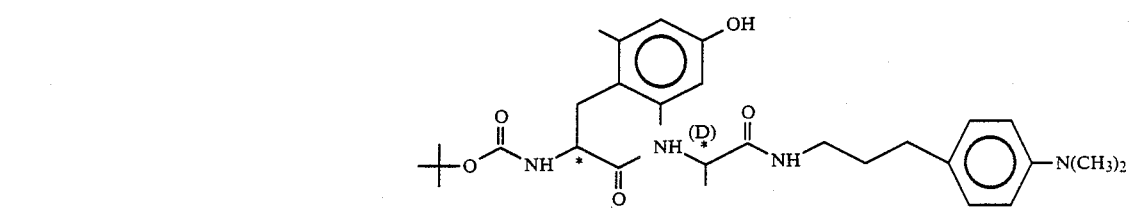

(Boc—(DL)2,6Me₂Tyr—(D)Ala—NH(CH₂)₃—(4-Me₂N)Ph)

The title compound was prepared by the method of Example 45 using the product of Example 121 in place of the C-terminal amino acid amide used in Example 45. The reaction mixture of diastereomers was purified by PCL on Porasil eluting with 5/95:MeOH/CH₂Cl₂.

EXAMPLE 123

2,6-dimethyl-DL-tyrosyl-N-[3-[4-(dimethylamino)phenyl]propyl]-D-alaninamide,·dihydrochloride

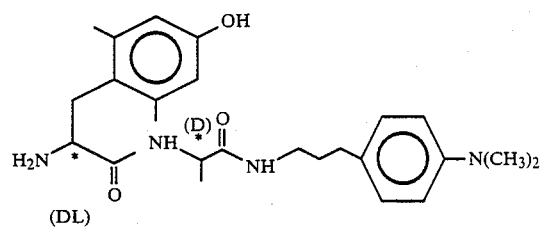

((DL)2,6Me₂Tyr—(D)Ala—NH(CH₂)₃—(4-Me₂N)Ph.HCl)

The title compound was prepared from the diastereomeric mixture of Example 122 by the method of Example 6.

NMR shift of the (D)Ala methyls=0.87δ+1.14δ (DMSOd₆).

Optical rotation [α]_D +29.0°; +91.0° (365) MeOH.

Analysis calcd. for C$_{25}$H$_{36}$N$_4$O$_3$2HCl.1⅜H$_2$O (MW=538.28): C, 55.78; H, 7.63; N, 10.41, Cl, 13.17. Found: C, 56.06; H, 7.23; N, 10.10, Cl, 12.81.

EXAMPLE 124

N-[(1,1-dimethylethoxy)carbonyl]-2,6-dimethyl-DL-tyrosyl-N-(1-methyl-3-phenylpropyl)-D-alaninamide DF isomer

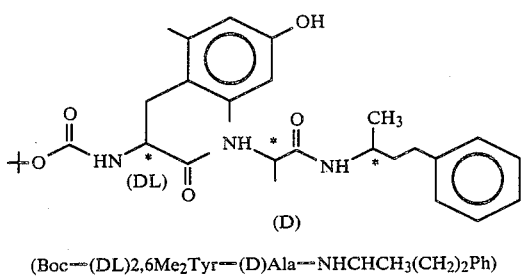

(Boc—(DL)2,6Me$_2$Tyr—(D)Ala—NHCHCH$_3$(CH$_2$)$_2$Ph)

The title compounds were prepared from the DF diastereomer of Example 100 instead of the product of Example 44 using the method of Example 45.

EXAMPLE 125

2,6-dimethyl-DL-tyrosyl-N-(1-methyl-3-phenylpropyl)-D-alaninamide hydrochloride

DF isomer

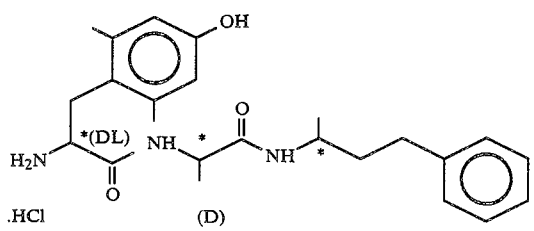

((DL)2,6Me$_2$Tyr—(D)Ala—NHCHCH$_3$(CH$_2$)$_2$Ph.HCl)

The title products were prepared from the product of Example 124 using the method of Example 6.

Optical rotation [α]$_D$+33.5°; +108.8° (365) MeOH.

NMR shift of the (D)Ala methyl=1.31+1.39δ (CDCl$_3$).

NMR shift of the PPA α methyl=1.17δ (CDCl$_3$).

Analysis calcd. for C$_{24}$H$_{33}$N$_3$O$_3$ (MW=411.55): C, 70.04; H, 8.08; N, 10.21. Found: C, 69.97; H, 7.92; N, 10.17.

EXAMPLE 126 methyl 4-[3-[[1-oxo-2R-[[(phenylmethoxy)carbonyl]amino]-propyl]amino]-1E-propenyl]benzoate

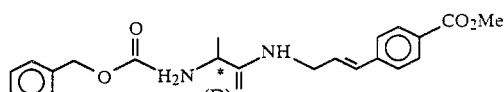

(Z—(D)Ala—NHCH$_2$(CH)$_2$—(4-CO$_2$Me)Ph)

The title compound was prepared by the method of Example 8 where methyl 4-(3-amino-1E-propenyl)benzoate was substituted for the NH$_2$2Ad.HCl using one less equivalent of NMM.

EXAMPLE 127 methyl 4-[3-[(2R-amino-1-oxopropyl)amino]propyl]benzoate

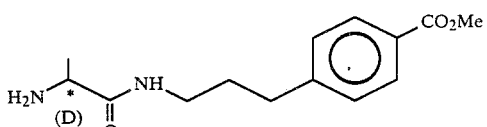

(D)Ala—NHCH$_2$(CH)$_2$—(4-CO$_2$Me)Ph)

The title product was obtained by hydrogenation of the product of Example 126 using the method described in Example 95.

NMR shift of the (D)Ala methyl=1.31δ (CDCl$_3$).

EXAMPLE 128

N-[(1,1-dimethylethoxy)carbonyl]-2,6-dimethyl-DL-tyrosyl-N-[3-[4-methoxycarbony)phenyl]propyl]-D-alaninamide

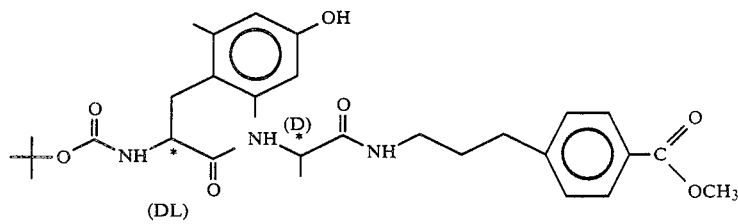

(Boc—(DL)2,6Me$_2$Tyr—(D)Ala—NH(CH$_2$)$_3$(4-CO$_2$Me)Ph)

The title mixture of diastereomers was prepared by the method of Example 45 using the product of Example 127 as the C-terminal unit. The reaction mixture was purified by PLC on Woelm® silica eluting with 2/97.85/0.15MeOH/CH$_2$Cl$_2$/NH$_4$OH.

Example 129

2,6-dimethyl-DL-tyrosyl-N-[3-[4-(methoxycarbony)-phenyl]propyl-D-alaninamide, monohydrochloride

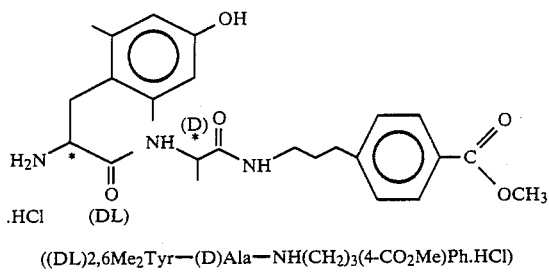

((DL)2,6Me₂Tyr—(D)Ala—NH(CH₂)₃(4-CO₂Me)Ph.HCl)

The title compound was prepared from the diastereomer mixture of Example 128 using the method of Example 6.

NMR shift of the (D)Ala methyl=1.05δ+1.27δ (CD₃OD).

Optical rotation [α]$_D$+20.0°; +74.3° (365) MeOH.

Analysis Calcd. for $C_{25}H_{33}N_3O_5.HCl.\frac{1}{2}H_2O$ (MW=501.02): C, 59.93; H, 7.04; N, 8.39; Cl, 7.08. C, 59.85; H, 7.07; N, 8.39; Cl, 7.10.

EXAMPLE 130

2-[3-(5-pyrimidinyl)propyl]-1H-isoindole-1,3(2H)-dione

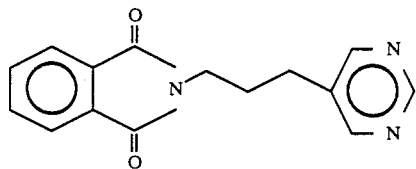

The title compound was prepared by hydrogenation of 2-[3-(5-pyrimidinyl)-2E-propenyl]-1H-isoindole-1,3-(2H)-dione using the method of Example 118.

EXAMPLE 131

5-pyrimidinepropanamine

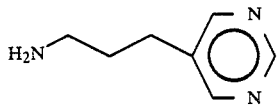

The title compound was prepared from the product of Example 130 using the method of Example 48.

EXAMPLE 132

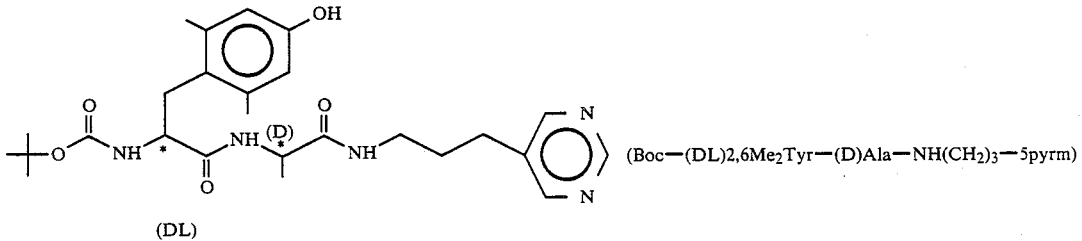

(Boc—(DL)2,6Me₂Tyr—(D)Ala—NH(CH₂)₃—5pyrm)

The title compound was prepared from the product of Example 131 using the method of Example 18. The diastereomers were separated by gradient PLC on Woelm ® silica eluting with MeOH/CH₂Cl₂/NH₄OH ratios of 2/97.85/0.15 to 5/94.6/0.40.

Diastereomer DF: NMR shift of the (D)Ala methyl=1.21δ (DMSOd₆).

Diastereomer UF: NMR shift of the (D)Ala methyl=0.98δ (DMSOd₆).

EXAMPLE 133

2,6-dimethyl-D-tyrosyl-N-[3-(5-pyrimidinyl)propyl]-D-alaninamide, dihydrochloride DF isomer

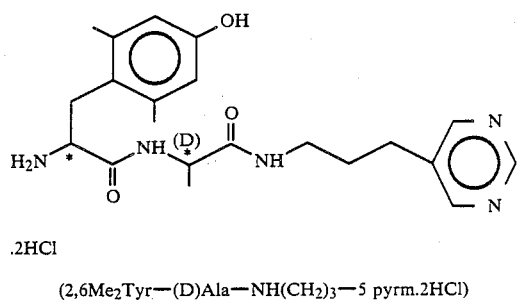

(2,6Me₂Tyr—(D)Ala—NH(CH₂)₃—5 pyrm.2HCl)

The title product was prepared from the DF-diastereomer of Example 132 by the method of Example 6.

NMR shift of the (D)Ala methyl=1.15δ (DMSOd₆).

Optical rotation [α]$_D$−62.3°; −209.3° (365) MeOH.

Analysis calcd. for $C_{21}H_{29}N_5O_3.2HCl.1\frac{1}{4}H_2O$ (MW=494.94): C, 50.96; H, 6.82; N, 14.15; Cl, 14.32 Found: C, 50.76; H, 6.66; N, 14.19; Cl, 14.39.

EXAMPLE 134

2,6-dimethyl-L-tyrosyl-N-[3-(5-pyrimidinyl)propyl]-D-alaninamide, dihydrochloride UF isomer

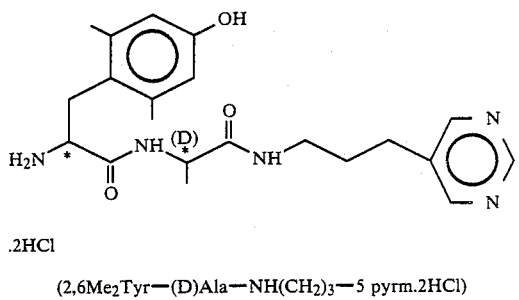

(2,6Me₂Tyr—(D)Ala—NH(CH₂)₃—5 pyrm.2HCl)

The title compound was prepared from the UF-diastereomer of Example 133 by the method of Example 6.

NMR shift of the (D)Ala methyl=1.04δ (CD₃OD).

Optical rotation $[\alpha]_D +89.5°$; $+332.4°$ (365) MeOH.
Analysis calcd. for $C_{21}H_{29}N_5O_3 \cdot 2HCl \cdot \frac{5}{8}H_2O$ (MW=483.68): C, 52.15, H, 6.72, N, 14.48, Cl, 14.66. Found: C, 52.45, H, 6.54, N, 14.56, Cl, 14.24.

EXAMPLE 135

2-[3-(4-fluorophenyl)-2E-propenyl]-1H-isoindole-1,3(2H)-dione

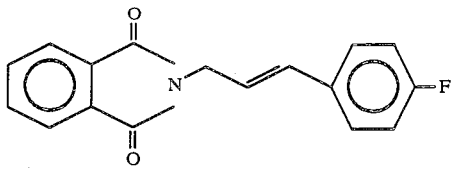

N-Allylphthalimide (13.9 g, 74.3 mmol), 1-fluoro-4-iodobenzene (15.0 g, 67.6 mmol) triethylamine (15.0 g, 148 mmol) and Pd(OAc)₂ (152 mg) were heated at 104° in a glass bomb with shaking for 18 h under an inert atmosphere. The reaction mixture was dissolved in hot acetonitrile. The catalyst was removed by filtration and the filtrate cooled to 0°. The precipitated white solid product was filtered off and dried under vacuum. This title material (12.55 g) was used without further purification.

EXAMPLE 136

3-(4-fluorophenyl)-2E-propen-1-amine

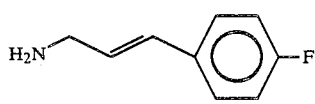

The title compound was prepared from the product of Example 135 using the method of Example 48.

EXAMPLE 137 phenylmethyl [2-[[3-(4-fluorophenyl)propyl]amino]-1R-methyl-2-oxo-ethyl[carbamate

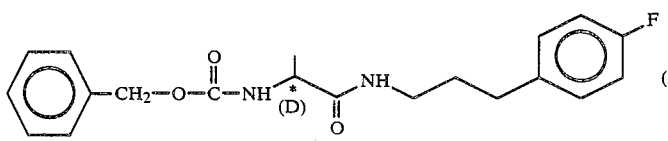

The title compound was prepared from the product of Example 136 using the method of Example 8. The title compound was purified by PLC on Porasil eluting with 20/80 EtOAc/CH₂Cl₂.

NMR shift of the (D)Ala methyl=1.38δ (DMSOd₆).

EXAMPLE 138

αR-amino-N-[3-(4-fluorophenyl)propyl]propanamide

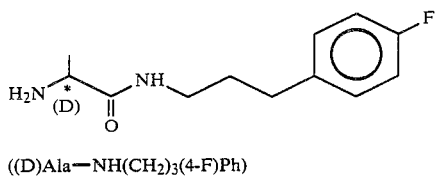

((D)Ala—NH(CH₂)₃(4-F)Ph)

The title compound was prepared by hydrogenation of the product from Example 137 using the method of Example 121.

NMR shift of the (D)Ala methyl=1.32δ (CDCl₃).

EXAMPLE 139

N-[(1,1-dimethylethoxy)carbonyl]-2,6-dimethyl-DL-tyrosyl-N-[3-(4-fluorophenyl)propyl]-D-alaninamide

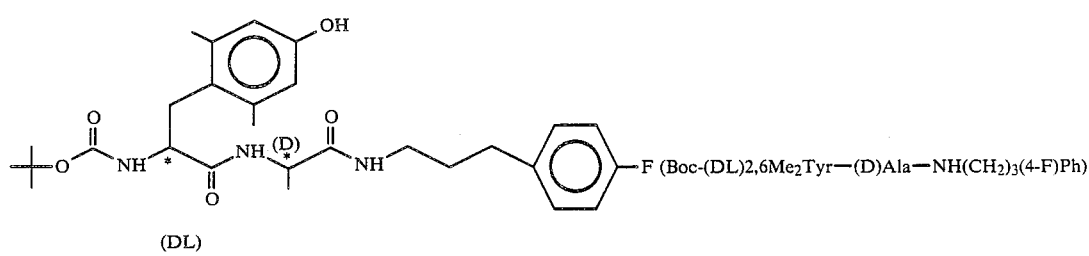

The title diastereomers were prepared by the method of Example 45 using the product of Example 138 as the C-terminal unit. The diastereomers were separated by PLC on Woelm® silica eluting with 2.5/97.3/0.2 MeOH/CH₂Cl₂/NH₄OH.

Diastereomer DF: NMR shift of the (D)ala methyl=1.18δ (DMSOd₆).

Diastereomer UF: NMR shift of the (D)ala methyl=0.99δ (DMSOd₆).

EXAMPLE 140

2,6-dimethyl-D-tyrosyl-N-[3-(4-fluorophenyl)propyl]-D-alaninamide, hydrochloride DF isomer

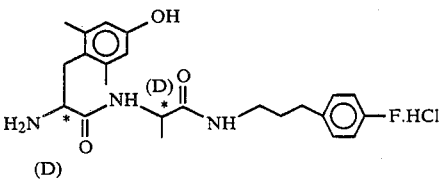

(2,6Me₂Tyr—(D)Ala—NH(CH₂)₃(4-F)Ph.HCl)

The title compound was prepared from the DF-diastereomer of Example 139 by the method of Example 6.

NMR shift of the (D)ala methyl=1.16δ (DMSOd6).
Optical rotation [α]$_D$ −52.4°; −181.9° (365) MeOH.
Analysis calcd. for C$_{23}$H$_{30}$FN$_3$O$_3$.1⅛HCl.¼H$_2$O (MW=461.03): C, 59.92; H, 6.91; N, 9.11; Cl, 8.65; F, 4.12. Found: C, 59.81; H, 6.81; N, 9.02; Cl, 8.62; F, 4.09.

EXAMPLE 141

2,6-dimethyl-L-tyrosyl-N-[3-(4-fluorophenyl)propyl]-D-alaninamide, hydrochloride UF isomer

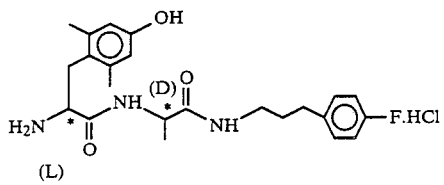

(2,6Me$_2$Tyr—(D)Ala—NH(CH$_2$)$_3$(4-F)Ph.HCl)

The title compound was prepared from the UF-diastereomer of Example 139 by the method of Example 6.

NMR shift of the (D)Ala methyl=0.90δ (DMSOd6). (365) MeOH.

Optical rotation [α]$_D$+99.5°, +377.6° (365) MeOH.

Analysis calcd. for C$_{23}$H$_{30}$FN$_3$O$_3$.1⅛HCl.¾H$_2$O (MW=470.04): C, 58.77; H, 7.00; N, 8.94; Cl, 8.49; F, 4.04. Found: C, 59.01; H, 6.83; N, 8.65; Cl, 8.09; F, 4.45.

EXAMPLE 142 phenylmethyl [2-[[3-(4-hydroxyphenyl)-2E-propenyl]amino]-1R-methyl-2-oxoethyl]carbamate

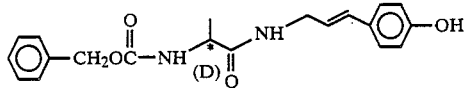

(Z—(D)Ala—NHCH$_2$(CH)$_2$—(4-OH)Ph)

The title compound was prepared by the method of Example 8 where 4-(3-amino-1E-propenyl)phenol was substituted for the NH$_2$2Ad.HCl using one less equivalent of NMM.

EXAMPLE 143

αR-amino-N-[3-(4-hydroxyphenyl)propyl]propenamide

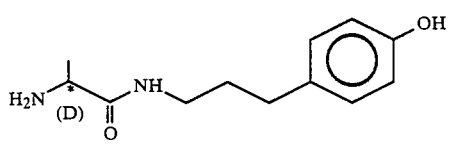

((D)Ala—NH(CH$_2$)$_3$(4-OH)Ph)

The title compound was obtained by hydrogenation of the product of Example 142 using the method of Example 95.

EXAMPLE 144

N-[(1,1-dimethylethoxy)carbonyl]-2,6-dimethyl-DL-tyrosyl-N-[3-(4-hydroxyphenyl)propyl]-D-alaninamide

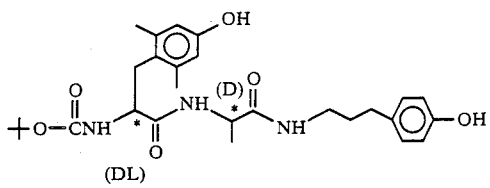

(Boc(DL)2,6Me$_2$Tyr(D)Ala—NH(CH$_2$)$_3$(4-OH)Ph)

The title diastereomers were prepared by the method of Example 45 using the product of Example 143 as the C-terminal unit. The diastereomers were separated by PLC on Woelm® silica eluting with 5/94.6/0.4; MeOH/CHCl$_3$/NH$_4$OH.

Diastereomer DF: NMR shift of the (D)Ala methyl=1.18δ (DMSOd6)

Diastereomer UF: NMR shift of the (D)Ala methyl=1.00δ (DMSOd6)

EXAMPLE 145

2,6-dimethyl-D-tyrosyl-N-[3-(4-hydroxyphenyl)propyl]-D-alaninamide, hydrochloride DF isomer

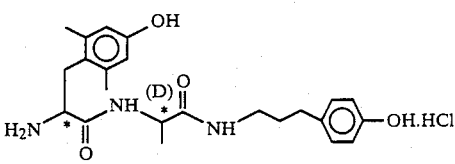

(2,6Me$_2$Tyr—(D)Ala—NH(CH$_2$)$_3$(4-OH)Ph.HCl)

The title compound was prepared from the DF diastereomer of Example 144 by the method of Example 6.

NMR shift of the (D)ala methyl=1.15δ (DMSOd6).

Optical rotation [α]$_D$ −47.6°, −190.5° (365) MeOH.

Analysis calcd. for C$_{23}$H$_{31}$N$_3$O$_4$.1⅛HCl.¾H$_2$O (MW=468.05): C, 59.02; H, 7.24; N, 8.98; Cl, 8.52. Found: C, 58.64; H, 6.84; N, 8.85; Cl, 8.12.

EXAMPLE 146

2,6-dimethyl-L-tyrosyl-N-[3-(4-hydroxyphenyl)propyl]-D-alaninamide, hydrochloride UF isomer

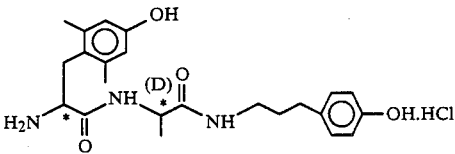

(2,6Me$_2$Tyr—(D)Ala—NH(CH$_2$)$_3$(4-OH)Ph.HCl)

The title compound was prepared from the UF diastereomer of Example 144 by the method of Example 6.

NMR shift of the (D)Ala methyl=0.86δ (DMSOd6).
Optical rotation [α]$_D$+95.6°; +363.7° (365) MeOH.

Analysis calcd. for C₂₃H₃₁N₃O₄.1⅛HCl.H₂O (MW=472.55); C, 58.46; H, 7.28; N, 8.89; Cl, 8.44. Found: C, 58.84; H, 6.89; N, 8.87; Cl, 8.19.

EXAMPLE 147 phenylmethyl [2-[[2-(9H-fluoren-9-yl)ethyl]amino-1R-methyl-2-oxoethyl]carbamate

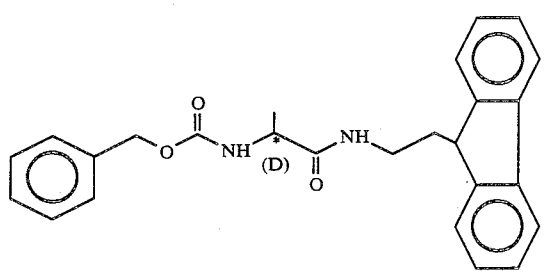

(Z—(D)Ala—NH(CH₂)₂—9-Fluorene)

The title compound was prepared by the method of Example 8 where 9H-fluoren-9-yl-ethanamine was substituted for the 6-aminohexanoic acid methyl ester. The title compound was purified by PLC on silica gel using 1.5% 2-propanol/CH₂Cl₂.

EXAMPLE 148

αR-amino-N-[2-(9H-fluoren-9-yl)ethyl]propanamide

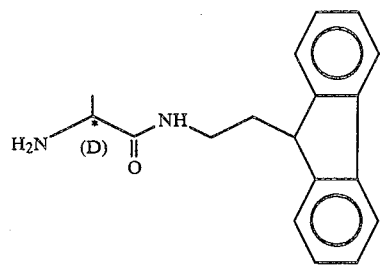

((D)Ala—NH(CH₂)₂—9-Flourene)

The title product was obtained by hydrogenation of the product of Example 147 using the method of Example 9.

EXAMPLE 149

N-[(1,1-dimethylethoxy)carbonyl]-2,6-dimethyl-DL-tyrosyl-N-[2-(9H-fluoren-9-yl)ethyl]-D-alaninamide

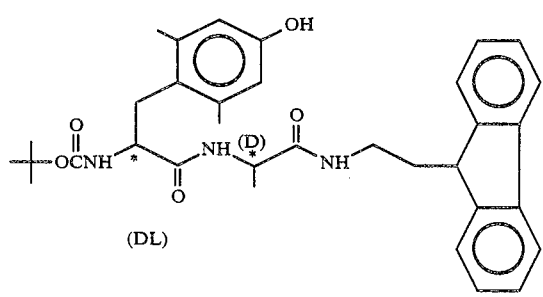

(Boc—(DL)2,6Me₂Tyr—(D)Ala—NH(CH₂)₂—9-Fluorene)

The title product was prepared by the method of Example 45 using the product of Example 148 as the C-terminal coupling fragment. The diastereomers were separated by PLC on Woelm® silica eluting with 2% to 7% 2-propanol (with 7% NH₄OH)/toluene.

EXAMPLE 150

2,6-dimethyl-D-tyrosyl-N-[2-(9H-fluoren-9-yl)ethyl]-D-alaninamide, monohydrochloride DF isomer

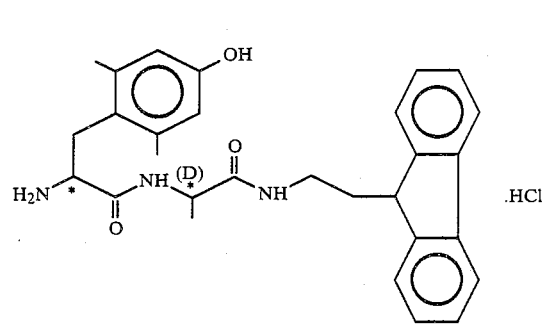

(2,6Me₂Tyr—(D)Ala—NH(CH₂)—9-Fluorene.HCl)

The title compound was prepared from the DF-diastereomer of Example 149 by the method of Example 6.
NMR shift of the (D)Ala methyl=1.12δ (DMSOd₆).
Optical rotation [α]$_D$−20.9°; −34.5° (365) MeOH.
Analysis calcd. for C₂₉H₃₃N₃O₃.HCl.1¼H₂O (MW=530.58): C, 65.65; H, 6.93; N, 7.92; Cl, 6.68. Found: C, 65.50; H, 6.54; N, 7.78; Cl, 6.48.

EXAMPLE 151

2,6-dimethyl-L-tyrosyl-N-[2-(9H-fluoren-9-yl)ethyl]D-alaninamide, hydrochloride

UF isomer

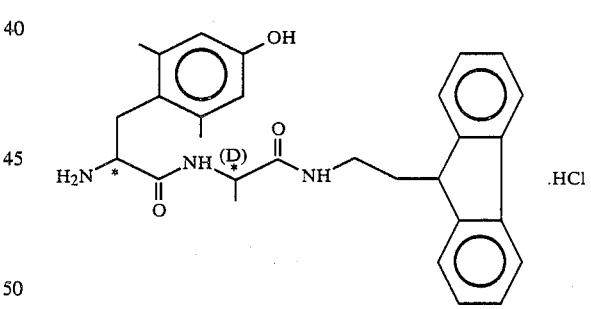

The title compound was prepared from the UF-diastereomer of Example 149 by the method of Example 6.
NMR shift of the (D)ala methyl=0.89δ (DMSOd₆).
Optical rotation [α]$_D$+127.7°; +424.7° (365) MeOH.
Analysis calcd. for C₂₉H₃₃N₃O₃.1-⅛HCl.¼H₂O (MW=517.12): C, 67.36; H, 6.75; N, 8.13; Cl, 7.71. Found: C, 67.13; H, 6.57; N, 8.15; Cl, 7.41.

EXAMPLE 152

(3-bromo-1-propynyl)benzene

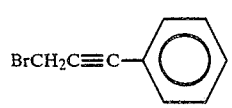

The 1-phenylpropargyl bromide was prepared by adding phosphorous tribromide (46.7 g, 172.5 mmol) dropwise to a stirred solution of 1-phenylpropargyl alcohol (60 g, 450 mmol) in anhydrous Et₂O (300 ml). The reaction mixture was heated for 2 h at reflex; and the poured onto ice. The organic layer was separated, dried over MgSO₄ and stripped of solvent to obtain the product oil. This material was used without further purification.

EXAMPLE 153

2-(3-phenyl-2-propynyl)-1H-isoindole-1,3(2H)-dione

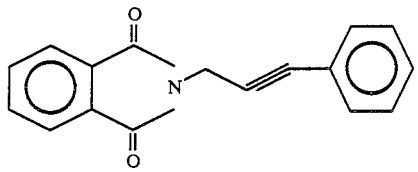

The title compound was prepared by stirring a mixture of the product (450 mmol) from Example 152 and potassium phthalimide (83 g, 450 mmol) in dimethylformamide (DMF, 600 ml) for 16 h. The reaction mixture was poured into water and the resulting solid was filtered off. This title compound was washed with H₂O and Et₂O before being dried under vacuum. The product (107 g) was used without further purification.

EXAMPLE 154

3-phenyl-2-propyn-1-amine

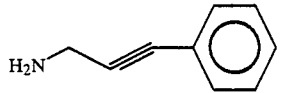

The title product was prepared from the product of Example 153 using the method of Example 48.

EXAMPLE 155

1,1-dimethylethyl [1R-methyl-2-oxo-2-[(3-phenyl-2-propynyl)amino]ethyl]carbamate

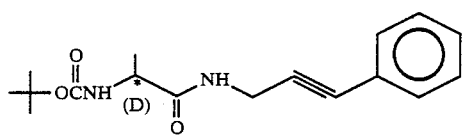

(Boc—(D)Ala—NHCH₂C≡CPh)

The title compound was prepared from the product of Example 154 by the method of Example 1 using one equivalent less of NMM.

NMR shift of the (D)Ala methyl=1.39δ (CDCl₃).

EXAMPLE 156

αR-amino-N-(3-phenyl-2-propynyl)propanamide, monohydrochloride

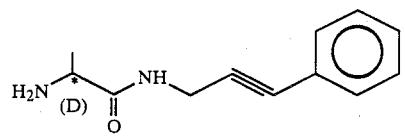

((D)Ala—NHCH₂C≡CPh.HCl)

The title compound was prepared from the title compound of Example 155 by the method of Example 2.
NMR shift of the (D)Ala methyl=1.40δ (DMSOd₆).
Optical rotation [α]_D −9.3°; −22.3° (365) MeOH.
Analysis calcd. for C₁₂H₁₄N₂O.HCl.9/16H₂O (MW=248.85): C, 57.92; H, 6.53; N, 11.26; Cl, 14.25. Found: C, 57.60; H, 6.27; N, 11.36; Cl, 14.61.

The free base of the title compound was formed and isolated by the method of Example 44.

EXAMPLE 157

N-[(1,1-dimethylethoxy)carbonyl]-2,6-dimethyl-DL-tyrosyl-N-(3-phenyl-2-propynyl)-D-alaninamide

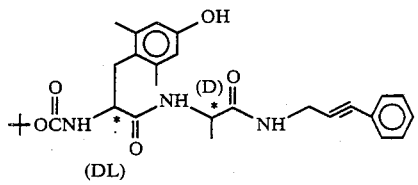

(Boc—(DL)2,6Me₂Tyr—(D)Ala—NHCH₂C≡CPh)

The title mixture of diastereomers was prepared from the free base of the title product of Example 156 by the method of Example 45. The diastereomers were separated by PLC on Woelm® silica eluting with 2.5/97.3/0.2; MeOH/CHCl₃/NH₄OH.

Diastereomer DF: NMR shift of the (D)Ala methyl=1.21δ (DMSOd₆).
Diastereomer UF: NMR shift of the (D)Ala methyl=1.03δ (DMSOd₆).

EXAMPLE 158

2,6-dimethyl-D-tyrosyl-N-(3-phenyl-2-propynyl)-D-alaninamide, hydrochloride

DF isomer

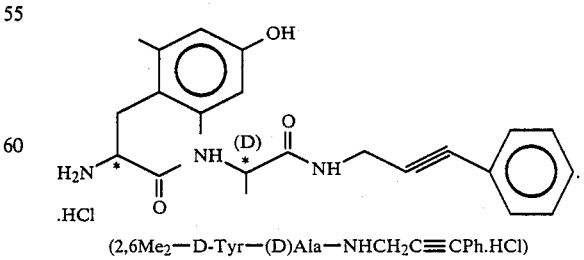

(2,6Me₂—D-Tyr—(D)Ala—NHCH₂C≡CPh.HCl)

The title compound was prepared from the DF-diastereomer of Example 157 by the method of Example 6.
NMR shift of the (D)Ala methyl=1.25δ (DMSOd₆).

Optical rotation $[\alpha]_D -58.5°$; $-218.5°$ (365) MeOH.
Analysis calcd. for $C_{23}H_{27}N_3O_3 \cdot 1\frac{1}{8}HCl \cdot 1\frac{7}{8}H_2O$ (MW=450.27): C, 61.35; H, 6.69; H, 9.33; Cl, 8.86. Found: C, 61.36; H, 6.37; N, 9.24; Cl, 8.68.

EXAMPLE 159

2,6-dimethyl-L-tyrosyl-N-(3-phenyl-2-propynyl)-D-alaninamide, monohydrochloride UF isomer

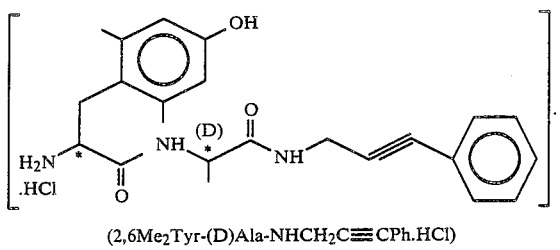

(2,6Me$_2$Tyr-(D)Ala-NHCH$_2$C≡CPh.HCl)

The title compound was prepared from the UF-diastereomer of Example 157 by the method of Example 6. NMR shift of the (D)Ala methyl=0.88δ (DMSOd$_6$). Optical rotation $[\alpha]_D +90.2°$; $+352.6°$ (365) MeOH.
Analysis calcd. for $C_{23}H_{27}N_3O_3 \cdot HCl \cdot H_2O$ (MW=447.91): C, 61.67; H, 6.75; N, 9.38; Cl, 7.91. Found: C, 61.84; H, 6.36; N, 9.26; Cl, 8.22.

EXAMPLE 160

2-(3-phenyl-2Z-propenyl)-1H-isoindole-1,3(2H)-dione

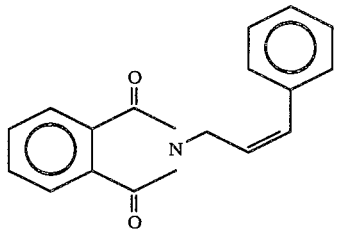

The title compound was prepared from the title product (15 g, 57.4 mmol) of Example 153 by hydrogenation using Lindlar catalyst (2.25 g) and quinoline (0.79 g, 6.09 mmol) in THF (150 ml). The reaction mixture was hydrogenated at 5 psi and 0° to obtain a quantitative yield of the cis product.

NMR: CH$_2$=4.51δ, 2H; vinyl=5.40 to 5.58δ, H, 6.45 to 5.80δ 1H.

EXAMPLE 161

3-phenyl-2Z-propen-1-amine

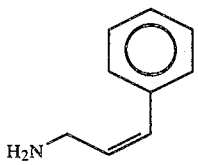

The title compound was prepared from the product of Example 160 using the method of Example 48.

EXAMPLE 162

1,1-dimethylethyl[1R-methyl-2-oxo-2-[(3-phenyl-2Z-propenyl)amino]ethyl]carbamate

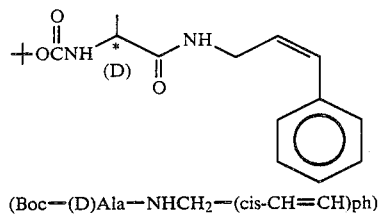

(Boc—(D)Ala—NHCH$_2$—(cis-CH=CH)ph)

The title compound was prepared from the product of Example 161 by the method of Example 1 using one equivalent less of NMM. The title compound was purified by PLC on Woelm ® silica eluting with 12% EtOAc/CH$_2$Cl$_2$.

NMR shift of the (D)Ala methyl=1.32δ (CDCl$_3$).

EXAMPLE 163

αR-amino-N-(3-phenyl-2Z-propenyl)propanamide

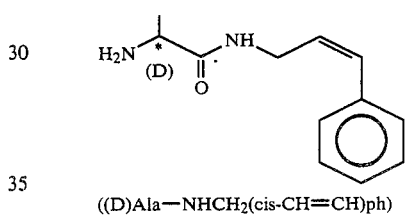

((D)Ala—NHCH$_2$(cis-CH=CH)ph)

The title compound was prepared from the product of Example 162 by the method of Example 2. The free base was formed and isolated by the method of Example 44.

EXAMPLE 164

N-[(1,1-dimethylethoxy)carbonyl]-2,6-dimethyl-DL-tyrosyl-N-(3-phenyl-2Z-propenyl)-D-alaninamide

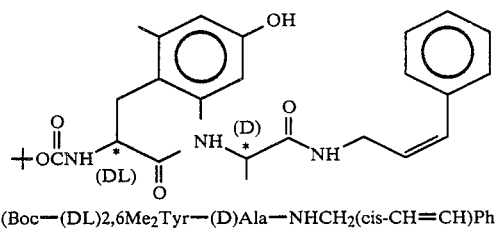

(Boc—(DL)2,6Me$_2$Tyr—(D)Ala—NHCH$_2$(cis-CH=CH)Ph)

The title mixture of disastereomers was prepared from the title product of Example 163 by the method of Example 45. The diastereomers were separated by PLC on Woelm ® silica using a gradient elution from 1% to 4% MeOH/CH$_2$Cl$_2$.

Diastereomer DF: NMR shift of the (D)Ala methyl=1.19δ (DMSOd$_6$).

Diastereomer UF: NMR shift of the (D)Ala methyl=B 1.00δ (DMSOd$_6$).

EXAMPLE 165

2,6-dimethyl-D-tyrosyl-N-(3-phenyl-2Z-propenyl)-D-alaninamide, hydrochloride

DF isomer

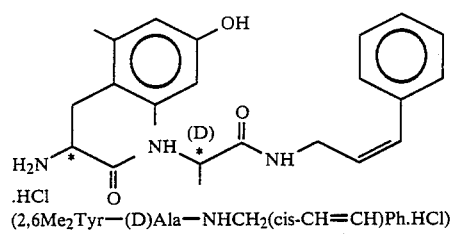

(2,6Me₂Tyr—(D)Ala—NHCH₂(cis-CH=CH)Ph.HCl)

The title compound was prepared from the DF-diastereomer of Example 164 by the method of Example 6. NMR shift of the (D)Ala methyl=1.15δ (DMSOd₆).

Optical rotation $[\alpha]_D$ −65.6°; −288.2° (365) MeOH.
Analysis calcd. for $C_{23}H_{29}N_3O_3.1$ 1/16HCl.¾H₂O (MW=447.75); C, 61.70; H, 7.11; N, 9.38; Cl, 8.41. Found: C, 61.71; ;L H, 6.74; N, 9.31; Cl, 8.52.

EXAMPLE 166

2,6-dimethyl-L-tyrosyl-N-(3-phenyl-2Z-propenyl)-D-alaninamide, hydrochloride

UF isomer

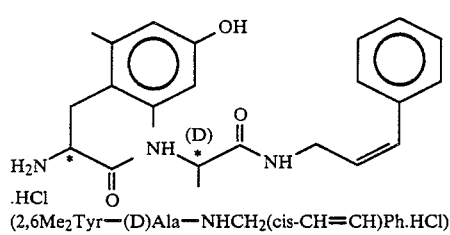

(2,6Me₂Tyr—(D)Ala—NHCH₂(cis-CH=CH)Ph.HCl)

The title compound was prepared from the UF-diastereomer of Example 164 by the method of Example 6. NMR shift of the (D)Ala methyl=0.89δ (DMSOd₆).
Optical rotation $[\alpha]_D$+114.9°, +402.6° (365) MeOH.
Analysis calcd. for $C_{23}H_{29}N_3O_3.1$ 1/16HCl.½H₂O (MW=443.25); C, 62.32; H, 6.06; N, 9.48; Cl, 8.50. Found: C, 62.35; H, 6.83; N, 9.72; Cl, 8.53.

EXAMPLE 167

Preparation of

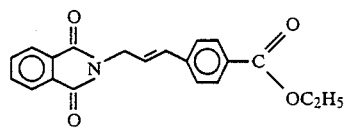

The title product was prepared by the method of Example 135 substituting ethyl 4-bromobenzoate for the 1-fluoro-4-iodobenzene and in addition adding 413 mg tri-o-tolyl phosphene.

The reaction mixture was partitioned in DMF at 90° and filtered. The filtrate was cooled to 0° and filtered. The product was dried under vacuum.

Analysis calcd. for $C_{20}H_{17}NO_4$ (MW=335.36): C, 71.27; H, 4.91; N, 4.24. Found: C, 71.63; H, 5.11; N, 4.18.

EXAMPLE 168

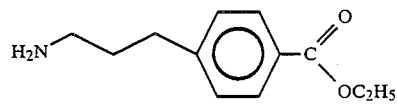

The product of Example 167 (23.00 g, 0.686 moles) and sodium borohydride was suspended in a solution of 614 ml of 2-propanol and 104 ml of water. Glacial acetic acid (71.8 ml, 1.25 moles) was added dropwise cautiously at first. The mixture was heated at reflux for 2 h. The solvent was removed under vacuum and the residue partitioned in water and CH₂Cl₂. The aqueous layer was separated, washed twice with CH₂Cl₂, and then rendered alkaline with potassium carbonate. The resultant oil was extracted with CH₂Cl₂, dried over Na₂SO₄ and concentrated under vacuo. The title compound (7.8 g) was used without further purification.

EXAMPLE 169

(Z—(D)Ala-NHCH₂CH=CH(4-CO₂Et)Ph)

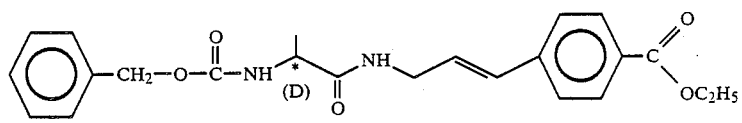

The title compound was prepared from the product of Example 168 using the method of Example 8. The title compound was purified by PLC on Porasil eluting with 1 to 2% MeOH/CH₂Cl₂.

NMR shift of the (D)Ala methyl=1.39δ (CDCl₃).

EXAMPLE 170

((D)Ala-NH(CH₂)₃(4-CO₂Et)Ph)

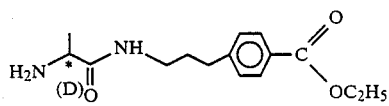

The title compound was prepared by hydrogenation of the product of Example 169 using the method of Example 121.

NMR shift of the (D)Ala methyl=1.31δ (CDCl₃).

EXAMPLE 171

(Boc-(DL)2,6Me₂Tyr-(D)Ala-NH(CH₂)₃(4-CO₂Et)Ph)

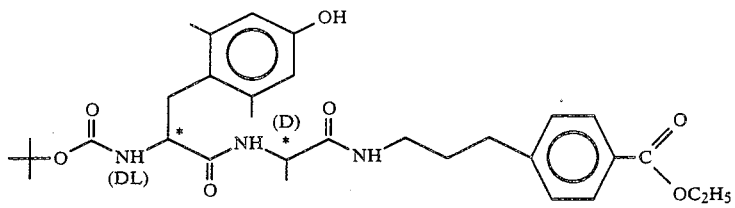

The title diastereomers were prepared by the method of Example 45 using the product of Example 170 and substituting DMF for the CH₂Cl₂. The diastereomers were separated by PLC on Merck silica eluting with a 3/7: MeOH/CHCl₃ solution containing 0.1% NH₄OH.

Diastereomer DF: NMR shift of the (D)Ala methyl=0.99δ.

Diastereomer UF: NMR shift of the (D)Ala methyl=1.18δ.

EXAMPLE 172

2,6-dimethyltyrosyl-N-[3-(4-ethoxycarbonylphenyl)-propyl]-D-alaninamide, hydrochloride

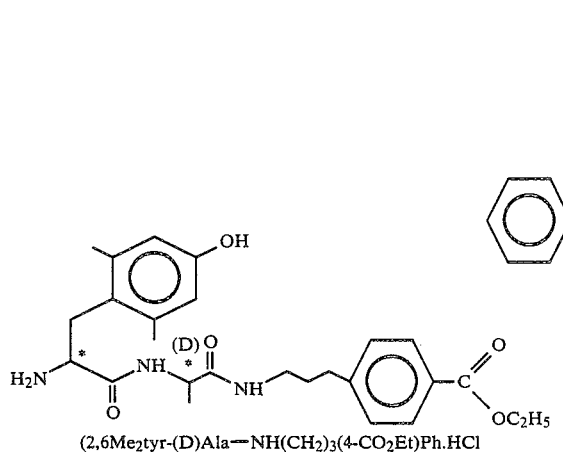

(2,6Me₂tyr-(D)Ala—NH(CH₂)₃(4-CO₂Et)Ph.HCl)

The title compound was prepared from the DF-diastereomer of Example 171 by the method of Example 6.
NMR shift of (D)Ala methyl=1.15δ (DMSOd₆)
Optical rotation [α]_D −64.4°; −239.0° MeOH.
Analysis Calcd. for C₂₆H₃₅N₃O₅.HCl.½H₂O (MW=515.05): C, 60.63; H, 7.24; N, 8.16; Cl, 6.88. Found: C, 60.60; H, 6.94; N, 8.05; Cl, 6.86.

EXAMPLE 173

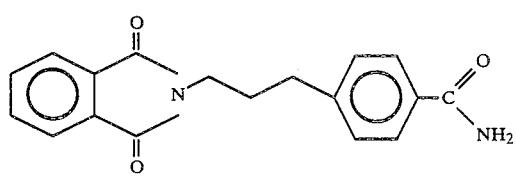

The title compound was prepared using the method of Example 135 substituting 4-iodobenzamide for the 1-fluoro-4-iodo-benzene.

EXAMPLE 174

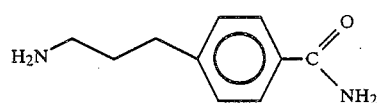

The title compound was prepared from the product of Example 173 using the method of Example 48. It was necessary to purify the product further by adding 4 equivalents of 3% NaOH and extracting this with CH₂Cl₂ using a liquid-liquid extractor for 24 hours. The solvent was removed in vacuo from the organic extract and the resultant solid was used without further purification.

EXAMPLE 175

(Z-(D)Ala-NH(CH₂)₃(4-CONH₂)Ph)

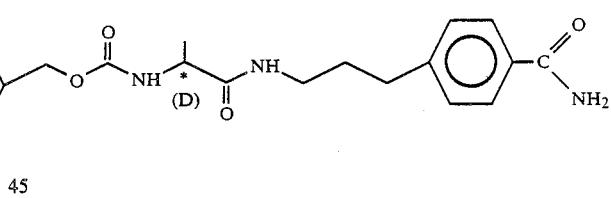

The title compound was prepared by the method of Example 8 using the product of Example 174 in place of NH₂Ad.HCl and using one equivalent less of NMM. The reaction mixture was filtered and the filtrate was diluted with water to obtain the solid product. This was filtered, washed with water on the funnel and dried under vacuum. The product was used without further purification.

EXAMPLE 176

((D)Ala-NH(CH₂)₃(4-CONH₂)Ph)

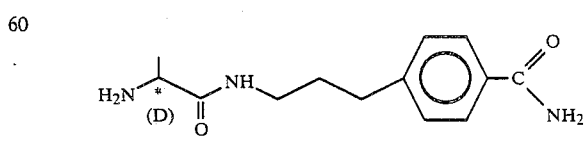

The title compound was prepared by the method of Example 9 substituting the product of Example 175 for the product of Example 8.

EXAMPLE 177

(Boc(DL)2,6Me₂Tyr-(D)Ala-NH(CH₂)₃(4-CONH₂)Ph)

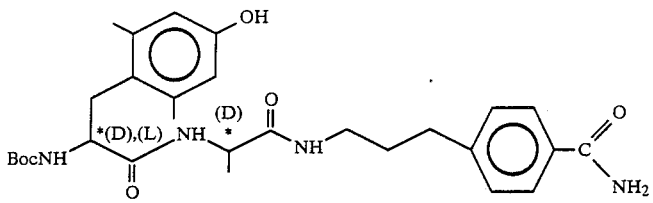

The title diastereomers were prepared by the method of Example 45 using the product of Example 176 and substituting DMF for the CH₂Cl₂.

The reaction mixture was filtered and the filtrate was partitioned in EtOAc and 0.5N KHSO₄ solution. The organic layer was separated and washed successively with a 0.5N KHSO₄ solution and brine at which point the DF diastereomer precipitated from the organic solution. This was filtered off, triturated with MeOH and used without further purification. The mother liquors were stripped under reduced pressure. The residue, containing mainly the UF diastereomer after was purified further by LPC on Woelm Silica eluting with 20% isopropanol/methyl t-butyl ether with 0.1% NH₄OH.

Diastereomer DF NMR shift of the (D)Ala methyl=1.18δ (DMSOd₆).

Diastereomer UF
NMR shift of the (D)Ala methyl=0.99δ (DMSOd₆).

EXAMPLE 178

2,6-dimethyl-D-tyrosyl-N-[3-(4-aminocarbonylphenyl)-propyl]-D-alaninamide, hydrochloride DF isomer

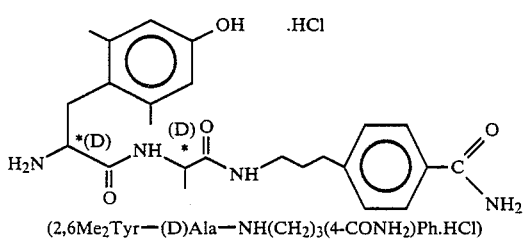

(2,6Me₂Tyr—(D)Ala—NH(CH₂)₃(4-CONH₂)Ph.HCl)

The title compound was prepared from the DF diastereomer of Example 177 by the method of Example 6.
NMR shift of (D)Ala methyl=1.16δ (DMSOd₆).
Optical rotation [α]_A −78.0°; 229.3° (365) MeOH.

Analysis Calcd. for C₂₄H₃₂N₄O₄.HCl.1½H₂O (MW=497.27): C, 57.97; H, 7.15; N, 11.27; Cl, 71.13. Found: C, 57.75; H, 6.75; N, 11.02; Cl, 7.22.

EXAMPLE 179

(Z-(DL)2,6Me₂Tyr)

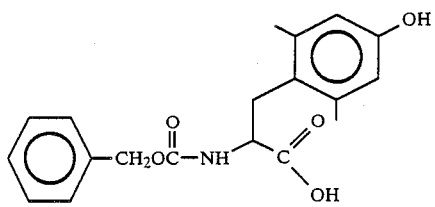

(DL)2,6-dimethyltyrosine hydrochloride (20.0 g) was dissolved in 1 liter of water. The pH was adjusted to 8.5 (10% NaOH in H₂O) and benzyl chloroformate (14.3 g) was added in one portion. The pH was maintained between 7 and 8 with the aqueous NaOH for 2 hours. The reaction mixture was then acidified (conc. HCl) and extracted with ethyl acetate. The aqueous layer was saturated with NaCl, and then extracted twice with ethyl acetate. The organic fractions were combined, dried (Na₂SO₄), filtered, and stripped to an oil. This oil was triturated with ether/hexane, giving a solid. The solid was ground up and dried overnight at 42° C. and 110 torr.

EXAMPLE 180

(Z-(DL)2,6Me₂Tyr-(D)Ala-NH(CH₂)Ph)

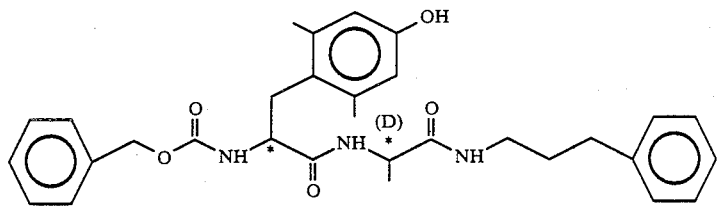

The title diastereomers were prepared by the method of Example 45 using D-alanylphenylpropylamide as the C-terminal unit and substituting the product of Example 179 for the t-butoxycarbonyl-2-6-dimethyltyrosine and DMF for the CH₂Cl₂. The diastereomers were separated by gradient PLC on silica gel eluting with 1.5 to 5% MeOH/CHCl₃.

Diastereomer DF: NMR shift of the (D)Ala methyl=1.20δ (DMSOd₆).
Diastereomer UF: NMR shift of the (D)Ala methyl=1.00δ (DMSOd₆).

EXAMPLE 181

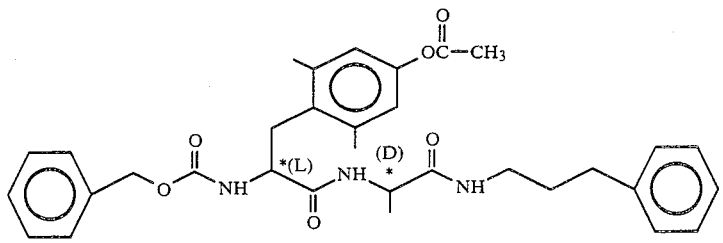

(Z—2,6Me₂Tyr(OAc)—CD)Ala—NH(CH₂)₃Ph)

The UF diastereomer of the title product from Example 180 (3.85 g, 0.00724 moles) was dissolved in 300 ml of acetonitrile and triethylamine (0.00836 moles, 0.85 g). Acetylchloride (0.00836 moles, 6.56 g) was added dropwise to the stirred mixture while maintaining the reaction temperature at 25°. The reaction was stirred until no starting material was present as determined by TLC. The reaction mixture was partitioned between CH₂Cl₂ and sufficient 5% KHSO₄ solution to render the mixture acidic. The organic layer was separated, washed once with 5% KHSO₄ solution and once with brine. After drying over anhydrous. Na₂SO₄, the solvent was removed under vacuum. The white solid (3.86 g) was used without further purification.

NMR shift of (D)Ala methyl=0.97δ (DMSOd₆).

Analysis calcd. for C₃₃H₃₉N₃O₆ (MW=573.69): Calc.: C, 69.09; H, 6.85; N, 7.32. Found: C, 68.93; H, 6.81; N, 7.33.

EXAMPLE 182

2,6-dimethyl-O[methylcarbonyl]-L-tyrosyl-N-(3-phenylpropyl)-D-alaninamide, hydrochloride

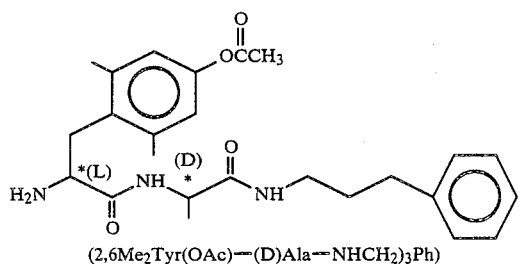

(2,6Me₂Tyr(OAc)—(D)Ala—NHCH₂)₃Ph)

The title material was prepared as described in Example 9 using the title product of Example 181 substituting glacial acetic acid for the methanol. The product was dried under vacuum over NaOH for 5 days.

Optical rotation [α]$_D$+96.1; +327.9 (365) MeOH.

NMR shift for (D)Ala methyl=1.03δ (DMSOd₆).

Analysis calcd. for C₂₅H₃₃N₃O₄.1⅜H₂O (MW=464.33): Calc.: C, 64.67; H, 7.76; N, 9.05. Found: C, 64.69; H, 7.37; N, 8.68.

EXAMPLE 183

Analgesic Properties of the Substituted Dipeptide Amides

The receptor binding and biological properties of the following compounds of this invention are illustrated in Table 1 utilizing the previously described opiate binding and writhing assay. The standard screening dose for the writhing assay was 10 mg/kg s.c. and p.o. The standard screening dose for the opiate binding assay was $10^{-5}$ molar.

TABLE 1
ANALGESIC PROPERTIES

| Example | Opiate[a] Binding | Writhing Mouse[b] Subc. | Oral |
|---|---|---|---|
| 5 | $1.0 \times 10^{-5}$ | Inactive | Inactive |
| 7 | $1.0 \times 10^{-6}$ | Inactive | Inactive |
| 20 | Inactive | Active | Inactive |
| 21 | Inactive | Active | Inactive |
| 24 | $8.6 \times 10^{-7}$ | Lethal | Inactive |
| 25 | $8.0 \times 10^{-5}$ | Inactive | Inactive |
| 29 | $4.9 \times 10^{-6}$ | Inactive | Inactive |
| 30 | $6.1 \times 10^{-8}$ | Inactive | Inactive |
| 32 | Inactive | Inactive | Active |
| 35 | $1.4 \times 10^{-8}$ | Active | Active |
| 37 | $1.4 \times 10^{-6}$ | Inactive | Inactive |
| 39 | $1.2 \times 10^{-9}$ | Inactive | Inactive |
| 44 | Inactive | Active | Active |
| 46 | $2.2 \times 10^{-7}$ | Inactive | Inactive |
| 47 | $2.9 \times 10^{-9}$ | Active | Active |
| 52 | $1.3 \times 10^{-8}$ | Active | Inactive |
| 58 | $1.0 \times 10^{-9}$ | Active | Inactive |
| 60 | $3.6 \times 10^{-5}$ | Active | Active |
| 68 | $1.1 \times 10^{-9}$ | Active | Inactive |
| 73 | $3.0 \times 10^{-10}$ | Active | Inactive |
| 85 | — | Active | Inactive |
| 108 | $8.2 \times 10^{-9}$ | Active | Inactive |
| 109 | $4.0 \times 10^{-10}$ | Active | Inactive |
| 115 | $8.7 \times 10^{-9}$ | Active | Active |

[a] = IC₅₀ expressed as moles/liter
[b] = Active refers to the effect of the screening dose (10 mg/kg).

What is claimed is:

1. A compound of the formula:

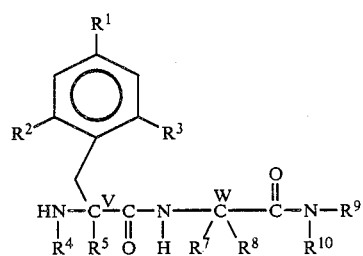

or a pharmaceutically acceptable acid addition salt thereof wherein R¹ is hydrogen, lower alkyl, hydroxy, lower alkoxy, —OCO₂—lower alkyl, —O(CH₂)$_n$—phenyl with the phenyl optionally substituted by a member of the group comprising halogen, —NO₂, —CN, —NH₂, or lower alkyl wherein n is an integer from 1 to 4; R² and R³ represent lower alkyl, halogen, or lower alkoxy, or either one of R² and R³ is hydrogen and the other is lower alkyl, lower alkoxy, or halogen; wherein R⁴, R⁵, R⁶, R⁷, R⁸ and R⁹ may be the same or different and represent hydrogen or lower alkyl; and R¹⁰ is selected from the group consisting of

—(ALK)X wherein ALK represents alkylene, thioalkylene, oxyalkylene having 1 to 5 carbon atoms; alkenylene and alkynylene having 2 to 4 carbon atoms; and X represents 9H-fluoren-9-yl; V represents an asymmetric carbon atom that may be racemic or have the D or L configuration; and W represents an asymmetric carbon atom when $R^7$ and $R^8$ are not the same which may be racemic or have the D or L configuration.

2. A compound of the formula:

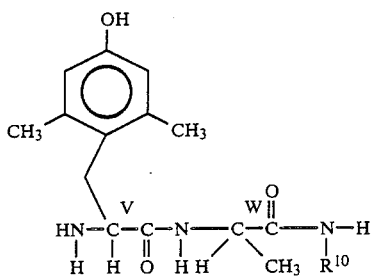

or a pharmaceutically acceptable salt thereof wherein $R^{10}$ is selected from the group consisting of

—(ALK)X wherein ALK represents alkylene, thioalkylene, oxyalkylene, having 1 to 4 carbon atoms; alkenylene or alkynylene having 2 to 4 carbon atoms; and X represents 9H-fluoren-9-yl; V and W represent asymmetric carbon atoms that may independently be racemic or have the D or L configuration.

3. A compound according to claim 2 which is 2,6-dimethyl-L-tyrosyl-N-[2-(9H-fluoren-9-yl)ethyl]-D-alaninamide, hydrochloride and the diastereomers thereof.

4. A pharmaceutical composition for treating pain in mammals comprising a therapeutically effective amount of a compound according to claim 1 in a pharmaceutically acceptable carrier.

5. A method for treating pain in mammals comprising administering a therapeutically effective amount of a compound according to claim 1 to a mammal in need of such treatment.

* * * * *

UNITED STATES PATENT AND TRADEMARK OFFICE
CERTIFICATE OF CORRECTION

PATENT NO. : 4,847,241

DATED : July 11, 1989

INVENTOR(S) : Hansen, Jr. et al.

It is certified that error appears in the above-identified patent and that said Letters Patent is hereby corrected as shown below:

On the title page of the patent, in the Abstract, the second line under the last structure, reading "symmetric" should read -- asymmetric --.

Column 4, line 34, reading "group" should read -- acid --.

Column 10, line 1, reading "to" should read -- in --.

Column 10, the second structure, Example 3, that portion of the structure reading

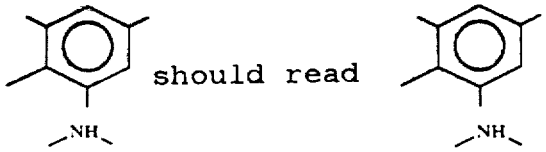

This above error also occurs in the structures for the following Examples in the patent: Examples 4, 5, 6, 7, 10, 11, 12, 13, 14, 15, 16, 17, 18, 19, 22, 23, 24, 27, 28, 29, 30, 33, 34, 35, 36, 37, 38, 39, 45, 46, 47, 51, 52, 56, 57, 58, 61, 62, 63, 66, 67, 68, 71, 72, 73, 74, 75, 76, 77, 78, 81, 83, 87, 92, 97, 103, 109, 110, 115, 116, 117, 122, 123, 124, 125, 128, 129, 132, 133, 134, 139, 149, 150, 151, 158, 159, 164, 165, 166, 171, 172, 178, 180, 181, and 182.

Column 11, line 28, reading "$CDHCl_3$" should read -- $CHCl_3$ --.

Column 21, line 42, reading "H, 8.48" should read -- N, 8.48 --.

Column 23, line 28, reading "within" should read -- without --.

Column 29, line 36, reading "C, 6.28" should read -- C, 61.28 --.

Column 32, Example 47, the following has been omitted and should be added under the structure: ($2,6-Me_2Tyr-(D)Ala-NH(CH_2)_3-2$-thiophene·HCl)

Column 32, lines 63-64, reading "birproduct" should read -- biproduct --.

Column 33, line 61, reading "(Box-" should read -- (Boc- --.

UNITED STATES PATENT AND TRADEMARK OFFICE
CERTIFICATE OF CORRECTION

PATENT NO. : 4,847,241

DATED : July 11, 1989

INVENTOR(S) : Hansen, Jr. et al.

It is certified that error appears in the above-identified patent and that said Letters Patent is hereby corrected as shown below:

Column 37, line 42, reading "(355)" should read -- (365) --.

Column 39, Example 63, the structure is illegible because the structure from Example 66 (Column 40) has been superimposed over it. The structure for Example 63, reading

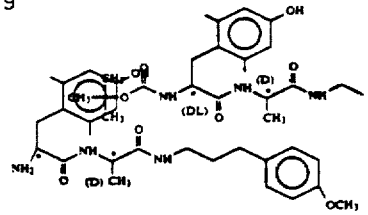

should read

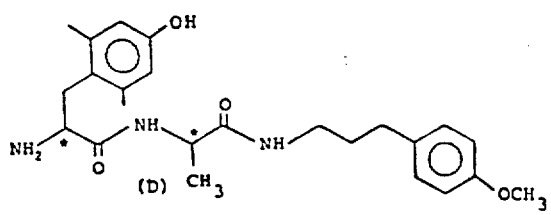

Column 40, the first structure, Example 66, should read

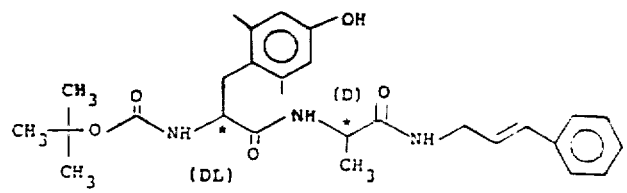

UNITED STATES PATENT AND TRADEMARK OFFICE
CERTIFICATE OF CORRECTION

PATENT NO. : 4,847,241
DATED : July 11, 1989
INVENTOR(S) : Hansen, Jr. et al.

It is certified that error appears in the above-identified patent and that said Letters Patent is hereby corrected as shown below:

Column 41, line 17, reading "-NHCH$_2$CH)$_2$Ph. HCl)" should read -- -NHCH$_2$(CH)$_2$Ph·HCl) --.

Column 43, line 60, reading "(CH)-3Pyr)" should read -- (CH)$_2$-3Pyr) --.

Column 48, line 48, reading "H, 6.20" should read -- N, 6.20 --.

Column 50, the third structure should be deleted. (This structure is the structure for Example 92.)

Column 50, line 66, reading "O$_2$ (MW" should read -- O$_2$ H$_2$O (MW --.

Column 51, Scheme I, Route A, does not belong here and should be deleted. (Scheme I, Route A, is shown correctly in Columns 4-5.) This Scheme should be replaced with the third structure in Column 50, the correct structure for Example 92.

Column 54, line 30, reading C$_{24}$H$_{31}$N$_5$O$_5$.1/8C$_4$H$_8$O$_2$.1/4H$_2$O" should read -- C$_{24}$H$_{31}$N$_3$O$_5$·1/8C$_4$H$_8$O$_2$·HCl·1/4H$_2$O --.

Column 56, line 29, reading "11/8HCl.1/8HCl.1/8C$_4$" should read -- 11/8HCl·1/8C$_4$ --.

Column 56, line 30, reading "N, 8.83" should read -- N, 8.73 --.

Column 57, Example 106, the following should be added under the structure: (Boc-(D)Ala-NH(CH$_2$)$_2$SPh)

Column 57, the third structure, Example 108, reading

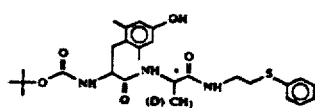   should read   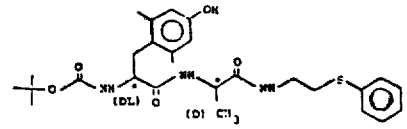

UNITED STATES PATENT AND TRADEMARK OFFICE
CERTIFICATE OF CORRECTION

PATENT NO. : 4,847,241
DATED : July 11, 1989
INVENTOR(S) : Hansen, Jr. et al.

It is certified that error appears in the above-identified patent and that said Letters Patent is hereby corrected as shown below:

Column 69, line 27, reading "(365) MeOH." should be deleted.

Column 73, line 7, reading "the poured" should read -- then poured --.

Column 76, line 68, reading "=B 1.00$\delta$" should read -- = 1.00$\delta$ --.

Column 77, line 25, reading ";L H, 6.74" should read -- H, 6.74 --.

Column 77, line 57, reading "H, 6.06" should read -- H, 7.06 --.

Column 78, line 28, reading "vacuo" should read -- vacuum --.

Column 83, the first line under the second structure, Example 182, reading "-NHCH$_2$)$_3$Ph)" should read -- -NH(CH$_2$)$_3$Ph) --.

Claim 2, Column 86, line 1, reading "salt" should read -- addition salt --.

Signed and Sealed this

Twentieth Day of April, 1993

Attest:

MICHAEL K. KIRK

*Attesting Officer*  *Acting Commissioner of Patents and Trademarks*